(12) United States Patent
Van Hooser et al.

(10) Patent No.: US 11,894,139 B1
(45) Date of Patent: Feb. 6, 2024

(54) DISEASE SPECTRUM CLASSIFICATION

(71) Applicant: PatientsLikeMe LLC, Cambridge, MA (US)

(72) Inventors: Aaron Van Hooser, Lowell, MA (US); Renee Deehan-Kenney, Cambridge, MA (US)

(73) Assignee: PatientsLikeMe LLC, Cambridge, MA (US)

( * ) Notice: Subject to any disclaimer, the term of this patent is extended or adjusted under 35 U.S.C. 154(b) by 615 days.

(21) Appl. No.: 16/702,329

(22) Filed: Dec. 3, 2019

Related U.S. Application Data

(60) Provisional application No. 62/818,310, filed on Mar. 14, 2019, provisional application No. 62/774,788, filed on Dec. 3, 2018.

(51) Int. Cl.
| | | |
|---|---|---|
| *G16H 50/20* | (2018.01) | |
| *G06N 20/20* | (2019.01) | |
| *G06N 20/10* | (2019.01) | |
| *G16H 50/70* | (2018.01) | |
| *G16H 10/40* | (2018.01) | |

(52) U.S. Cl.
CPC ............. *G16H 50/20* (2018.01); *G06N 20/10* (2019.01); *G06N 20/20* (2019.01); *G16H 10/40* (2018.01); *G16H 50/70* (2018.01)

(58) Field of Classification Search
CPC ......... G16H 10/00–80/00; G06N 3/00–99/007
See application file for complete search history.

(56) References Cited

U.S. PATENT DOCUMENTS

| | | |
|---|---|---|
| 3,934,226 A | 1/1976 | Stone et al. |
| 4,712,562 A | 12/1987 | Ohayon et al. |
| 4,899,839 A | 2/1990 | Dessertine et al. |
| 5,014,798 A | 5/1991 | Glynn |
| 5,025,374 A | 6/1991 | Roizen et al. |
| 5,435,324 A | 7/1995 | Brill |
| 5,549,117 A | 8/1996 | Tacklind et al. |
| 5,594,637 A | 1/1997 | Eisenberg et al. |
| 5,594,638 A | 1/1997 | Iliff |
| 5,626,144 A | 5/1997 | Tacklind et al. |
| 5,653,739 A | 8/1997 | Maurer et al. |

(Continued)

FOREIGN PATENT DOCUMENTS

| | | |
|---|---|---|
| CA | 2884613 | 3/2014 |
| DE | 3703404 A1 | 8/1988 |

(Continued)

OTHER PUBLICATIONS

Piri et al., "A data analytics approach to building a clinical decision support system for diabetic retinopathy: Developing and deploying a model ensemble," Decision Support Systems 101 (2017) 12-27 (Year: 2017).*

(Continued)

*Primary Examiner* — Jonathon A. Szumny
(74) *Attorney, Agent, or Firm* — Greenberg Traurig, LLP; David J. Dykeman; Nicholas Martin

(57) ABSTRACT

Described herein are systems, media, and methods for assessing an individual by generating a classification or regression based on input data comprising metabolite information, protein information, nucleic acid information, non-molecular information, or any combination thereof.

18 Claims, 48 Drawing Sheets

(56) References Cited

U.S. PATENT DOCUMENTS

| | | |
|---|---|---|
| 5,692,215 A | 11/1997 | Kutzik et al. |
| 5,692,500 A | 12/1997 | Gaston-Johansson |
| 5,704,366 A | 1/1998 | Tacklind et al. |
| 5,713,350 A | 2/1998 | Yokota et al. |
| 5,720,502 A | 2/1998 | Cain |
| 5,732,709 A | 3/1998 | Tacklind et al. |
| 5,778,882 A | 7/1998 | Raymond et al. |
| 5,812,983 A | 9/1998 | Kumagai |
| 5,830,149 A | 11/1998 | Oka |
| 5,838,313 A | 11/1998 | Hou et al. |
| 5,937,387 A | 8/1999 | Summerell et al. |
| 5,950,168 A | 9/1999 | Simborg et al. |
| 5,984,368 A | 11/1999 | Cain |
| 5,991,729 A | 11/1999 | Barry et al. |
| 6,024,699 A | 2/2000 | Surwit et al. |
| 6,032,119 A | 2/2000 | Brown et al. |
| 6,067,523 A | 5/2000 | Bair et al. |
| 6,081,786 A | 6/2000 | Barry et al. |
| 6,102,874 A | 8/2000 | Stone et al. |
| 6,108,635 A | 8/2000 | Herren et al. |
| 6,108,685 A | 8/2000 | Kutzik et al. |
| 6,113,552 A | 9/2000 | Shimazu et al. |
| 6,168,569 B1 | 1/2001 | McEwen et al. |
| 6,186,145 B1 | 2/2001 | Brown |
| 6,231,560 B1 | 5/2001 | Bui et al. |
| 6,234,964 B1 | 5/2001 | Iliff |
| 6,235,964 B1 | 5/2001 | Kadash et al. |
| 6,236,983 B1 | 5/2001 | Hofmann et al. |
| 6,246,992 B1 | 6/2001 | Brown |
| 6,277,072 B1 | 8/2001 | Bardy |
| 6,282,441 B1 | 8/2001 | Raymond et al. |
| 6,283,923 B1 | 9/2001 | Finkelstein et al. |
| 6,294,999 B1 | 9/2001 | Yarin et al. |
| 6,314,405 B1 | 11/2001 | Richardson |
| 6,322,504 B1 | 11/2001 | Kirshner |
| 6,334,192 B1 | 12/2001 | Karpf |
| 6,335,907 B1 | 1/2002 | Momich et al. |
| 6,339,410 B1 | 1/2002 | Milner et al. |
| 6,380,858 B1 | 4/2002 | Yarin et al. |
| 6,400,996 B1 | 6/2002 | Hoffberg et al. |
| 6,405,034 B1 | 6/2002 | Tijerino |
| 6,484,144 B2 | 11/2002 | Martin et al. |
| 6,529,195 B1 | 3/2003 | Eberlein |
| 6,560,541 B1 | 5/2003 | Singh |
| 6,587,829 B1 | 7/2003 | Camarda et al. |
| 6,589,169 B1 | 7/2003 | Surwit et al. |
| 6,611,846 B1 | 8/2003 | Stoodley |
| 6,612,985 B2 | 9/2003 | Eiffert et al. |
| 6,690,397 B1 | 2/2004 | Daignault, Jr. |
| 6,723,045 B2 | 4/2004 | Cosentino et al. |
| 6,770,029 B2 | 8/2004 | Iliff |
| 6,789,091 B2 | 9/2004 | Gogolak |
| 6,802,810 B2 | 10/2004 | Ciarniello et al. |
| 6,856,315 B2 | 2/2005 | Eberlein |
| 6,915,170 B2 | 7/2005 | Engleson et al. |
| 6,929,607 B2 | 8/2005 | Lipman |
| 6,956,572 B2 | 10/2005 | Zaleski |
| 6,970,742 B2 | 11/2005 | Mann et al. |
| 6,980,958 B1 | 12/2005 | Surwit et al. |
| 6,988,075 B1 | 1/2006 | Hacker |
| 6,999,890 B2 | 2/2006 | Kai |
| 7,029,441 B2 | 4/2006 | Dodds |
| 7,039,878 B2 | 5/2006 | Auer et al. |
| 7,054,758 B2 | 5/2006 | Gill-Garrison et al. |
| 7,066,883 B2 | 6/2006 | Schmidt et al. |
| 7,107,547 B2 | 9/2006 | Cule et al. |
| 7,137,951 B2 | 11/2006 | Pilarski |
| 7,165,221 B2 | 1/2007 | Monteleone et al. |
| 7,169,085 B1 | 1/2007 | Killin et al. |
| 7,251,609 B1 | 7/2007 | McAlindon et al. |
| 7,286,997 B2 | 10/2007 | Spector et al. |
| 7,287,031 B1 | 10/2007 | Karpf et al. |
| 7,302,398 B2 | 11/2007 | Ban et al. |
| 7,330,818 B1 | 2/2008 | Ladocsi et al. |
| 7,337,121 B1 | 2/2008 | Beinat et al. |
| 7,428,494 B2 | 9/2008 | Hasan et al. |
| 7,725,328 B1 | 5/2010 | Sumner, II et al. |
| 7,761,311 B2 | 7/2010 | Clements et al. |
| 8,160,901 B2 | 4/2012 | Heywood et al. |
| 8,190,451 B2 | 5/2012 | Lloyd et al. |
| 8,214,224 B2 | 7/2012 | Rao et al. |
| 8,313,433 B2 | 11/2012 | Cohen et al. |
| 8,643,648 B2 | 2/2014 | Heywood et al. |
| 8,652,039 B2 | 2/2014 | Rosales et al. |
| 8,930,224 B2 | 1/2015 | Heywood et al. |
| 9,270,632 B2 | 2/2016 | Heywood et al. |
| 9,589,104 B2 | 3/2017 | Heywood et al. |
| 9,589,251 B2 | 3/2017 | Heywood et al. |
| 9,638,723 B2 | 5/2017 | Takagi et al. |
| 10,402,916 B2 | 9/2019 | Heywood et al. |
| 10,664,572 B2 | 5/2020 | Bitran et al. |
| 10,665,344 B2 | 5/2020 | Heywood et al. |
| 10,832,816 B2 | 11/2020 | Heywood et al. |
| 11,010,843 B2 | 5/2021 | Heywood et al. |
| 2001/0034639 A1 | 10/2001 | Jacoby et al. |
| 2002/0010595 A1 | 1/2002 | Kapp |
| 2002/0026103 A1 | 2/2002 | Norris et al. |
| 2002/0072933 A1 | 6/2002 | Vonk et al. |
| 2002/0150872 A1 | 10/2002 | Glenn et al. |
| 2002/0177757 A1 | 11/2002 | Britton |
| 2002/0184094 A1 | 12/2002 | Calloway |
| 2003/0014006 A1 | 1/2003 | Alexandre et al. |
| 2003/0023461 A1 | 1/2003 | Quintanilla et al. |
| 2003/0065535 A1 | 4/2003 | Karlov et al. |
| 2003/0101076 A1 | 5/2003 | Zaleski |
| 2003/0125609 A1 | 7/2003 | Becker |
| 2003/0135128 A1 | 7/2003 | Suffin et al. |
| 2003/0140063 A1 | 7/2003 | Pizzorno et al. |
| 2003/0163353 A1 | 8/2003 | Luce et al. |
| 2003/0187683 A1 | 10/2003 | Kirchhoff et al. |
| 2003/0233197 A1 | 12/2003 | Padilla et al. |
| 2004/0006444 A1 | 1/2004 | Kang et al. |
| 2004/0015337 A1 | 1/2004 | Thomas et al. |
| 2004/0030741 A1 | 2/2004 | Wolton et al. |
| 2004/0064447 A1 | 4/2004 | Simske et al. |
| 2004/0078237 A1 | 4/2004 | Kaafarani et al. |
| 2004/0103001 A1 | 5/2004 | Mazar et al. |
| 2004/0122707 A1 | 6/2004 | Sabol et al. |
| 2004/0132633 A1 | 7/2004 | Carter et al. |
| 2004/0161143 A1 | 8/2004 | Dietz et al. |
| 2004/0193448 A1 | 9/2004 | Woodbridge et al. |
| 2004/0210458 A1 | 10/2004 | Evans et al. |
| 2004/0225529 A1 | 11/2004 | Snyder et al. |
| 2004/0267570 A1 | 12/2004 | Becker |
| 2005/0080462 A1 | 4/2005 | Jenkins et al. |
| 2005/0085866 A1 | 4/2005 | Tehrani |
| 2005/0102160 A1 | 5/2005 | Brown |
| 2005/0102162 A1 | 5/2005 | Blumenfeld |
| 2005/0108051 A1 | 5/2005 | Weinstein |
| 2005/0119534 A1 | 6/2005 | Trost et al. |
| 2005/0144042 A1 | 6/2005 | Joffe et al. |
| 2005/0187866 A1 | 8/2005 | Lee |
| 2005/0191716 A1 | 9/2005 | Surwit et al. |
| 2005/0197545 A1 | 9/2005 | Hoggle |
| 2005/0197553 A1 | 9/2005 | Cooper |
| 2005/0216307 A1 | 9/2005 | Clements et al. |
| 2005/0251025 A1* | 11/2005 | Hancu ............ G01R 33/465 600/431 |
| 2005/0272640 A1 | 12/2005 | Doyle et al. |
| 2005/0283384 A1 | 12/2005 | Hunkeler et al. |
| 2005/0283385 A1 | 12/2005 | Hunkeler et al. |
| 2005/0285746 A1 | 12/2005 | Sengupta et al. |
| 2006/0009810 A1 | 1/2006 | Mann et al. |
| 2006/0010098 A1 | 1/2006 | Goodnow et al. |
| 2006/0015369 A1 | 1/2006 | Bachus et al. |
| 2006/0020175 A1 | 1/2006 | Berry et al. |
| 2006/0030890 A1 | 2/2006 | Cosentino et al. |
| 2006/0031101 A1 | 2/2006 | Ross |
| 2006/0036134 A1 | 2/2006 | Tarassenko et al. |
| 2006/0036294 A1 | 2/2006 | Tehrani |
| 2006/0036619 A1 | 2/2006 | Fuerst et al. |
| 2006/0052945 A1 | 3/2006 | Rabinowitz et al. |
| 2006/0059160 A1 | 3/2006 | Smola et al. |
| 2006/0064030 A1 | 3/2006 | Cosentino et al. |

(56) References Cited

U.S. PATENT DOCUMENTS

| | | |
|---|---|---|
| 2006/0085217 A1 | 4/2006 | Grace |
| 2006/0089540 A1 | 4/2006 | Meissner |
| 2006/0122468 A1 | 6/2006 | Tavor |
| 2006/0249423 A1 | 11/2006 | Reijonen |
| 2006/0287885 A1 | 12/2006 | Frick |
| 2007/0005393 A1 | 1/2007 | Cole et al. |
| 2007/0015974 A1 | 1/2007 | Higgins et al. |
| 2007/0021979 A1 | 1/2007 | Cosentino et al. |
| 2007/0021984 A1 | 1/2007 | Brown |
| 2007/0048691 A1 | 3/2007 | Brown |
| 2007/0060803 A1 | 3/2007 | Liljeryd et al. |
| 2007/0061166 A1 | 3/2007 | Ramasubramanian et al. |
| 2007/0061487 A1 | 3/2007 | Moore et al. |
| 2007/0115282 A1 | 5/2007 | Turner et al. |
| 2007/0118348 A1 | 5/2007 | Brown |
| 2007/0168461 A1 | 7/2007 | Moore |
| 2007/0168501 A1 | 7/2007 | Cobb et al. |
| 2007/0203423 A1 | 8/2007 | Bardy |
| 2007/0214015 A1 | 9/2007 | Christian |
| 2007/0239416 A1 | 10/2007 | Saito et al. |
| 2007/0244372 A1 | 10/2007 | Merkle |
| 2007/0250134 A1 | 10/2007 | Miesel et al. |
| 2007/0288266 A1 | 12/2007 | Sysko et al. |
| 2008/0010089 A1 | 1/2008 | DiMaggio et al. |
| 2008/0015891 A1 | 1/2008 | Lee |
| 2008/0020877 A1 | 1/2008 | Bogner |
| 2008/0059232 A1 | 3/2008 | Iliff |
| 2008/0076976 A1 | 3/2008 | Sakurai et al. |
| 2008/0077489 A1 | 3/2008 | Gilley et al. |
| 2008/0091084 A1 | 4/2008 | Yudkovitch et al. |
| 2008/0109412 A1 | 5/2008 | Drayer et al. |
| 2008/0119958 A1 | 5/2008 | Bear et al. |
| 2008/0133269 A1 | 6/2008 | Ching |
| 2008/0133716 A1 | 6/2008 | Rao et al. |
| 2008/0140449 A1 | 6/2008 | Hayes |
| 2008/0147440 A1 | 6/2008 | Kil |
| 2008/0147441 A1 | 6/2008 | Kil |
| 2008/0147688 A1 | 6/2008 | Beekmann et al. |
| 2008/0200771 A1 | 8/2008 | Brown |
| 2008/0201174 A1 | 8/2008 | Ramasubramanian et al. |
| 2008/0208777 A1 | 8/2008 | Stephens |
| 2008/0229213 A1 | 9/2008 | Hamilton et al. |
| 2008/0238666 A1 | 10/2008 | Loncar |
| 2008/0249806 A1 | 10/2008 | Dlugos et al. |
| 2008/0312510 A1 | 12/2008 | Ross |
| 2008/0313256 A1 | 12/2008 | Kanazawa et al. |
| 2009/0018862 A1 | 1/2009 | Sanger et al. |
| 2009/0037470 A1 | 2/2009 | Schmidt |
| 2009/0048865 A1 | 2/2009 | Breazeale, Jr. |
| 2009/0055150 A1 | 2/2009 | Prior et al. |
| 2009/0131758 A1* | 5/2009 | Heywood ............ A61B 5/4824 600/300 |
| 2009/0144089 A1 | 6/2009 | Heywood et al. |
| 2009/0150180 A1 | 6/2009 | Cohen et al. |
| 2009/0172773 A1 | 7/2009 | Moore |
| 2009/0222284 A1 | 9/2009 | McEachern |
| 2009/0234755 A1 | 9/2009 | Sidoruk |
| 2010/0070306 A1 | 3/2010 | Dvorak et al. |
| 2010/0131860 A1 | 5/2010 | DeHaan et al. |
| 2010/0286490 A1 | 11/2010 | Koverzin |
| 2011/0029895 A1 | 2/2011 | Ternouth |
| 2011/0184747 A1 | 7/2011 | Bozic et al. |
| 2012/0116685 A1* | 5/2012 | Alaupovic ............ G16H 50/30 702/19 |
| 2012/0129139 A1 | 5/2012 | Partovi |
| 2012/0265552 A1 | 10/2012 | Rabinowitz et al. |
| 2013/0024207 A1 | 1/2013 | Anderson et al. |
| 2013/0253940 A1 | 9/2013 | Zziwa |
| 2014/0100885 A1 | 4/2014 | Stern |
| 2014/0257856 A1 | 9/2014 | Sasai |
| 2014/0350954 A1 | 11/2014 | Ellis et al. |
| 2015/0112710 A1* | 4/2015 | Haber ................ G16H 50/50 705/2 |
| 2015/0161331 A1 | 6/2015 | Oleynik |
| 2016/0103973 A1 | 4/2016 | Singal et al. |
| 2016/0135706 A1* | 5/2016 | Sullivan ............... A61B 5/316 600/509 |
| 2016/0188807 A1 | 6/2016 | Heywood et al. |
| 2016/0203281 A1 | 7/2016 | Zalis et al. |
| 2016/0228003 A1* | 8/2016 | Apte .................... G16B 40/20 |
| 2016/0232312 A1* | 8/2016 | Apte .................... G16H 50/50 |
| 2016/0300015 A1 | 10/2016 | Natarajan et al. |
| 2017/0206327 A1 | 7/2017 | Heywood et al. |
| 2017/0249434 A1* | 8/2017 | Brunner ............... G06F 16/258 |
| 2017/0262604 A1 | 9/2017 | Francois |
| 2017/0281020 A1* | 10/2017 | Mulligan .............. G16H 50/20 |
| 2017/0308671 A1* | 10/2017 | Bahrami ............... G16H 10/60 |
| 2018/0308569 A1 | 10/2018 | Luellen |
| 2019/0043610 A1* | 2/2019 | Vaughan .............. A61B 5/7267 |
| 2019/0139641 A1* | 5/2019 | Itu ....................... G06N 3/0472 |
| 2019/0211378 A1* | 7/2019 | Apte .................... G16H 20/00 |
| 2019/0339291 A1* | 11/2019 | Edmonds .............. G16H 50/30 |
| 2019/0347744 A1 | 11/2019 | Heywood et al. |
| 2020/0003762 A1* | 1/2020 | Brown .................. G16B 50/00 |
| 2020/0185063 A1* | 6/2020 | Narain .................. G01N 33/48 |
| 2020/0279622 A1 | 9/2020 | Heywood et al. |
| 2021/0057046 A1* | 2/2021 | Liu ....................... G16B 40/20 |
| 2021/0247403 A1* | 8/2021 | Arvey .................... C07K 7/06 |
| 2021/0256630 A1 | 8/2021 | Heywood et al. |

FOREIGN PATENT DOCUMENTS

| | | | |
|---|---|---|---|
| EP | 0912957 B1 | 12/2004 | |
| EP | 3287530 A1 * | 2/2018 | ......... C12Q 1/6804 |
| JP | H07271857 A | 10/1995 | |
| JP | H08140944 A | 6/1996 | |
| JP | 2001175761 A | 6/2001 | |
| JP | 2001331581 A | 11/2001 | |
| JP | 2001331585 A | 11/2001 | |
| JP | 2002011057 A | 1/2002 | |
| JP | 2002041670 A | 2/2002 | |
| JP | 2002056099 A | 2/2002 | |
| JP | 2002095641 A | 4/2002 | |
| JP | 2002512712 A | 4/2002 | |
| JP | 2002245172 A | 8/2002 | |
| JP | 2002245180 A | 8/2002 | |
| JP | 2002539561 A | 11/2002 | |
| JP | 2002366662 A | 12/2002 | |
| JP | 2003010288 A | 1/2003 | |
| JP | 2003108679 A | 4/2003 | |
| JP | 2003175005 A | 6/2003 | |
| JP | 2003186995 A | 7/2003 | |
| JP | 2003256573 A | 9/2003 | |
| JP | 2003337864 A | 11/2003 | |
| JP | 2004178264 A | 6/2004 | |
| JP | 2005004398 A | 1/2005 | |
| JP | 2005506601 A | 3/2005 | |
| JP | 2005326943 A | 11/2005 | |
| JP | 2006053628 A | 2/2006 | |
| JP | 2006155071 A | 6/2006 | |
| JP | 2006155411 A | 6/2006 | |
| JP | 2006163489 A | 6/2006 | |
| JP | 2006185396 A | 7/2006 | |
| JP | 2006221471 A | 8/2006 | |
| JP | 2006350992 A | 12/2006 | |
| JP | 2007052774 A | 3/2007 | |
| JP | 2007514207 A | 5/2007 | |
| JP | 2007140905 A | 6/2007 | |
| JP | 2007200093 A | 8/2007 | |
| JP | 2007525154 A | 9/2007 | |
| JP | 2007265347 A | 10/2007 | |
| JP | 2008513884 A | 5/2008 | |
| JP | 2008177713 A | 7/2008 | |
| JP | 2010500648 A | 1/2010 | |
| JP | 2011501276 A | 1/2011 | |
| JP | 2011501845 A | 1/2011 | |
| WO | WO 2000029983 A1 | 5/2000 | |
| WO | WO 2000055751 A1 | 9/2000 | |
| WO | WO 2001050950 A2 | 7/2001 | |
| WO | WO 2004080312 A1 | 9/2004 | |
| WO | WO 2007019504 A2 | 2/2007 | |
| WO | WO 2007023818 A1 | 3/2007 | |
| WO | WO 2007111910 A2 | 10/2007 | |
| WO | WO 2009049277 A1 | 4/2009 | |

(56) References Cited

FOREIGN PATENT DOCUMENTS

| | | | |
|---|---|---|---|
| WO | WO 2009049278 A1 | 4/2009 | |
| WO | WO 2010126577 A1 | 11/2010 | |
| WO | WO 2010148365 A2 | 12/2010 | |
| WO | WO 2012154594 | 11/2012 | |
| WO | WO 2014036312 A2 | 3/2014 | |
| WO | WO 2014039718 A1 | 3/2014 | |
| WO | WO 2014062981 A1 | 4/2014 | |
| WO | WO 2014144383 A1 | 9/2014 | |
| WO | WO 2014145123 A2 | 9/2014 | |
| WO | 2015095343 A1 | 6/2015 | |
| WO | WO-2016141127 A1 * | 9/2016 | ........... C12Q 1/6886 |
| WO | WO-2017181147 A1 * | 10/2017 | ........... C12Q 1/6883 |
| WO | WO 20170173365 A1 | 10/2017 | |
| WO | WO-2017201540 A1 * | 11/2017 | ......... G01N 15/0227 |
| WO | WO-2018079840 A1 * | 5/2018 | .............. C12M 1/34 |
| WO | WO-2018140014 A1 * | 8/2018 | ........... G06T 7/0012 |
| WO | WO-2019103738 A1 * | 5/2019 | ....... G06F 16/90332 |

OTHER PUBLICATIONS

Eom et al., "AptaCDSS-E: A classifier ensemble-based clinical decision support system for cardiovascular disease level prediction," Expert Systems with Applications 34 (2008) 2465-2479 (Year: 2008).*

Aljaaf et al., "Early Prediction of Chronic Kidney Disease Using Machine Learning Supported by Predictive Analytics," 2018 IEEE Congress on Evolutionary Computation (CEC) (Year: 2018).*

Margineanu et al., "Machine Learning Approach for Classifying Multiple Sclerosis Courses by Combining Clinical Data with Lesion Loads and Magnetic," Frontiers in Neuroscience | www.frontiersin. org Jul. 1, 2017 | vol. 11 | Article 398 (Year: 2017).*

Bratic et al., "Machine Learning for Predicting Cognitive Diseases: Methods, Data Sources and Risk Factors," J Med Syst (2018) 42: 243 (Year: 2018).*

Ko et al., "Machine learning to detect signatures of disease in liquid biopsies—a user's guide," Lab Chip, 2018, 18, 395-405 (Year: 2018).*

Alves et al., "Progression of Motor Impairment and Disability in Parkinson Disease: A Population-Based Study," Neurology, vol. 65, No. 9, pp. 1436-1441, Nov. 2005.

Banerjee et al., "R-U-In?: Doing What You Like, with People Whom You Like" In Proceedings of the 17th international conference on World Wide Web, pp. 1239-1240, Apr. 2008.

Baum et al., "A Maximization Technique Occurring in the Statistical Analysis of Probabilistic Functions of Markov Chains," Annals of Mathematical Statistics, 1970, vol. 41, No. 1, pp. 164-171.

Beenen et al., "Using Social Psychology to Motivate Contributions to Online Communities" Conference on Computer Supported Cooperative Work, Chicago, IL, Nov. 6-10, 2004.

Cedarbaum et al., "Performance of the Amyotrophic Lateral Sclerosis Functional Rating Scale (ALSFRS) in multicenter clinical trials," Journal of the Neurological Sciences, Oct. 1997, vol. 152, Supplement 1, pp. S1-S9.

Cedarbaum et al., "The ALSFRS-R: a revised ALS functional rating scale that incorporates assessments of respiratory function," Journal of the Neurological Sciences, 1999, vol. 169, pp. 13-21.

Cosley et al., "SuggestBot: Using Intelligent Task Routing to Help People Find Work in Wikipedia", IUI '07, Jan. 28-31, 2007, Honolulu, Hawaii, pp. 32-41.

Cudkowicz et al., "Measures & Markers in Amyotrophic Lateral Sclerosis," NeuroRx, Apr. 2004, vol. 1, pp. 273-283.

Dayhoff et al., "Providing a Complete Online Multimedia Patient Record," AMIA, Inc., 1999, pp. 241-245.

Deneault et al., "An Integrative Display for Patient Monitoring," IEEE International Conference on Systems, Man & Cybernetics Conference Proceedings, 1990, pp. 515-517.

Emmons et al., "Counting Blessings Versus Burdens: An Experimental Investigation of Gratitude and Subjective Well-Being in Daily Life," Journal of Personality and Social Psychology, 2003, vol. 84, No. 2, pp. 377-389.

Eton et al., "Harmonizing and Consolidating the Measurement of Patient-Reported Information at Health Care Institutions: a Position Statement of the Mayo Clinic," Patient Related Outcome Measures, pp. 7-15, 2014.

Foraker et al., "Her-based Visualization Tool: Adoption Rates, Satisfaction, and Patient Outcomes," eGEMS (Generating Evidence & Methods to Improve Patient Outcomes), vol. 3, Iss. 2, pp. 1-14, 2015.

Fornai et al., "Lithium delays progression of amyotrophic lateral sclerosis," Proceedings of the National Academy of Sciences, Feb. 12, 2008, vol. 105, No. 6, pp. 2052-2057.

Frankowski et al., "Recommenders Everywhere: the WikiLens Community-Maintained Recommender System", WikiSym '07, Oct. 21-23, 2007, Montreal, Quebec, Canada, pp. 47-59.

Frost et al., "Social Uses of Personal Health Information Within PatientsLikeMe, an Online Patient Community: What Can Happen When Patients Have Access to One Another's Data," Journal of Medical Internet Research, May 27, 2008, vol. 10, No. 3, p. e15.

Geyer et al., "Recommending Topics for Self-Descriptions in Online User Profiles", RecSys '08, Oct. 23-25, 2008, Lausanne, Switzerland, pp. 59-66.

Goetz, "Practicing Patients," The New York Times Magazine, Mar. 23, 2008.

Gordon, "Advances in Clinical Trials for Amyotrophic Lateral Sclerosis," Current Neurology & Neuroscience Reports, 2005, vol. 5, pp. 48-54.

Gordon et al., "Progression rate of ALSFRS-R at time of diagnosis predicts survival time in ALS," Neurology, Oct. 2006, vol. 67, pp. 1314-1315.

Harper et al., "Talk Amongst Yourselves: Inviting Users to Participate in Online Conversations", IUI '07, Jan. 28-31, 2007, Honolulu, Hawaii, pp. 62-71.

Ikemoto et al., "Diabetes nursing support system using mobile phones," Information Processing Society of Japan Research Report 2006-DBS-138 Database System 2006-GN-58 Groupware and Network IPSJ, Information Processing Society of Japan, Jan. 27, 2006, vol. 2006, No. 9, pp. 197-202.

Iriberri et al., "A Life-Cycle Perspective on Online Community Success", ACM Computing Surveys, vol. 41, No. 2, Article 11, Feb. 2009.

Johnson et al., "Prediction of the Rate of Decline in Cognitive Function in Alzheimer's Disease: A Model based on Simple Demographic Data and Widely Used Rating Scales" Dementia and Geriatric Disorders, vol. 15, No. 4, pp. 276-282, Sep. 2003.

Kasarskis et al., "Rating the severity of ALS by caregivers over the phone using ALSFRS-R," Amyotrophic Lateral Sclerosis & Other Motor Neuron Disorders, 2004, vol. 5, Supplement 2, p. 12.

Kasarskis et al., "Rating the severity of ALS by caregivers over the phone using ALSFRS-R," Amyotrophic Lateral Sclerosis, Mar. 2005, vol. 6, Iss. 1, pp. 50-54.

Koh et al., "Encouraging Participating in Virtual Communities", Communications of the ACM, col. 50, No. 2, Feb. 2007, pp. 69-73.

Litt et al., "Graphical Representation of Medical Information in the Visual Chart," Seventh Annual IEEE Symposium on Computer-Based Medical Systems, 1994, pp. 252-257.

Liu et al., "Towards a Rich-Context Participatory Cyberenvironment", International Workshops on Grid Computing Environments 2007, Nov. 11-12, 2007, Reno, Nevada.

Long et al., "Web Interface for the Heart Disease Program," Proceedings: AMIA Symposium, 1996, pp. 762-766.

Marquardt, "An Algorithm for Least-Squares Estimation of Nonlinear Parameters," Journal of the Society for Industrial and Applied Mathematics, Jun. 1963, vol. 11, Iss. 2, pp. 431-441.

Miller et al., "Is the ALSFRS-R Rate of Decline Linear Over Time?," Amyotrophic Lateral Sclerosis, Jan. 2007, vol. 8, Supplement 1, pp. 140-155.

Montes et al., "Development & Evaluation of self-administered version of the ALSFRS-R," Neurology, Oct. 2006, vol. 67, pp. 1294-1296.

Mould, "Developing Models of Disease Progression", Pharmacometrics: the Science of Quantitative Pharmacology Wiley, Hoboken, pp. 547-581, 2007.

(56) References Cited

OTHER PUBLICATIONS

Nielsen, "Participation Inequality: Encouraging More Users to Contribute", Participation Inequality in Social Design, Oct. 2006.

Ogura et al., "Clinical Trial of Risedronate in Japanese Volunteers: A Study on the Effects of Timing of Dosing on Absorption," Journal of Bone and Mineral Metabolism, 2004, vol. 22, pp. 120-126.

Orimo et al., "Graphical Output of Health Testing Data," Medical Informatics, 1990, vol. 15, Iss. 2, pp. 141-149.

"Pediatric Research Program Issue APS-SPR," San Diego Convention Center, San Diego, CA, May 7-11, 1995, vol. 37, No. 4 Part 2, p. 139A (Apr. 1995).

Rashid et al., "Motivating Participating by Displaying the Value of Contribution", CHI 2006, Apr. 22-27, 2006, Montreal, Quebec, Canada, pp. 955-958.

Seligman et al., "Positive Psychology Progress," American Psychologist, Jul.-Aug. 2005, pp. 410-421.

U.S. FDA, "Guideline for Industry: Dose Response Information to Support Drug Registration," U.S. FDA; Federal Register, Nov. 9, 1994, vol. 59, No. 216.

Wicks et al., "Accelerated clinical discovery using self-reported patient data collected online and a patient-matching algorithm," Nature Biotechnology, May 2011, vol. 29, No. 5, pp. 411-414.

\* cited by examiner

FIG. 1

| Condition | Number of Participants |
|---|---|
| amyotrophic.lateral.sclerosis | 111 |
| multiple.sclerosis | 105 |
| fibromyalgia | 87 |
| generalized.anxiety.disorder | 82 |
| hypothyroidism | 76 |
| systemic.lupus.erythematosus | 75 |
| osteoarthritis | 73 |
| major.depressive.disorder | 67 |
| rheumatoid.arthritis | 53 |
| high.blood.pressure..hypertension. | 49 |
| post.traumatic.stress.disorder | 46 |
| gastroesophageal.reflux.disease | 40 |
| bipolar.disorder | 38 |
| attention.deficit.hyperactivity.disorder | 31 |
| diabetes.type.2 | 29 |
| Parkinson.s.disease | 29 |
| Sjogren.s.syndrome | 29 |
| migraine | 27 |
| asthma | 25 |
| high.cholesterol..hypercholesterolemia. | 25 |
| myalgic.encephalomyelitis.chronic.fatigue.syndrome | 23 |
| none reported | 23 |
| degenerative.disc.disease | 21 |
| insomnia | 21 |
| chronic.obstructive.pulmonary.disease | 20 |
| vitamin.D.deficiency | 19 |
| osteoporosis | 15 |
| irritable.bowel.syndrome | 14 |
| Hashimoto.s.thyroiditis | 12 |
| restless.legs.syndrome | 12 |
| discoid.lupus.erythematosus | 11 |
| epilepsy | 11 |
| hiatal.hernia | 11 |
| panic.disorder | 11 |
| persistent.depressive.disorder..dysthymia. | 11 |
| sleep.apnea.disorder | 11 |
| social.anxiety.disorder | 11 |
| spinal.stenosis | 11 |

FIG. 2
FIG. 2A Random Seed 712
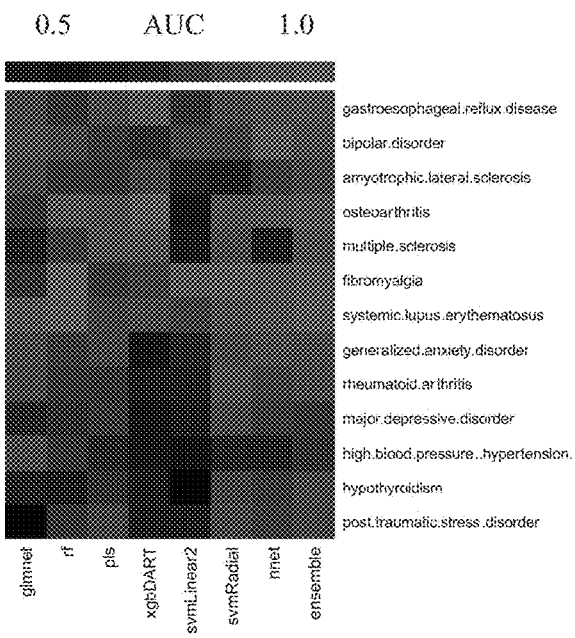
FIG. 2B Random Seed 67
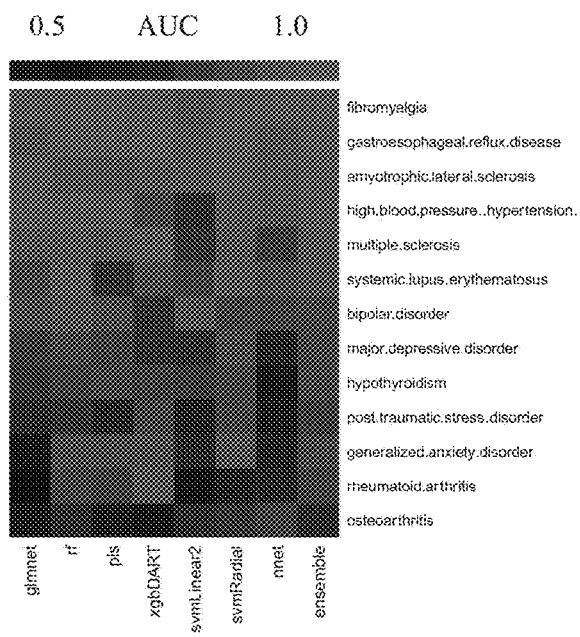
FIG. 2C Random Seed 3456
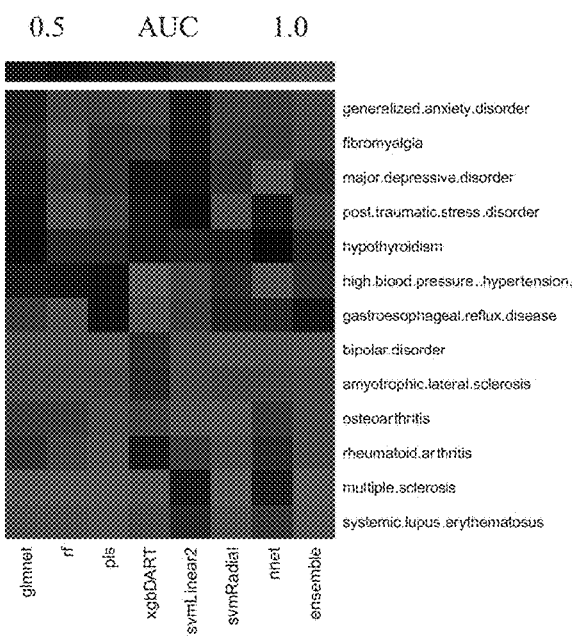

Multiple Sclerosis

Ensemble Seed
712

Ensemble Seed
67

Ensemble Seed
3456

FIG. 3D Model
Summary Score

Amyotrophic Lateral Sclerosis

Ensemble Seed
712

Ensemble Seed
67

Ensemble Seed
3456

FIG. 4D Model
Summary Score

FIG. 5
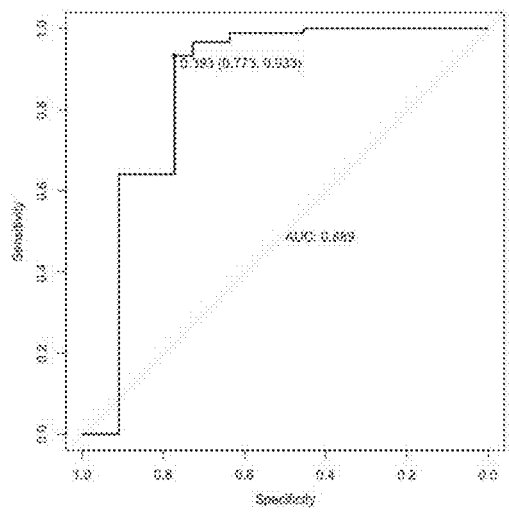
FIG. 5A amyotrophic.lateral.sclerosis
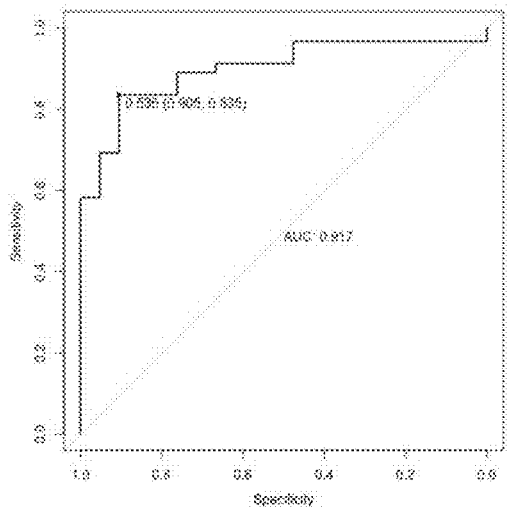
FIG. 5B multiple.sclerosis
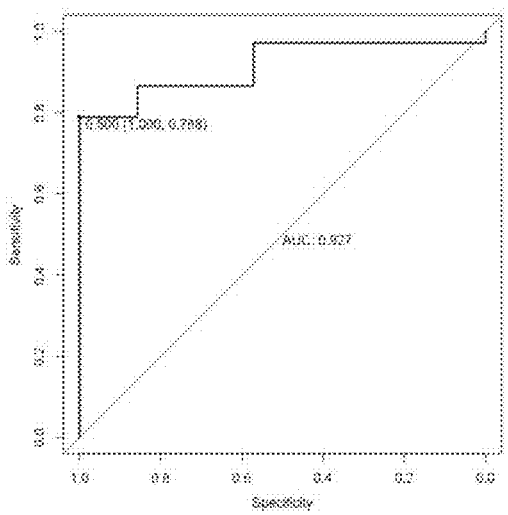
FIG. 5C bplr.dsrdr
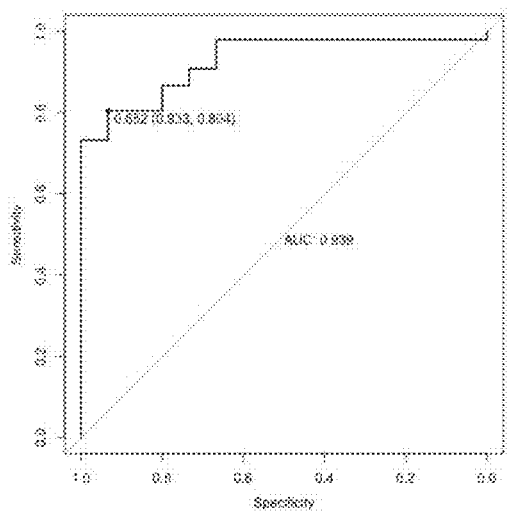
FIG. 5D systemic.lupus.erythematosus FIG. 5
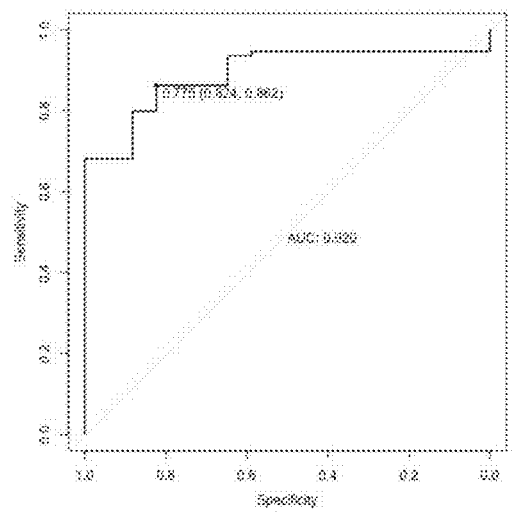
FIG. 5E fibromyalgia
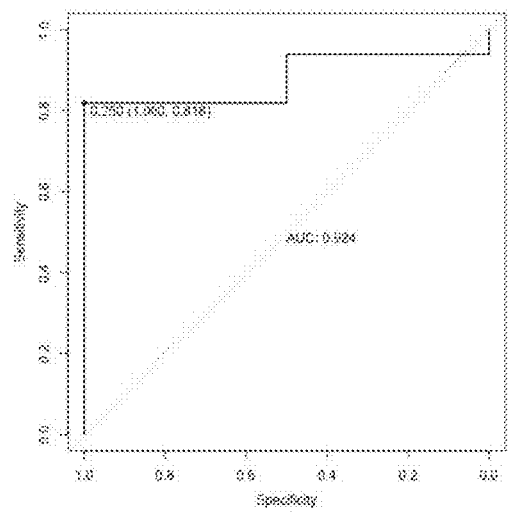
FIG. 5F generalized.anxiety.disorder
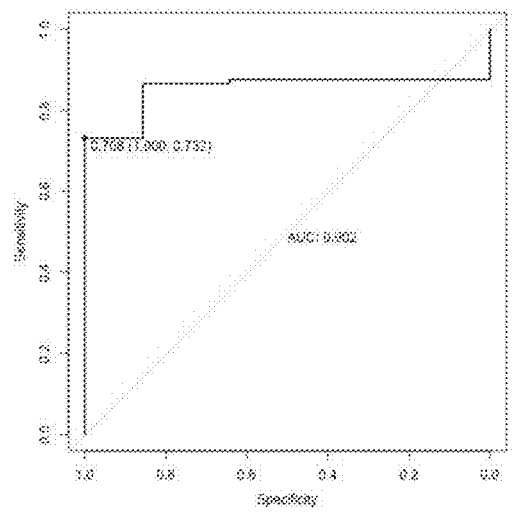
FIG. 5G osteoarthritis
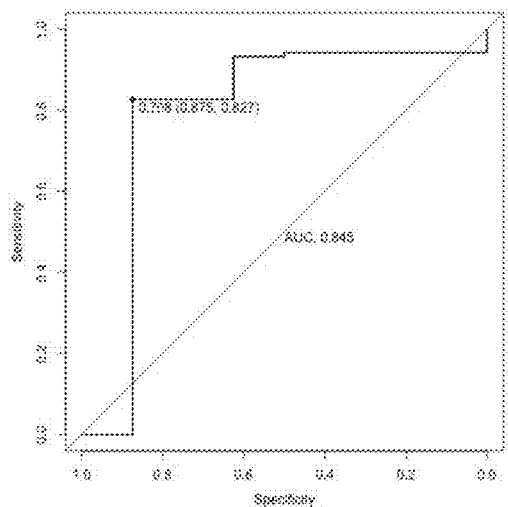
FIG. 5H gastroesophageal.reflux.disease FIG. 5
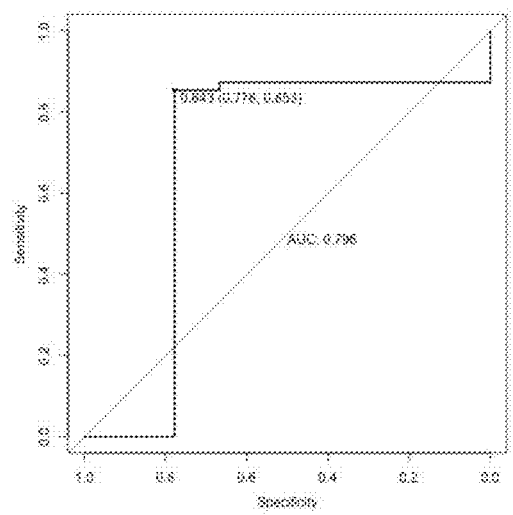
FIG. 5I hgh.bld
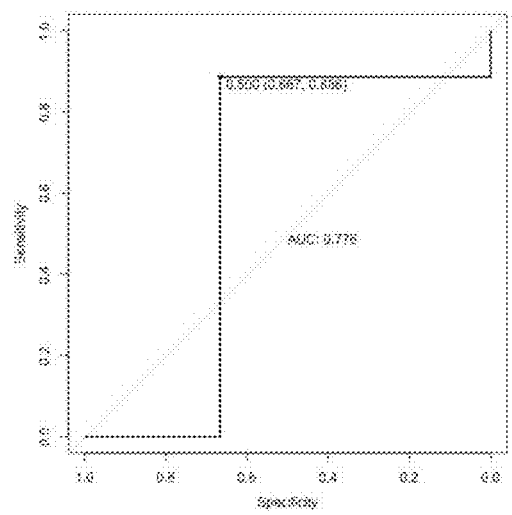
FIG. 5J major.depressive.disorder FIG. 6
FIG. 6A
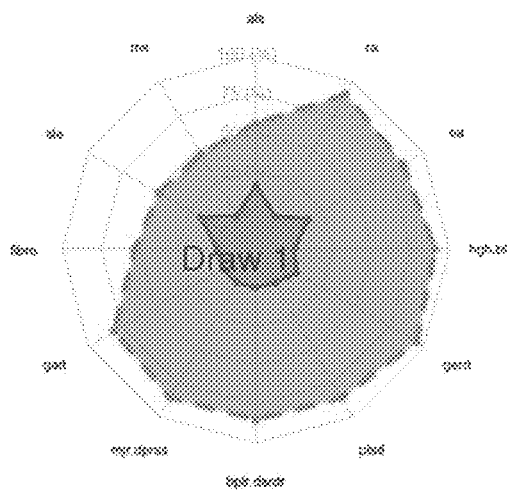
FIG. 6B
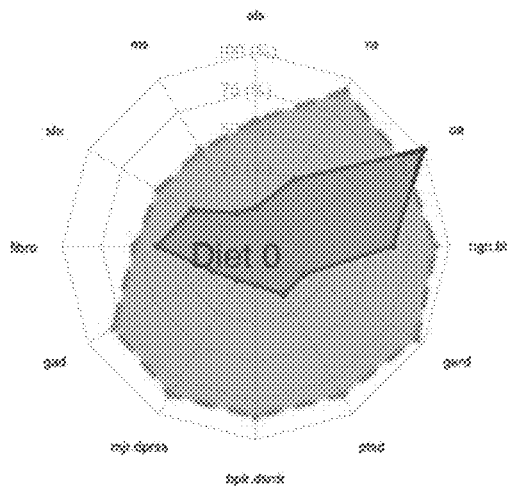

FIG. 7
FIG. 7A
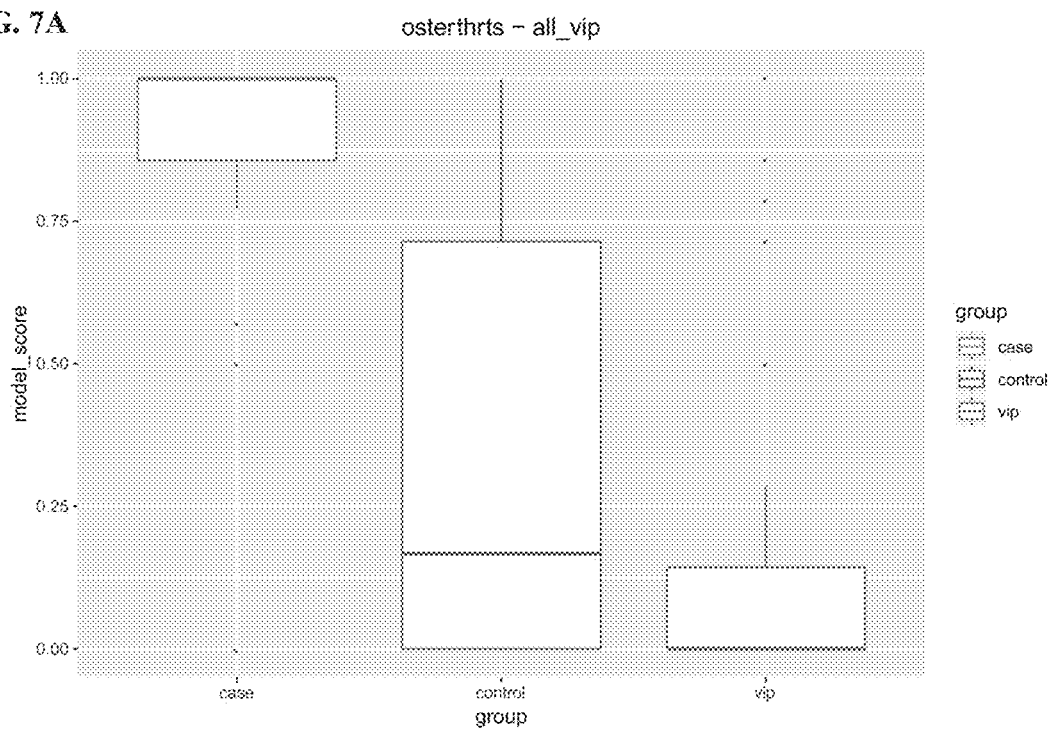
FIG. 7B
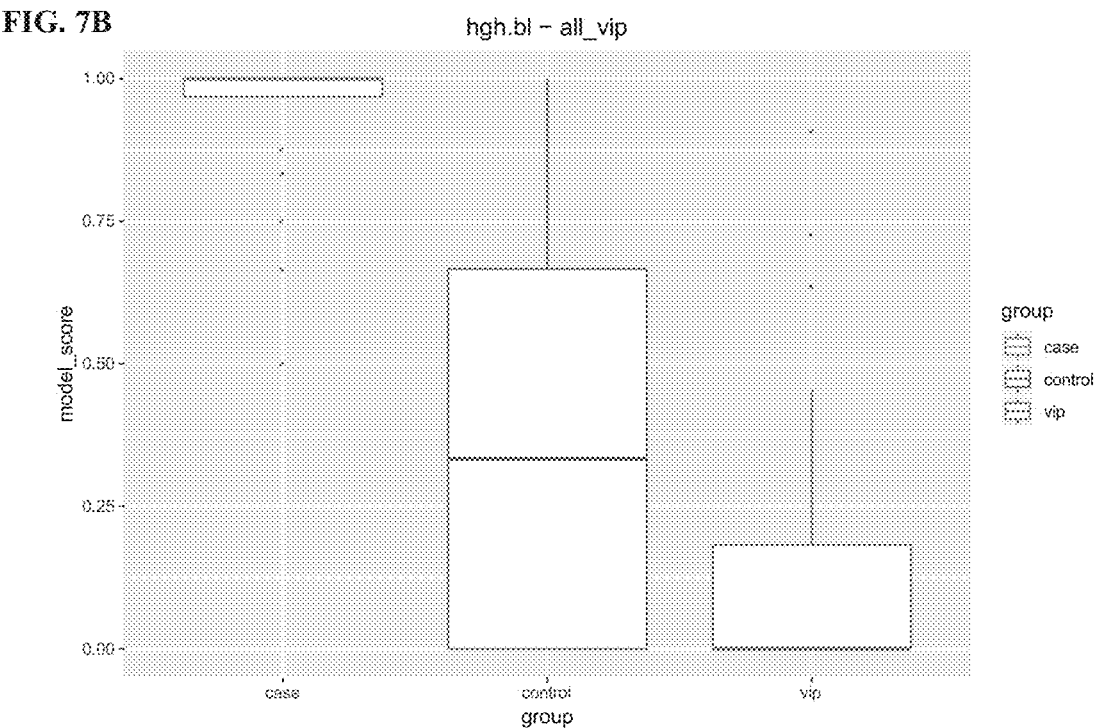

FIG. 8
FIG. 8A  Draw_vip_LM000044
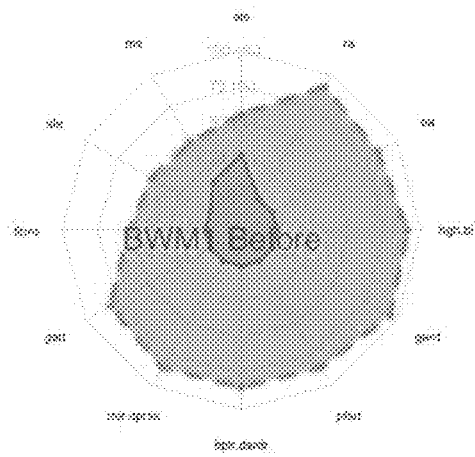
Draw_vip_LM000026
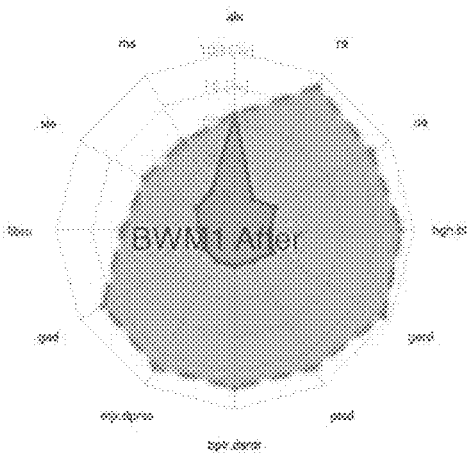
FIG. 8B  Draw_vip_LM000029
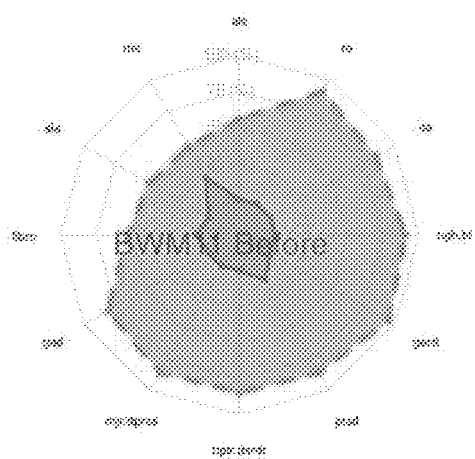
Draw_vip_LM000011
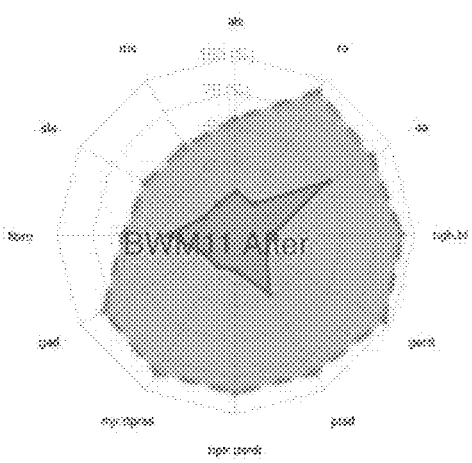

FIG. 8
FIG. 8C  Draw_vip_LM000046
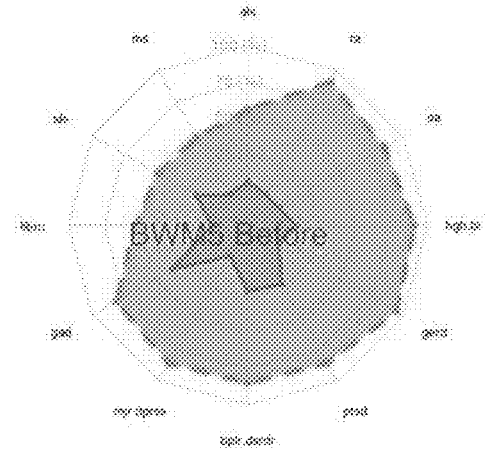
Draw_vip_LM000176
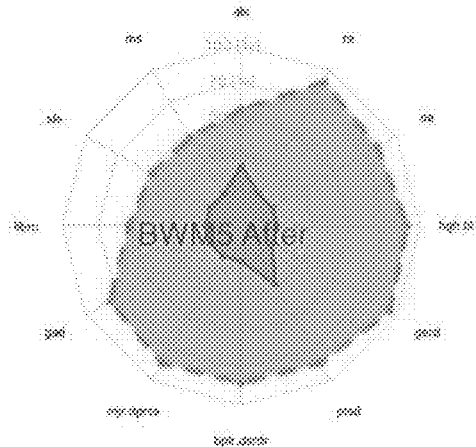
FIG. 8D  Draw_vip_LM000013
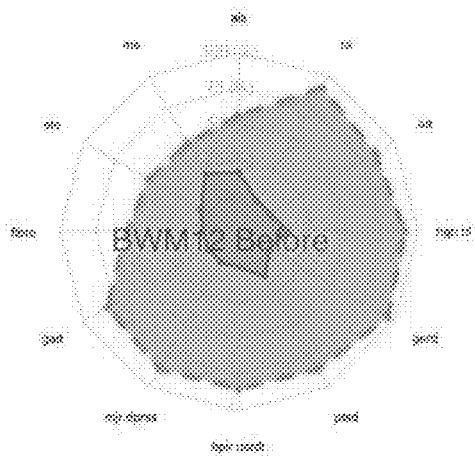
Draw_vip_LM000018
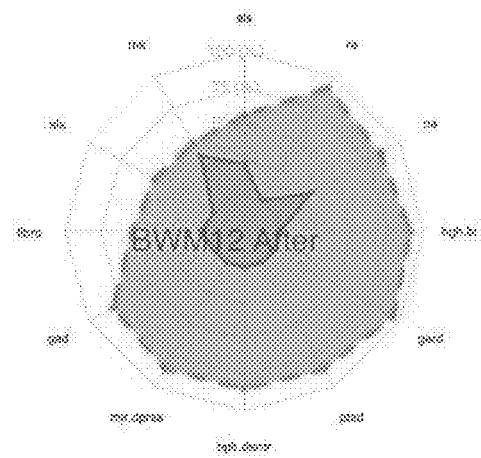

FIG. 8
FIG. 8E  Draw_vip_LM000027
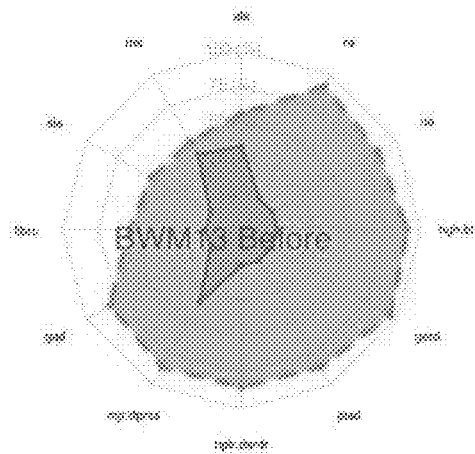
Draw_vip_LM000028
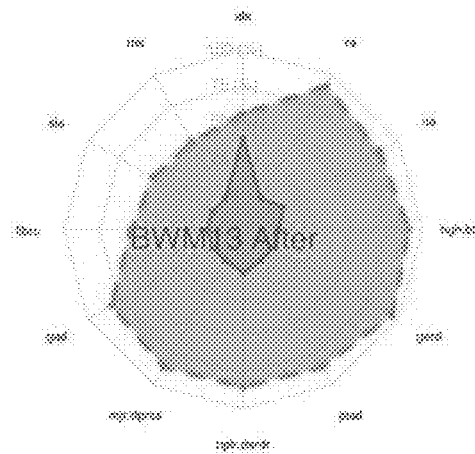
FIG. 8F  Draw_vip_LM000041
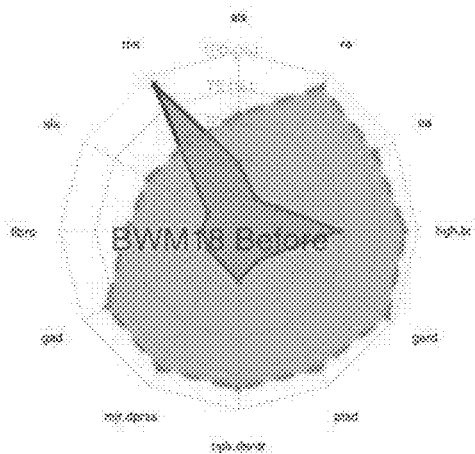
Draw_vip_LM000020
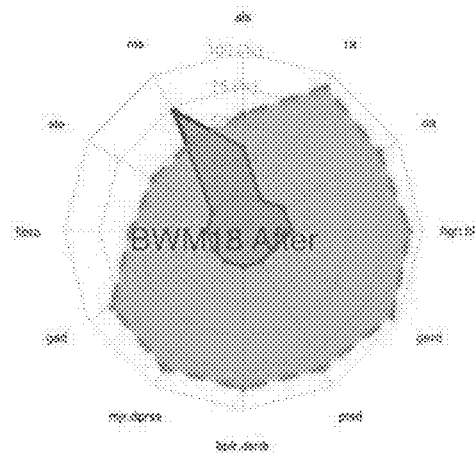

FIG. 8
FIG. 8G
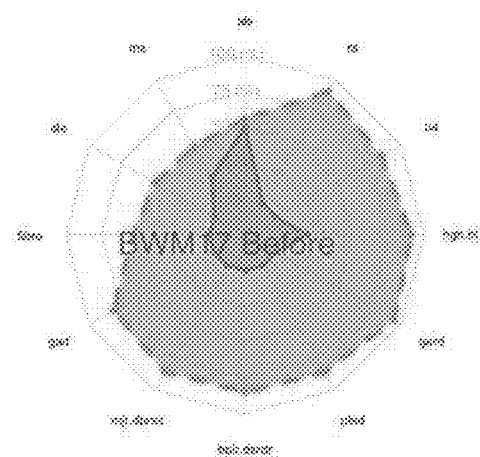 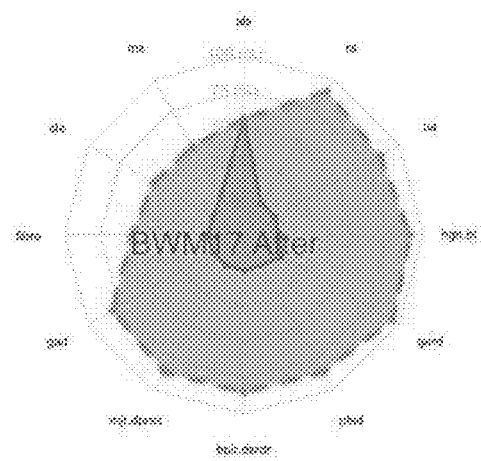

FIG. 9
FIG. 9A
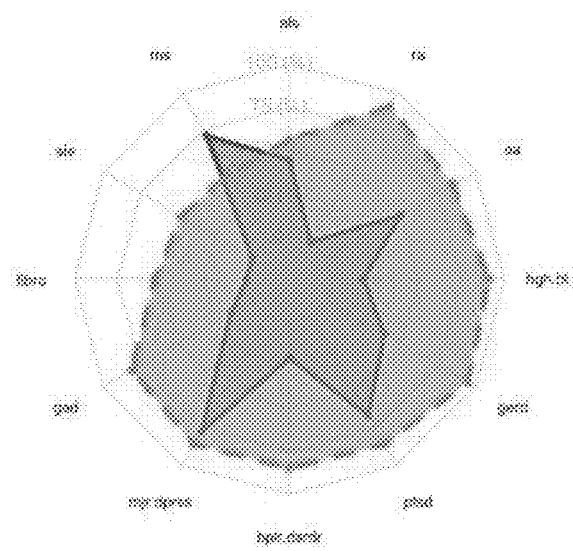
FIG. 9B
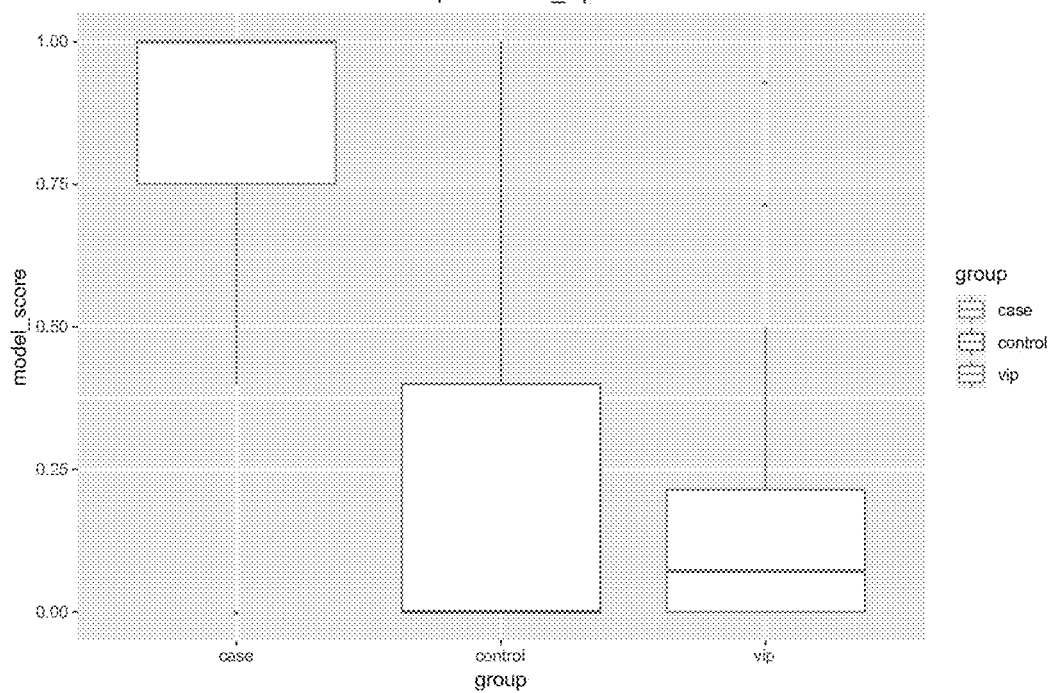

FIG. 10
FIG. 10A
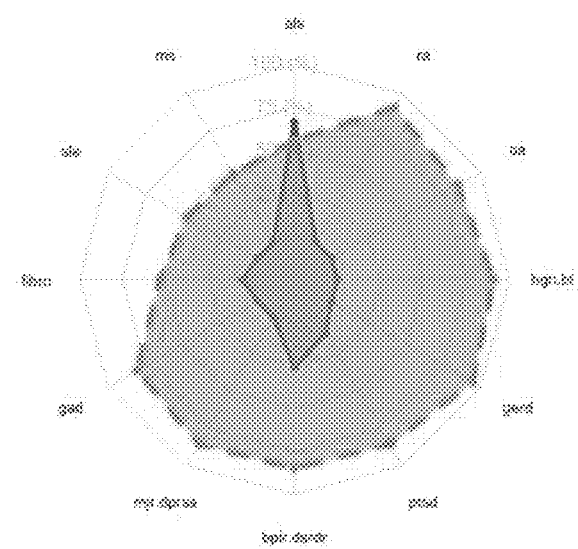
FIG. 10B
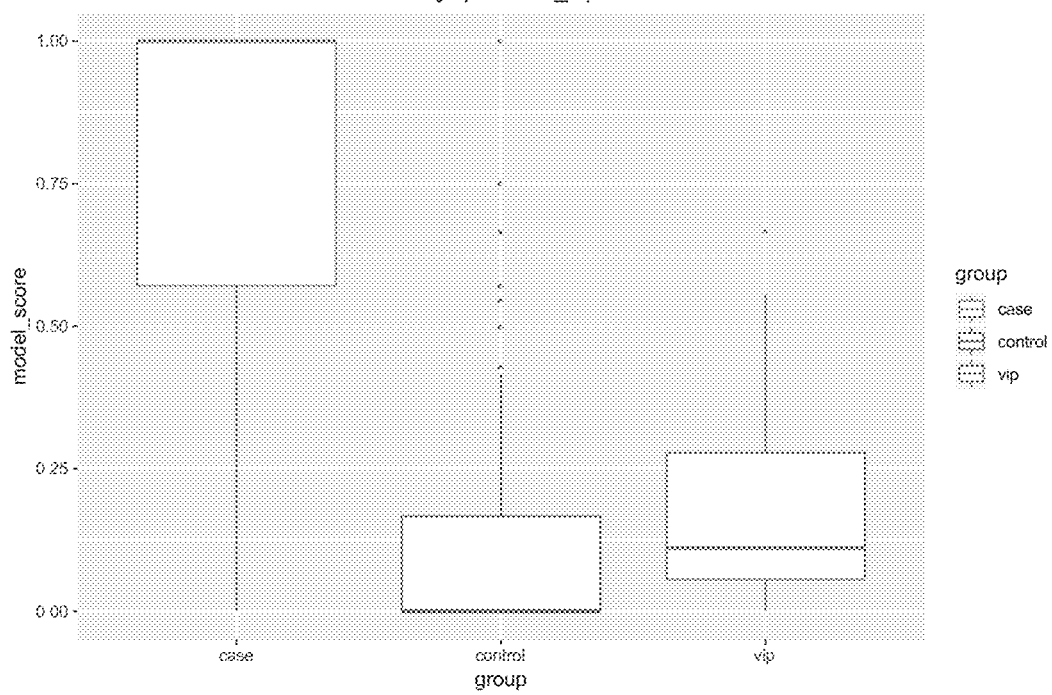

FIG. 11
Multiple Sclerosis
FIG. 11A
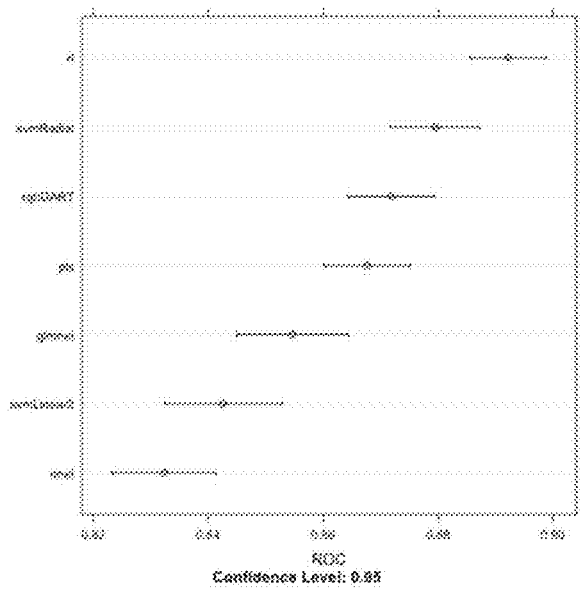
FIG. 11B
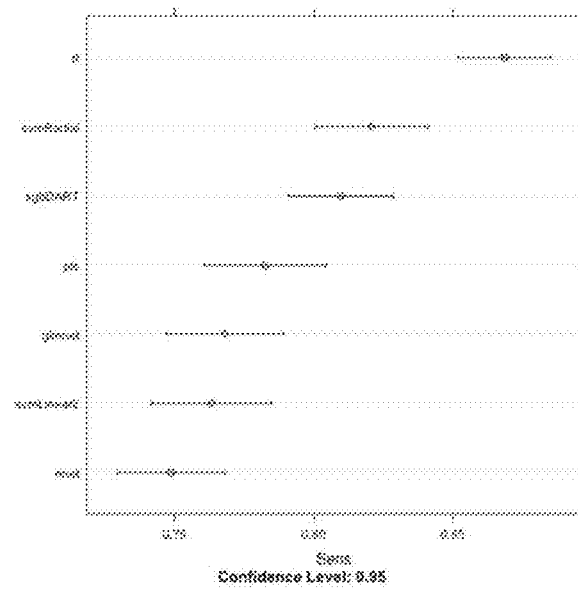
FIG. 11C
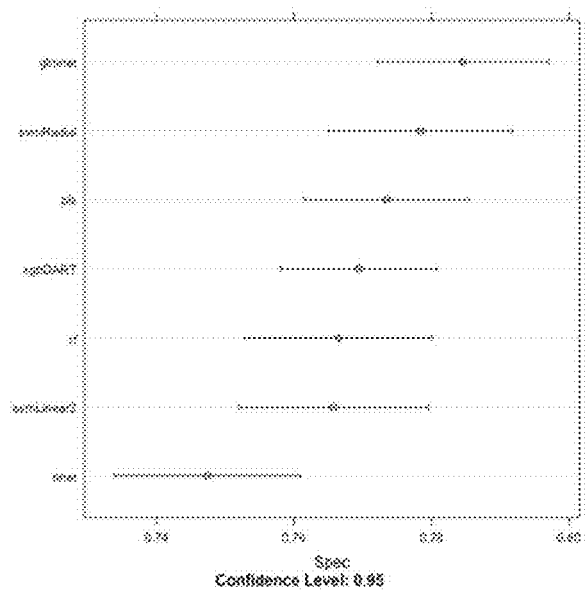

FIG. 12
Multiple Sclerosis
FIG. 12A Generalized Linear Model
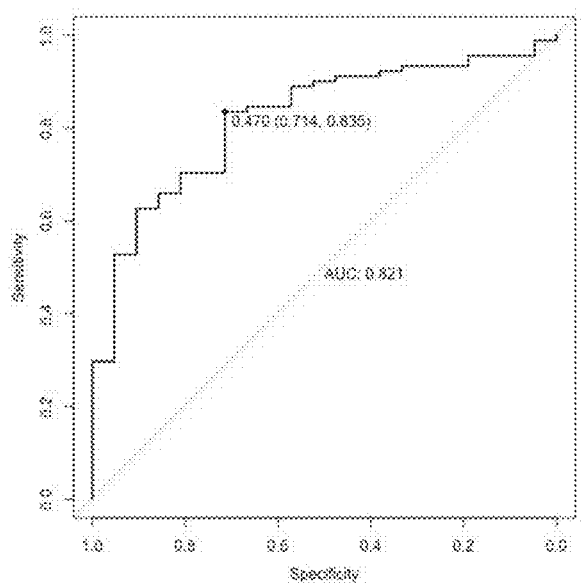
FIG. 12B Partial Least Squares
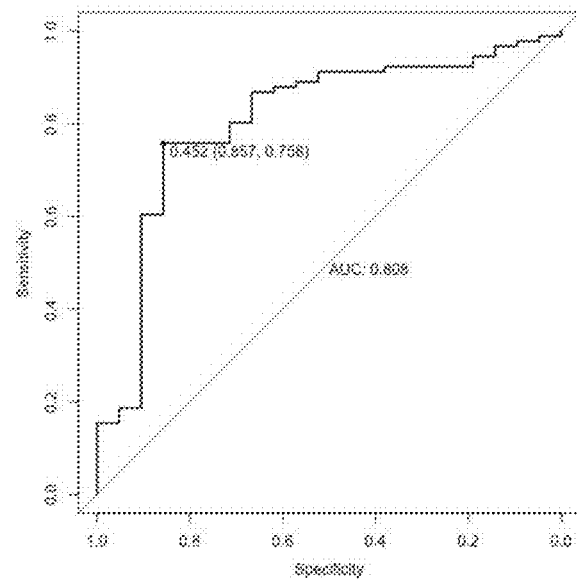
FIG. 12C Support Vector Machine
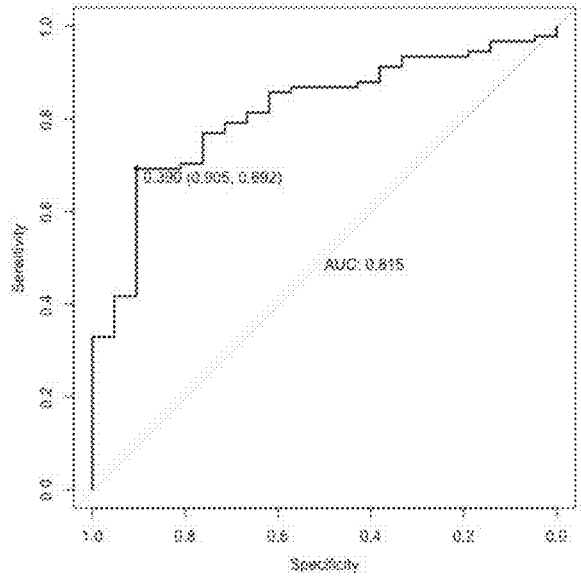
FIG. 12D Radial Kernel SVM
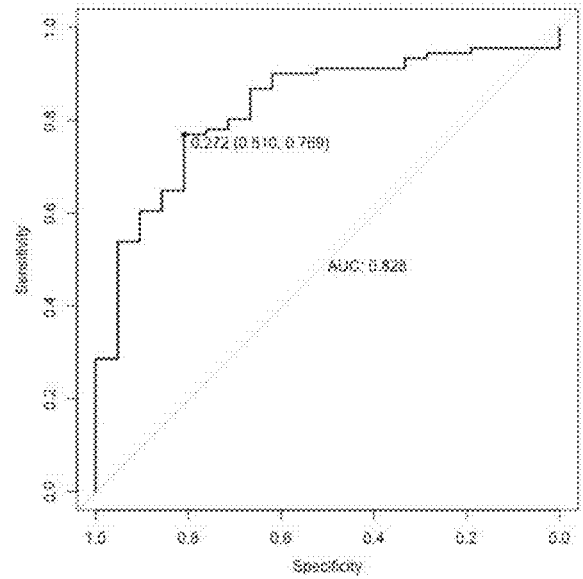

FIG. 12
Multiple Sclerosis
FIG. 12E Random Forest
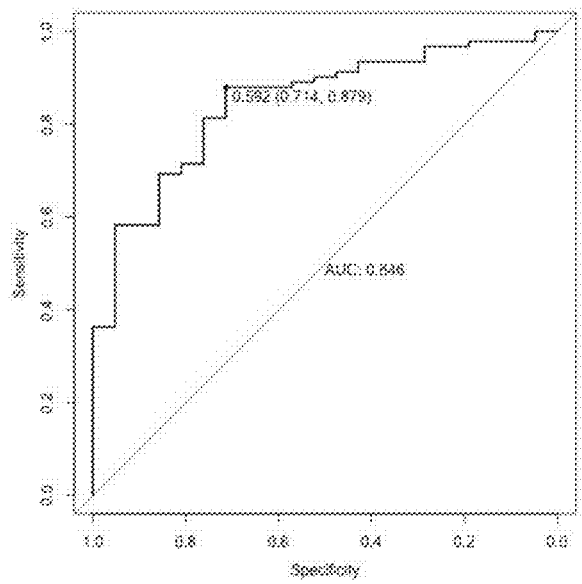
FIG. 12F Extreme Gradient Boosting
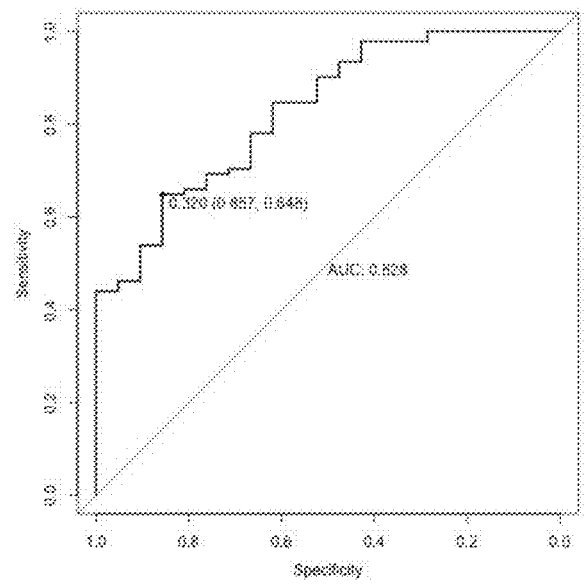
FIG. 12G Neural Network
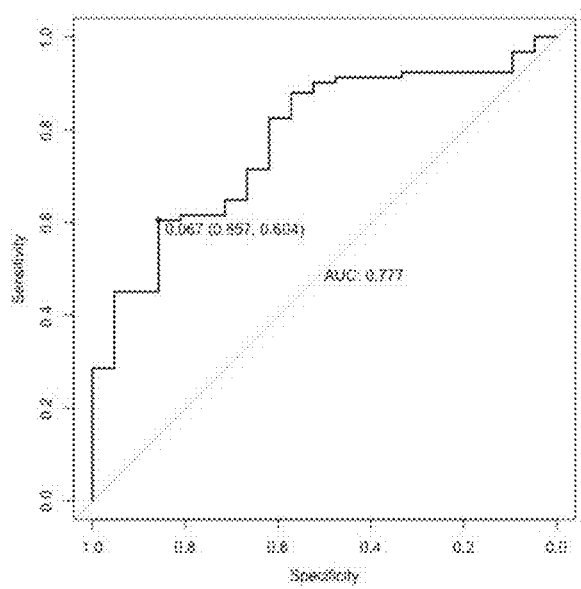
FIG. 12H Ensemble
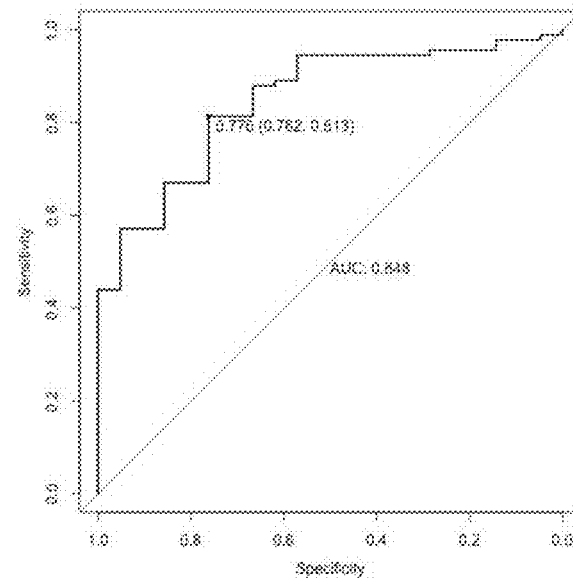

FIG. 13
FIG. 13A
Multiple Sclerosis
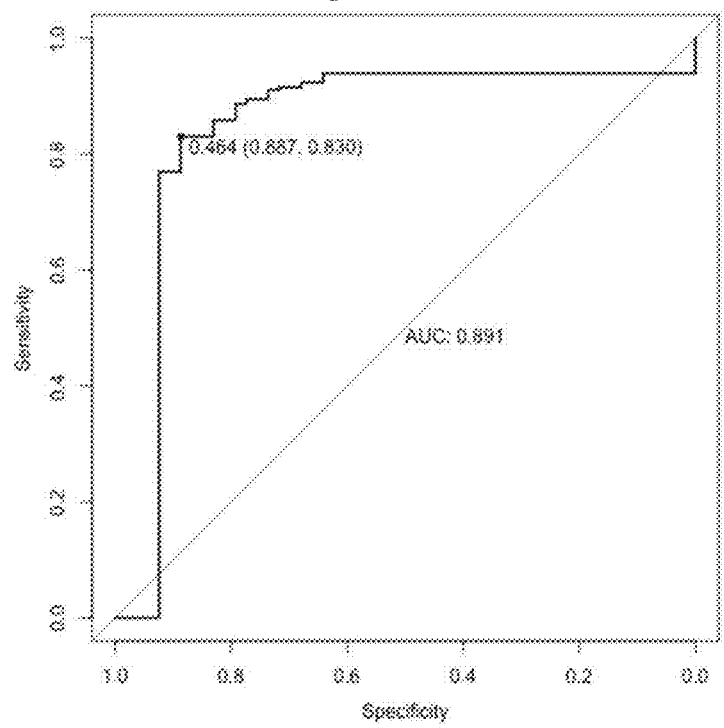
FIG. 13B
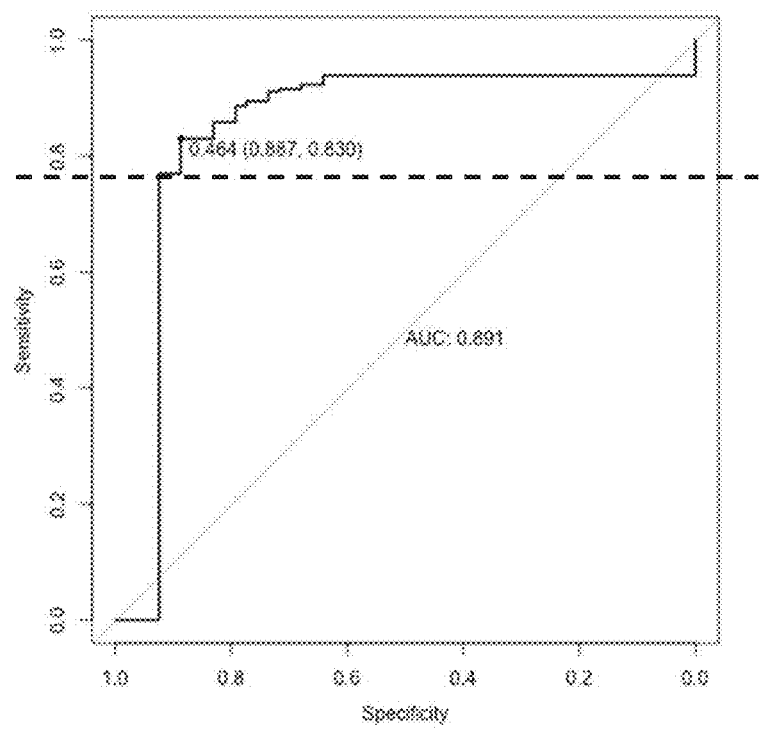

FIG. 14

| False negative participant | reported | score | call | optimal specificity | conditions | number | als | ms |
|---|---|---|---|---|---|---|---|---|
| 1 | neg | 1 | pos | pos | als | 4 | als | neg |
| 2 | neg | 1 | pos | pos | als | 1 | als | neg |
| 3 | neg | 1 | pos | pos | als | 1 | als | neg |
| 4 | neg | 1 | pos | pos | als | 2 | als | neg |
| 5 | neg | 0.8 | pos | pos | als | 1 | als | neg |
| 6 | neg | 0.75 | pos | neg | als | 1 | als | neg |
| 7 | neg | 0.75 | pos | neg | als | 1 | als | neg |
| 8 | neg | 0.75 | pos | neg | als | 1 | als | neg |
| 9 | neg | 0.6 | pos | neg | als | 1 | als | neg |
| 10 | neg | 0.6 | pos | neg | als | 1 | als | neg |
| 11 | neg | 0.56 | pos | neg | als | 1 | als | neg |
| 12 | neg | 0.5 | pos | neg | als | 1 | als | neg |
| 13 | neg | 1 | pos | pos | als_plus | 5 | als_plus | neg |
| 14 | neg | 1 | pos | pos | als_plus | 4 | als_plus | neg |
| 15 | neg | 1 | pos | pos | als_plus | 2 | als_plus | neg |
| 16 | neg | 1 | pos | pos | als_plus | 3 | als_plus | neg |
| 17 | neg | 1 | pos | pos | als_plus | 3 | als_plus | neg |
| 18 | neg | 1 | pos | pos | als_plus | 5 | als_plus | neg |
| 19 | neg | 1 | pos | pos | als_plus | 2 | als_plus | neg |
| 20 | neg | 1 | pos | pos | als_plus | 7 | als_plus | neg |
| 21 | neg | 0.9 | pos | pos | als_plus | 5 | als_plus | neg |
| 22 | neg | 0.89 | pos | pos | als_plus | 3 | als_plus | neg |
| 23 | neg | 0.8 | pos | pos | als_plus | 14 | als_plus | neg |
| 24 | neg | 0.78 | pos | pos | als_plus | 2 | als_plus | neg |
| 25 | neg | 0.75 | pos | neg | als_plus | 2 | als_plus | neg |
| 26 | neg | 0.6 | pos | neg | als_plus | 3 | als_plus | neg |
| 27 | neg | 0.6 | pos | neg | als_plus | 3 | als_plus | neg |
| 28 | neg | 0.5 | pos | neg | als_plus | 2 | als_plus | neg |
| 29 | neg | 1 | pos | pos | fibro | 1 | neg | neg |
| 30 | neg | 1 | pos | pos | asthma | 4 | neg | neg |
| 31 | neg | 1 | pos | pos | wow | 15 | neg | neg |
| 32 | neg | 0.9 | pos | pos | wow | 18 | neg | neg |
| 33 | neg | 0.6 | pos | neg | ra | 1 | neg | neg |
| 34 | neg | 0.6 | pos | neg | wow | 10 | neg | neg |
| 35 | neg | 0.6 | pos | neg | fibro_pd | 3 | neg | neg |
| 36 | neg | 0.5 | pos | neg | wow | 5 | neg | neg |
| 37 | neg | 0.5 | pos | neg | wow | 8 | neg | neg |
| 38 | neg | 0.5 | pos | neg | wow | 10 | neg | neg |

FIG. 15A

| # | probe | symbol | SUPER_PATHWAY | SUB_PATHWAY |
|---|---|---|---|---|
| 1 | mlon_32458 | oleamide | Lipid | Fatty Acid, Amide |
| 2 | mlon_42095 | palmitamide (16:0) | Lipid | Fatty Acid, Amide |
| 3 | mlon_57449 | stearoyl-arachidonoyl-glycerol (18:0/20:4) [2]* | Lipid | Diacylglycerol |
| 4 | mlon_38165 | palmitoyl ethanolamide | Lipid | Endocannabinoid |
| 5 | mlon_47898 | 1-pentadecanoylglycerol (15:0) | Lipid | Monoacylglycerol |
| 6 | mlon_34258 | 2-docosahexaenoyl-GPE (22:6)* | Lipid | Lysophospholipid |
| 7 | mlon_43258 | acisoga | Amino Acid | Polyamine Metabolism |
| 8 | mlon_53031 | methylsuccinoylcarnitine | Amino Acid | Leucine, Isoleucine and Valine Metabolism |
| 9 | mlon_38102 | oleoyl ethanolamide | Lipid | Endocannabinoid |
| 10 | mlon_48258 | 1-oleoyl-GPC (18:1) | Lipid | Lysophospholipid |
| 11 | mlon_40062 | 4-hydroxy-2-oxoglutaric acid | Lipid | Fatty Acid, Dicarboxylate |
| 12 | mlon_554 | adenine | Nucleotide | Purine Metabolism, Adenine containing |
| 13 | mlon_33936 | octanoylcarnitine (C8) | Lipid | Fatty Acid Metabolism(Acyl Carnitine) |
| 14 | mlon_35665 | N-acetyl-aspartyl-glutamate (NAAG) | Amino Acid | Glutamate Metabolism |
| 15 | mlon_52701 | 1-(1-enyl-oleoyl)-GPC (P-18:1)* | Lipid | Lysoplasmalogen |
| 16 | mlon_43493 | formiminoglutamate | Amino Acid | Histidine Metabolism |
| 17 | mlon_52699 | 1-stearoyl-2-docosapentaenoyl-GPC (18:0/22:5n3)* | Lipid | Phosphatidylcholine (PC) |
| 18 | mlon_48182 | myristoleoylcarnitine (C14:1)* | Lipid | Fatty Acid Metabolism(Acyl Carnitine) |
| 19 | mlon_57603 | 1-nervonoyl-2-arachidonoyl-GPC (24:1/20:4)* | Lipid | Phosphatidylcholine (PC) |
| 20 | mlon_33941 | decanoylcarnitine (C10) | Lipid | Fatty Acid Metabolism(Acyl Carnitine) |
| 21 | mlon_36713 | N6-carboxymethyllysine | Carbohydrate | Advanced Glycation End-product |
| 22 | mlon_38116 | indole-3-carboxylate | Amino Acid | Tryptophan Metabolism |
| 23 | mlon_33939 | N-acetylthreonine | Amino Acid | Glycine, Serine and Threonine Metabolism |
| 24 | mlon_57415 | 1-palmitoyl-2-(hydroxylinoleoyl)-GPC (16:0/18:2(OH))* | Lipid | Phosphatidylcholine (PC) |
| 25 | mlon_34534 | laurylcarnitine (C12) | Lipid | Fatty Acid Metabolism(Acyl Carnitine) |

FIG. 15B

Feature importance by model

| # | GLM | RF | PLS | xgbDART |
|---|---|---|---|---|
| 1 | 6.67038855 | 100 | 100 | 100 |
| 2 | 90.22831036 | 69.5508659 | 77.736725 | 39.12393992 |
| 3 | 32.98502647 | 29.6773241 | 63.8500335 | 34.70632458 |
| 4 | 43.58401525 | 28.7757016 | 72.7177502 | 27.15277805 |
| 5 | 25.04280754 | 33.2334371 | 69.1955832 | 21.43428083 |
| 6 | 80.64114814 | 75.5612693 | 39.5709124 | 20.35906529 |
| 7 | 65.30102333 | 47.8546802 | 95.4128898 | 14.32749231 |
| 8 | 99.36643059 | 59.0092317 | 34.1736094 | 12.23676876 |
| 9 | 0 | 36.7367013 | 67.2579194 | 11.28370419 |
| 10 | 5.097632113 | 24.3549277 | 37.3442865 | 11.03901785 |
| 11 | 43.36424197 | 37.1533153 | 59.6929145 | 6.264445796 |
| 12 | 100 | 25.5323349 | 66.2075326 | 6.199940961 |
| 13 | 32.19796095 | 14.219048 | 46.2090817 | 5.440936133 |
| 14 | 13.13005001 | 16.6711095 | 58.2090908 | 5.410615588 |
| 15 | 49.73049323 | 2.4730164 | 29.5958629 | 4.315258162 |
| 16 | 16.0612265 | 7.34973514 | 57.2116615 | 4.130000411 |
| 17 | 30.70785651 | 19.9579441 | 28.3604068 | 2.881790519 |
| 18 | 1.374936037 | 10.0416453 | 38.6199353 | 1.409029801 |
| 19 | 9.763322139 | 12.2539229 | 45.2538031 | 0 |
| 20 | 6.185607416 | 16.3215439 | 40.0005071 | 0 |
| 21 | 57.77992127 | 45.3075094 | 48.2066622 | 0 |
| 22 | 30.84085761 | 14.3240633 | 45.7021228 | 0 |
| 23 | 39.3367534 | 30.6550474 | 54.1249473 | 0 |
| 24 | 88.22402195 | 21.7508736 | 51.0257524 | 0 |
| 25 | 7.735421488 | 14.1393318 | 30.7346879 | 0 |

FIG. 16

| Generic Treatment Name | Count (out of 564 total) | Percent |
|---|---|---|
| Glatiramer acetate | 244 | 43% |
| Interferon beta-1a IM Injection | 145 | 26% |
| Dimethyl fumarate | 127 | 23% |
| Interferon beta-1a SubQ injection | 114 | 20% |
| Natalizumab | 100 | 18% |
| Interferon beta-1b SubQ Injection | 84 | 15% |
| Fingolimod | 74 | 13% |
| Copaxone | 67 | 12% |
| Baclofen | 51 | 9% |
| Teriflunomide | 49 | 9% |
| Tysabri | 37 | 7% |
| Rebif | 36 | 6% |
| Tecfidera | 31 | 5% |
| Ocrelizumab | 29 | 5% |
| Vitamin D | 28 | 5% |
| Modafinil | 24 | 4% |
| Betaseron | 24 | 4% |
| Aubagio | 22 | 4% |
| Ampyra | 18 | 3% |
| Ocrevus | 17 | 3% |
| Vitamin D3 (cholecalciferol) | 17 | 3% |
| Avonex | 16 | 3% |
| Dalfampridine | 16 | 3% |
| Alemtuzumab | 14 | 2% |
| Provigil | 13 | 2% |
| Avonex Prefilled Syringe | 13 | 2% |
| Peginterferon beta-1a | 12 | 2% |
| Gilenya | 10 | 2% |
| Solu-Medrol Infusion | 9 | 2% |
| Omega 3 Fish Oil | 9 | 2% |

FIG. 17A

| # | probe | symbol | SUPER_PATHWAY | SUB_PATHWAY |
|---|---|---|---|---|
| 1 | mlon_32458 | oleamide | Lipid | Fatty Acid, Amide |
| 2 | mlon_42095 | palmitamide (16:0) | Lipid | Fatty Acid, Amide |
| 3 | mlon_57449 | stearoyl-arachidonoyl-glycerol (18:0/20:4) [2]* | Lipid | Diacylglycerol |
| 4 | mlon_38165 | palmitoyl ethanolamide | Lipid | Endocannabinoid |
| 5 | mlon_47898 | 1-pentadecanoylglycerol (15:0) | Lipid | Monoacylglycerol |
| 6 | mlon_34258 | 2-docosahexaenoyl-GPE (22:6)* | Lipid | Lysophospholipid |
| 7 | mlon_43258 | acisoga | Amino Acid | Polyamine Metabolism |
| 8 | mlon_53031 | methylsuccinoylcarnitine | Amino Acid | Leucine, Isoleucine and Valine Metabolism |
| 9 | mlon_38102 | oleoyl ethanolamide | Lipid | Endocannabinoid |
| 10 | mlon_48258 | 1-oleoyl-GPC (18:1) | Lipid | Lysophospholipid |
| 11 | mlon_40062 | 4-hydroxy-2-oxoglutaric acid | Lipid | Fatty Acid, Dicarboxylate |
| 12 | mlon_554 | adenine | Nucleotide | Purine Metabolism, Adenine containing |
| 13 | mlon_33936 | octanoylcarnitine (C8) | Lipid | Fatty Acid Metabolism(Acyl Carnitine) |
| 14 | mlon_35665 | N-acetyl-aspartyl-glutamate (NAAG) | Amino Acid | Glutamate Metabolism |
| 15 | mlon_52701 | 1-(1-enyl-oleoyl)-GPC (P-18:1)* | Lipid | Lysoplasmalogen |
| 16 | mlon_43493 | formiminoglutamate | Amino Acid | Histidine Metabolism |
| 17 | mlon_22138 | homocitrulline | Amino Acid | Urea cycle; Arginine and Proline Metabolism |
| 18 | mlon_52699 | 1-stearoyl-2-docosapentaenoyl-GPC (18:0/22:5n3)* | Lipid | Phosphatidylcholine (PC) |
| 19 | mlon_48182 | myristoleoylcarnitine (C14:1)* | Lipid | Fatty Acid Metabolism(Acyl Carnitine) |
| 20 | mlon_57603 | 1-nervonoyl-2-arachidonoyl-GPC (24:1/20:4)* | Lipid | Phosphatidylcholine (PC) |
| 21 | mlon_33941 | decanoylcarnitine (C10) | Lipid | Fatty Acid Metabolism(Acyl Carnitine) |
| 22 | mlon_36713 | N6-carboxymethyllysine | Carbohydrate | Advanced Glycation End-product |
| 23 | mlon_38116 | indole-3-carboxylate | Amino Acid | Tryptophan Metabolism |
| 24 | mlon_33442 | pseudouridine | Nucleotide | Pyrimidine Metabolism, Uracil containing |
| 25 | mlon_1123 | inosine | Nucleotide | Purine Metabolism, (Hypo)Xanthine/Inosine containing |
| 26 | mlon_33939 | N-acetylthreonine | Amino Acid | Glycine, Serine and Threonine Metabolism |
| 27 | mlon_57415 | 1-palmitoyl-2-(hydroxylinoleoyl)-GPC (16:0/18:2(OH))* | Lipid | Phosphatidylcholine (PC) |

FIG. 17B

| # | logFC (MS+ vs. MS-) | adj.P.Val (MS+ vs. MS-) | Drugbank entry | Supplements |
|---|---|---|---|---|
| 1 | -0.6097741 | 1.55E-05 | No entry | yes |
| 2 | -0.5362691 | 0.00030673 | No entry | yes |
| 3 | 0.47845089 | 0.00268462 | No entry | no |
| 4 | 0.46785923 | 0.00268462 | No entry | yes |
| 5 | 0.46640355 | 0.00268462 | No entry | no |
| 6 | 0.45135258 | 0.00412944 | No entry | no |
| 7 | 0.4452364 | 0.00451695 | No entry | no |
| 8 | 0.43017555 | 0.00711294 | No entry | no |
| 9 | 0.41571207 | 0.01092735 | No entry | yes |
| 10 | 0.40573118 | 0.01420635 | No entry | no |
| 11 | 0.36892242 | 0.04427973 | No entry | no |
| 12 | -0.3679785 | 0.04427973 | No entry | yes |
| 13 | 0.36134446 | 0.04936957 | No entry | no |
| 14 | 0.36004009 | 0.04936957 | No entry | no |
| 15 | 0.35671343 | 0.05136986 | No entry | no |
| 16 | -0.3476418 | 0.05687071 | No entry | no |
| 17 | 0.34695124 | 0.05687071 | Increases homocitrulline: Amiloride, Atenolol, | yes |
| 18 | 0.34657234 | 0.05687071 | No entry | no |
| 19 | 0.3458631 | 0.05687071 | No entry | no |
| 20 | 0.34456969 | 0.05687071 | No entry | no |
| 21 | 0.34300459 | 0.05690202 | No entry | no |
| 22 | -0.3399248 | 0.05982 | No entry | no |
| 23 | 0.33338203 | 0.07006863 | No entry | yes |
| 24 | 0.32302723 | 0.08897185 | Increases pseudouridine: Amiloride, | yes |
| 25 | -0.3219862 | 0.08897185 | Aspirin increases inosine | yes |
| 26 | 0.32142236 | 0.08897185 | No entry | yes |
| 27 | -0.3200811 | 0.08897185 | No entry | no |

FIG. 18
FIG. 18A With Supplements – AUC performance
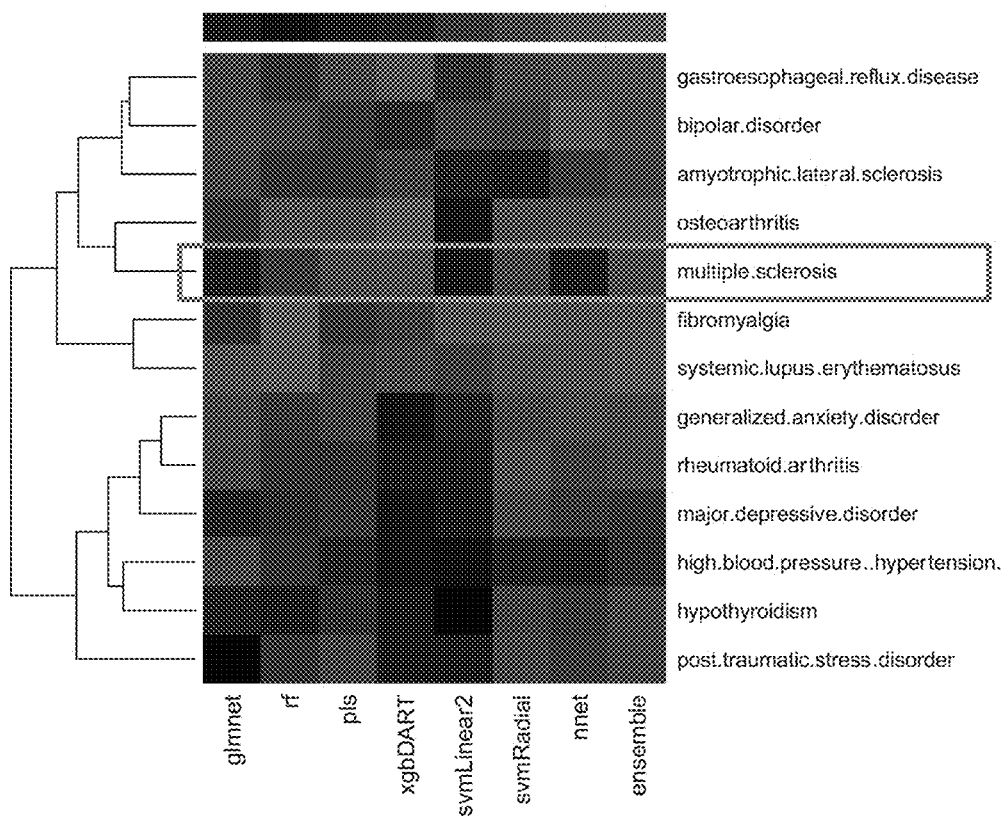
FIG. 18B MS Ensemble AUC = 0.866
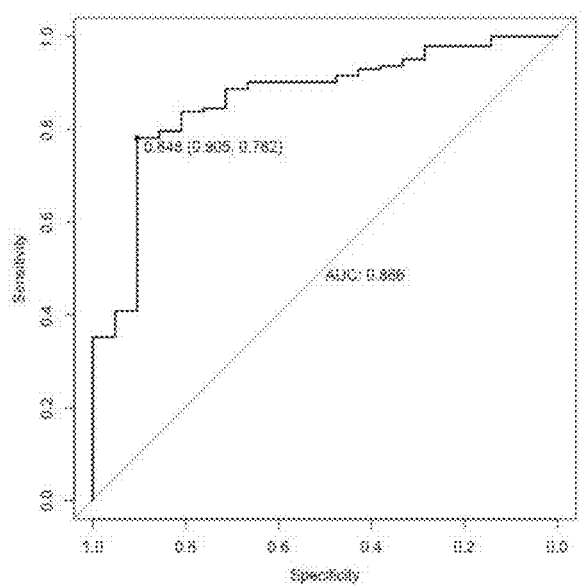

FIG. 18
FIG. 18C No Supplements – AUC performance
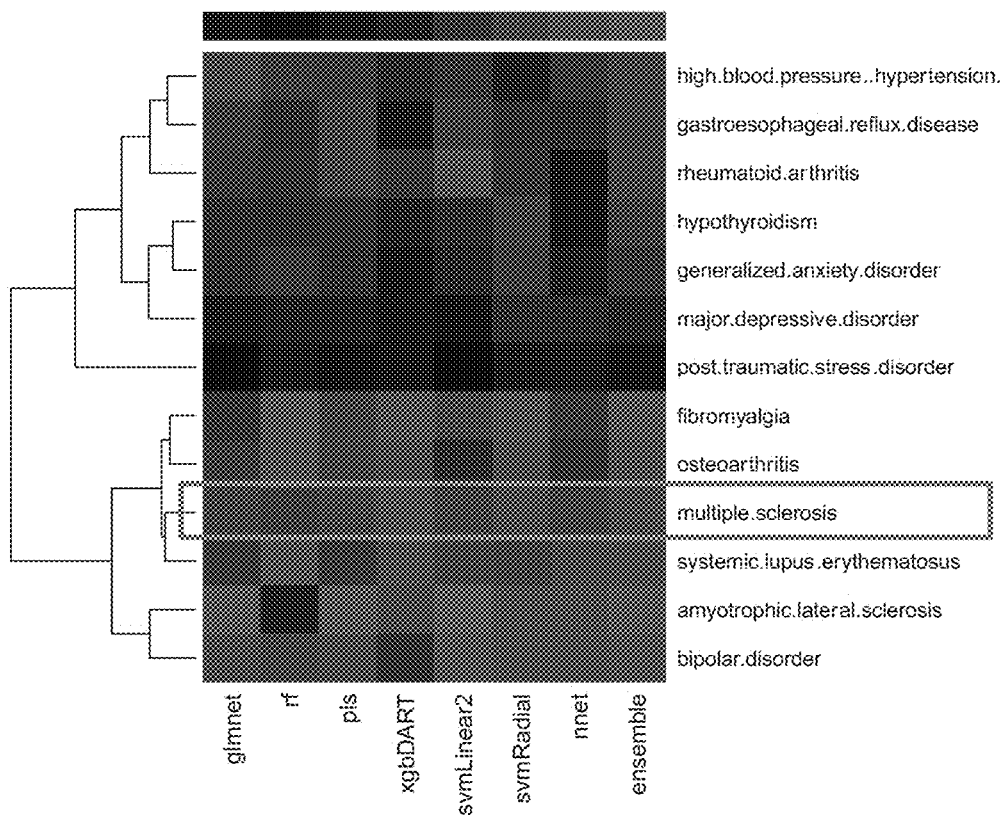
FIG. 18D MS Ensemble AUC = 0.845
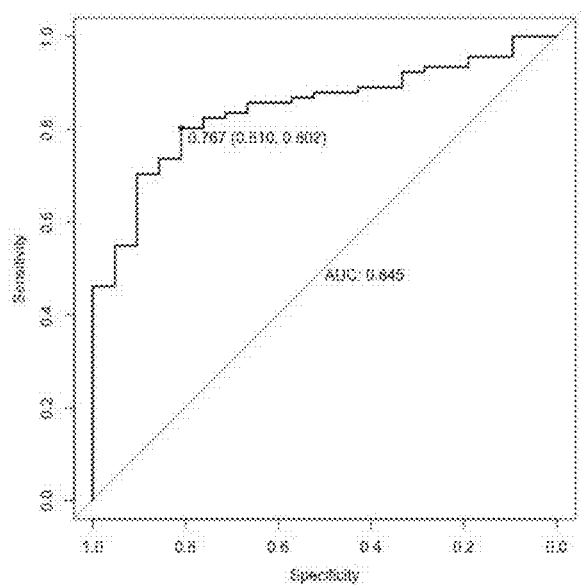

FIG. 19
Amyotrophic Lateral Sclerosis
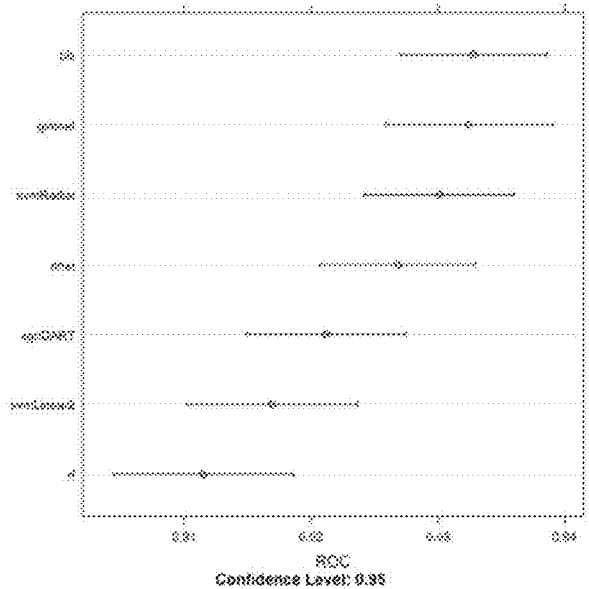
FIG. 19A
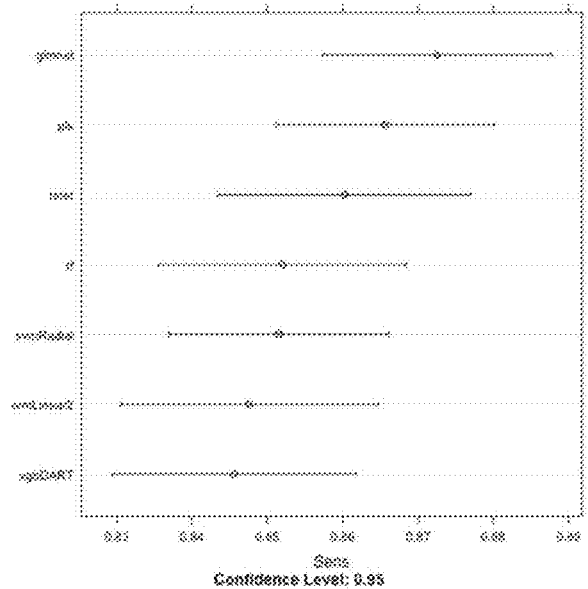
FIG. 19B
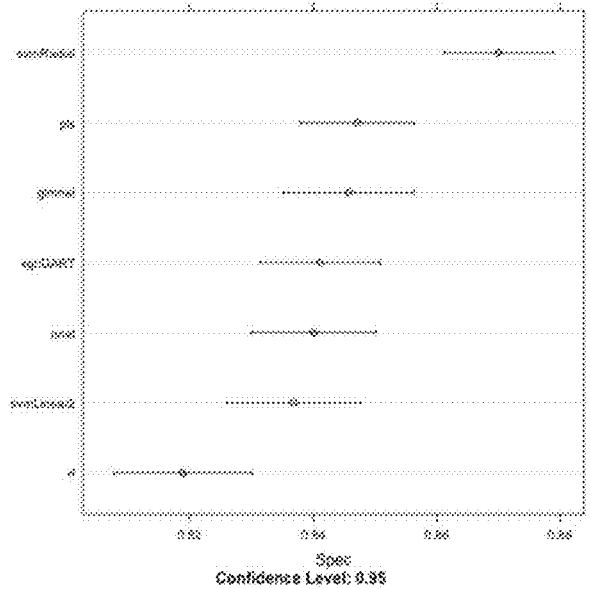
FIG. 19C

FIG. 20
Amyotrophic Lateral Sclerosis
FIG. 20A Generalized Linear Model
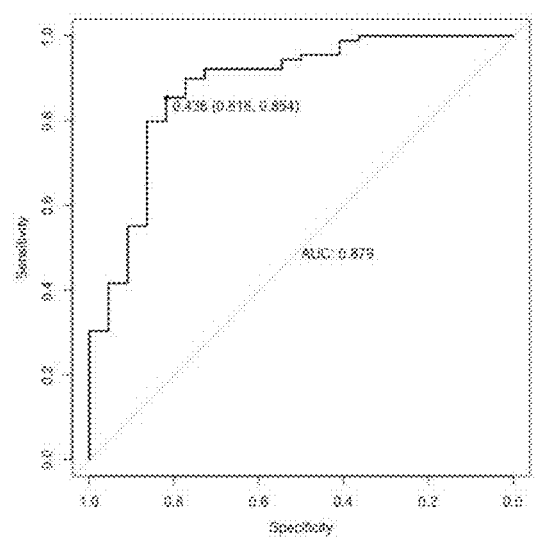
FIG. 20B Partial Least Squares
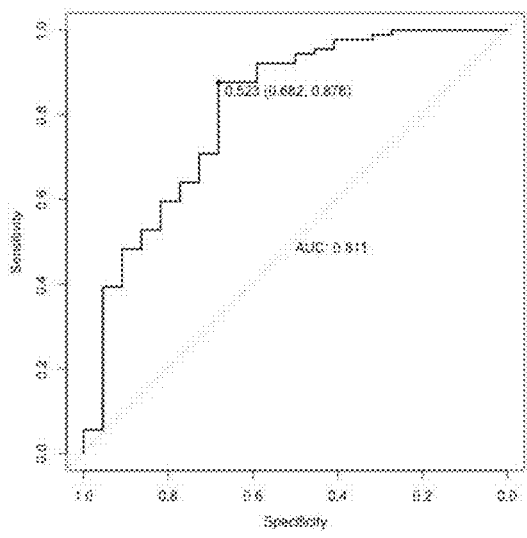
FIG. 20C Support Vector Machine
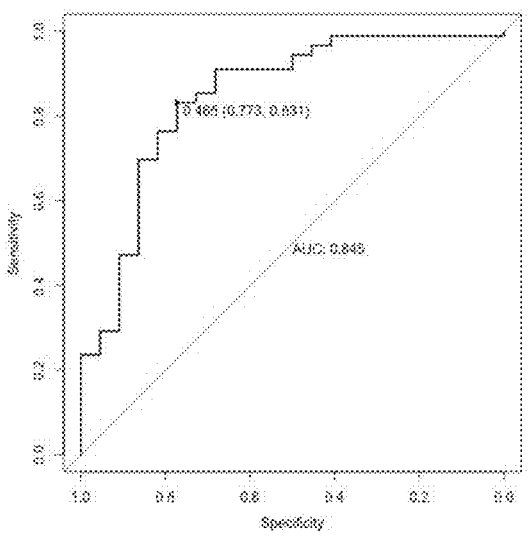
FIG. 20D SVMR
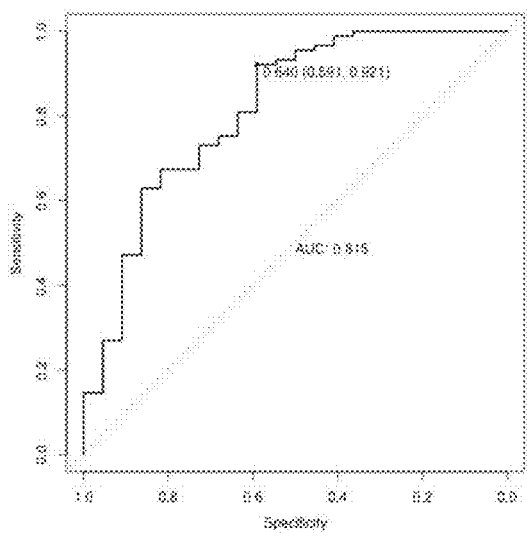

FIG. 20
Amyotrophic Lateral Sclerosis
FIG. 20E Random Forest
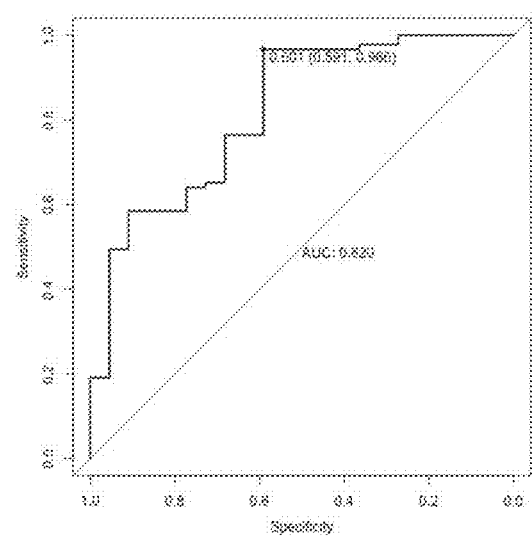
FIG. 20F Extreme Gradient Boosting
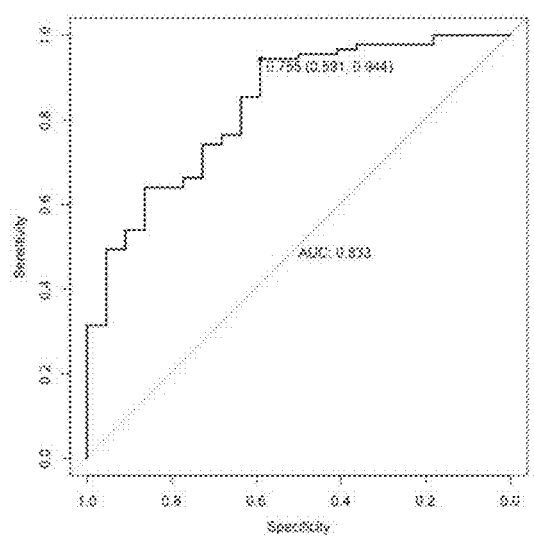
FIG. 20G Neural Network
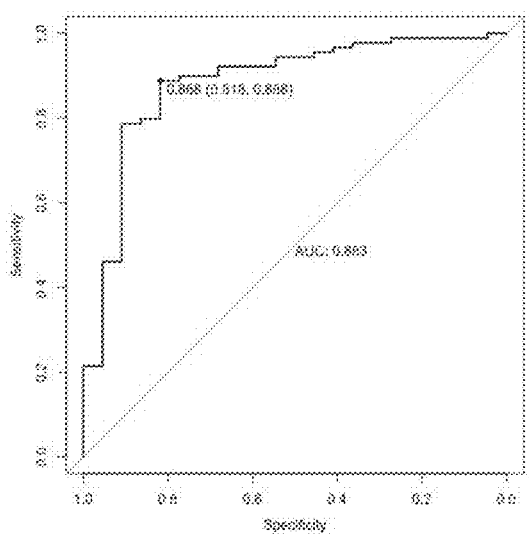
FIG. 20H Ensemble
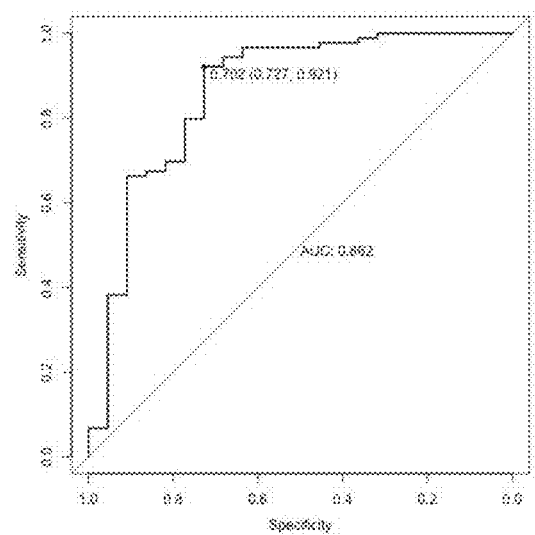

Amyotrophic Lateral Sclerosis

FIG. 22A

| # | probe | symbol | SUPER_PATHWAY | SUB_PATHWAY |
|---|---|---|---|---|
| 1 | mlon_27718 | creatine | Amino Acid | Creatine Metabolism |
| 2 | mlon_52433 | sphingomyelin (d17:1/16:0, d18:1/15:0, d16:1/17:0)* | Lipid | Sphingomyelins |
| 3 | mlon_52615 | sphingomyelin (d18:1/17:0, d17:1/18:0, d19:1/16:0) | Lipid | Sphingomyelins |
| 4 | mlon_32492 | caprylate (8:0) | Lipid | Medium Chain Fatty Acid |
| 5 | mlon_15716 | imidazole lactate | Amino Acid | Histidine Metabolism |
| 6 | mlon_1516 | sarcosine | Amino Acid | Glycine, Serine and Threonine Metabolism |
| 7 | mlon_32458 | oleamide | Lipid | Fatty Acid, Amide |
| 8 | mlon_57687 | N,N,N-trimethyl-5-aminovalerate | Amino Acid | Lysine Metabolism |
| 9 | mlon_42463 | sphingomyelin (d18:1/14:0, d16:1/16:0)* | Lipid | Sphingomyelins |
| 10 | mlon_43802 | guanidinoacetate | Amino Acid | Creatine Metabolism |
| 11 | mlon_42459 | sphingomyelin (d18:2/16:0, d18:1/16:1)* | Lipid | Sphingomyelins |
| 12 | mlon_52437 | sphingomyelin (d18:2/24:1, d18:1/24:2)* | Lipid | Sphingomyelins |
| 13 | mlon_18245 | gamma-glutamylhistidine | Peptide | Gamma-glutamyl Amino Acid |
| 14 | mlon_57482 | sphingomyelin (d18:2/23:1)* | Lipid | Sphingomyelins |
| 15 | mlon_52500 | 1-margaroyl-2-linoleoyl-GPC (17:0/18:2)* | Lipid | Phosphatidylcholine (PC) |
| 16 | mlon_53013 | glycosyl-N-palmitoyl-sphingosine (d18:1/16:0) | Lipid | Hexosylceramides (HCER) |
| 16 | mlon_53242 | 5-bromotryptophan | Amino Acid | Tryptophan Metabolism |
| 17 | mlon_52499 | 1-margaroyl-2-oleoyl-GPC (17:0/18:1)* | Lipid | Phosphatidylcholine (PC) |
| 18 | mlon_46957 | gulonate* | Cofactors and Vitamins | Ascorbate and Aldarate Metabolism |
| 19 | mlon_57453 | glycosyl ceramide (d18:2/24:1, d18:1/24:2)* | Lipid | Hexosylceramides (HCER) |
| 20 | mlon_52234 | glycosyl-N-stearoyl-sphingosine (d18:1/18:0) | Lipid | Hexosylceramides (HCER) |
| 21 | mlon_57448 | glycosyl ceramide (d18:1/23:1, d17:1/24:1)* | Lipid | Hexosylceramides (HCER) |
| 22 | mlon_32398 | sebacate (C10-DC) | Lipid | Fatty Acid, Dicarboxylate |
| 23 | mlon_57430 | N-palmitoyl-heptadecasphingosine (d17:1/16:0)* | Lipid | Ceramides |
| 24 | mlon_33967 | N-acetylisoleucine | Amino Acid | Leucine, Isoleucine and Valine Metabolism |
| 26 | mlon_47153 | sphingomyelin (d18:1/24:1, d18:2/24:0)* | Lipid | Sphingomyelins |

FIG. 22B

| #  | GLM        | RF         | PLS        | xgbDART    |
|----|------------|------------|------------|------------|
| 1  | 69.664869  | 92.5036831 | 92.1217025 | 100        |
| 2  | 29.7781334 | 13.0763002 | 44.2124965 | 45.4814387 |
| 3  | 19.2458765 | 6.42094795 | 46.6939955 | 44.5072616 |
| 4  | 27.0858459 | 75.8574107 | 71.7831984 | 35.9748919 |
| 5  | 23.2505294 | 19.3240294 | 84.1148617 | 32.2974059 |
| 6  | 45.614876  | 21.044964  | 100        | 29.6340991 |
| 7  | 21.7659993 | 100        | 70.0235175 | 26.6012799 |
| 8  | 61.8028266 | 47.6121523 | 66.3794573 | 25.0560413 |
| 9  | 43.3731058 | 11.2297604 | 36.7223644 | 20.5202029 |
| 10 | 13.7771131 | 3.19920109 | 90.8989111 | 19.3753931 |
| 11 | 14.115064  | 10.615929  | 42.2317805 | 16.3727018 |
| 12 | 0          | 6.88671815 | 35.6617272 | 14.6518718 |
| 13 | 0          | 18.7628975 | 74.3390046 | 13.5140567 |
| 14 | 0          | 2.56918157 | 43.7037475 | 11.4421579 |
| 15 | 46.5555617 | 4.57745906 | 30.8837471 | 10.8179159 |
| 16 | 18.5081941 | 6.31029658 | 33.4455747 | 10.3598521 |
| 16 | 77.2331366 | 8.1982432  | 63.5810043 | 9.65914483 |
| 17 | 20.320865  | 1.15731843 | 27.9511515 | 8.54481157 |
| 18 | 24.9199815 | 16.7811075 | 46.5325563 | 8.16397603 |
| 19 | 16.6777894 | 5.42118757 | 34.6996985 | 8.07415808 |
| 20 | 17.0149986 | 8.12484352 | 34.8650046 | 7.91451192 |
| 21 | 0.006644   | 11.8134424 | 39.9926211 | 7.4273557  |
| 22 | 15.9731967 | 6.91211461 | 67.8169863 | 6.96915436 |
| 23 | 61.7636133 | 10.0134954 | 33.8908887 | 6.69883686 |
| 24 | 33.9974489 | 6.97138432 | 52.176569  | 6.31556015 |
| 26 | 2.48142147 | 3.74874774 | 42.035783  | 6.29800584 |

FIG. 23

| Generic Treatment Name | Count (out of 206 total) | Percent |
|---|---|---|
| Riluzole | 176 | 85% |
| Edaravone | 47 | 23% |
| Dextromethorphan-Quinidine | 19 | 9% |
| Lunasin | 13 | 6% |
| Baclofen | 10 | 5% |
| Non-invasive Ventilator | 9 | 4% |
| CoQ10 (CoEnzyme Q10) | 8 | 4% |
| Feeding Tube | 5 | 2% |
| Coconut oil | 4 | 2% |
| Physical Therapy | 4 | 2% |
| Stem Cell Transplant | 4 | 2% |
| 5-Hydroxytryptophan (5-HTP) | 3 | 1% |
| Acupuncture | 3 | 1% |
| Cannabidiol | 3 | 1% |
| Curcumin | 3 | 1% |
| Glutathione | 3 | 1% |
| Mexiletine | 3 | 1% |
| Ubiquinol | 3 | 1% |
| Alpha Lipoic Acid | 2 | 1% |
| Arginine Alpha Ketoglutarate | 2 | 1% |
| Cough assist machine | 2 | 1% |
| Creatine Monohydrate | 2 | 1% |
| Gabapentin | 2 | 1% |
| L-Theanine | 2 | 1% |
| Lithium Carbonate | 2 | 1% |
| Rasagiline | 2 | 1% |
| Turmeric | 2 | 1% |
| Vitamin C (ascorbic acid) | 2 | 1% |
| Walker | 2 | 1% |
| Alpha GPC | 1 | 0% |

FIG. 24A

| # | probe | symbol | SUPER_PATHWAY | SUB_PATHWAY |
|---|---|---|---|---|
| 1 | mlon_27718 | creatine | Amino Acid | Creatine Metabolism |
| 2 | mlon_513 | creatinine | Amino Acid | Creatine Metabolism |
| 3 | mlon_52433 | sphingomyelin (d17:1/16:0, d18:1/15:0, d16:1/17:0)* | Lipid | Sphingomyelins |
| 4 | mlon_52615 | sphingomyelin (d18:1/17:0, d17:1/18:0, d19:1/16:0) | Lipid | Sphingomyelins |
| 5 | mlon_32492 | caprylate (8:0) | Lipid | Medium Chain Fatty Acid |
| 6 | mlon_15716 | imidazole lactate | Amino Acid | Histidine Metabolism |
| 7 | mlon_1516 | sarcosine | Amino Acid | Glycine, Serine and Threonine Metabolism |
| 8 | mlon_46225 | pyroglutamine* | Amino Acid | Glutamate Metabolism |
| 9 | mlon_32458 | oleamide | Lipid | Fatty Acid, Amide |
| 10 | mlon_57687 | N,N,N-trimethyl-5-aminovalerate | Amino Acid | Lysine Metabolism |
| 11 | mlon_42463 | sphingomyelin (d18:1/14:0, d16:1/16:0)* | Lipid | Sphingomyelins |
| 12 | mlon_43802 | guanidinoacetate | Amino Acid | Creatine Metabolism |
| 13 | mlon_42459 | sphingomyelin (d18:2/16:0, d18:1/16:1)* | Lipid | Sphingomyelins |
| 14 | mlon_52437 | sphingomyelin (d18:2/24:1, d18:1/24:2)* | Lipid | Sphingomyelins |
| 15 | mlon_18245 | gamma-glutamylhistidine | Peptide | Gamma-glutamyl Amino Acid |
| 16 | mlon_57482 | sphingomyelin (d18:2/23:1)* | Lipid | Sphingomyelins |
| 16 | mlon_52500 | 1-margaroyl-2-linoleoyl-GPC (17:0/18:2)* | Lipid | Phosphatidylcholine (PC) |
| 17 | mlon_60 | leucine | Amino Acid | Leucine, Isoleucine and Valine Metabolism |
| 18 | mlon_53013 | glycosyl-N-palmitoyl-sphingosine (d18:1/16:0) | Lipid | Hexosylceramides (HCER) |
| 19 | mlon_53242 | 5-bromotryptophan | Amino Acid | Tryptophan Metabolism |
| 20 | mlon_52499 | 1-margaroyl-2-oleoyl-GPC (17:0/18:1)* | Lipid | Phosphatidylcholine (PC) |
| 21 | mlon_46957 | gulonate* | Cofactors and Vitamins | Ascorbate and Aldarate Metabolism |

FIG. 24B

| # | logFC ALS+/ALS- | adj.P.Val ALS+/ALS- | DRUGBANK ENTRY | Supplements |
|---|---|---|---|---|
| 1 | 0.7007336 | 2.19E-08 | No entry | yes |
| 2 | -0.6654104 | 1.01E-07 | Drugs that decrease creatinine: | yes |
| 3 | 0.62917728 | 5.53E-07 | No entry | no |
| 4 | 0.6252479 | 5.53E-07 | No entry | no |
| 5 | 0.61856918 | 6.49E-07 | No entry | yes |
| 6 | -0.6143151 | 6.82E-07 | No entry | no |
| 7 | 0.61177427 | 6.82E-07 | No entry | yes |
| 8 | -0.608726 | 7.09E-07 | Drugs that increase pyroglutamine: Atenolol, Metoprolol, Bisoprolol, Carvedilol | yes |
| 9 | -0.5946475 | 1.38E-06 | No entry | yes |
| 10 | -0.5702332 | 4.65E-06 | No entry | no |
| 11 | 0.56228639 | 6.42E-06 | No entry | |
| 12 | -0.5442938 | 1.49E-05 | No entry | no |
| 13 | 0.53437276 | 2.23E-05 | No entry | |
| 14 | 0.53310763 | 2.23E-05 | No entry | |
| 15 | -0.5299115 | 2.44E-05 | No entry | no |
| 16 | 0.51748985 | 3.99E-05 | No entry | |
| 16 | 0.5173377 | 3.99E-05 | No entry | no |
| 17 | 0.50960376 | 5.46E-05 | Drugs that decrease leucine: Citalopram, aspirin, sertraline | yes |
| 18 | 0.50807409 | 5.56E-05 | No entry | no |
| 19 | 0.50036826 | 7.61E-05 | No entry | no |
| 20 | 0.49401206 | 9.74E-05 | No entry | no |
| 21 | -0.4865408 | 0.00012666 | No entry | no |

FIG. 25
FIG. 25A With Supplements - AUC
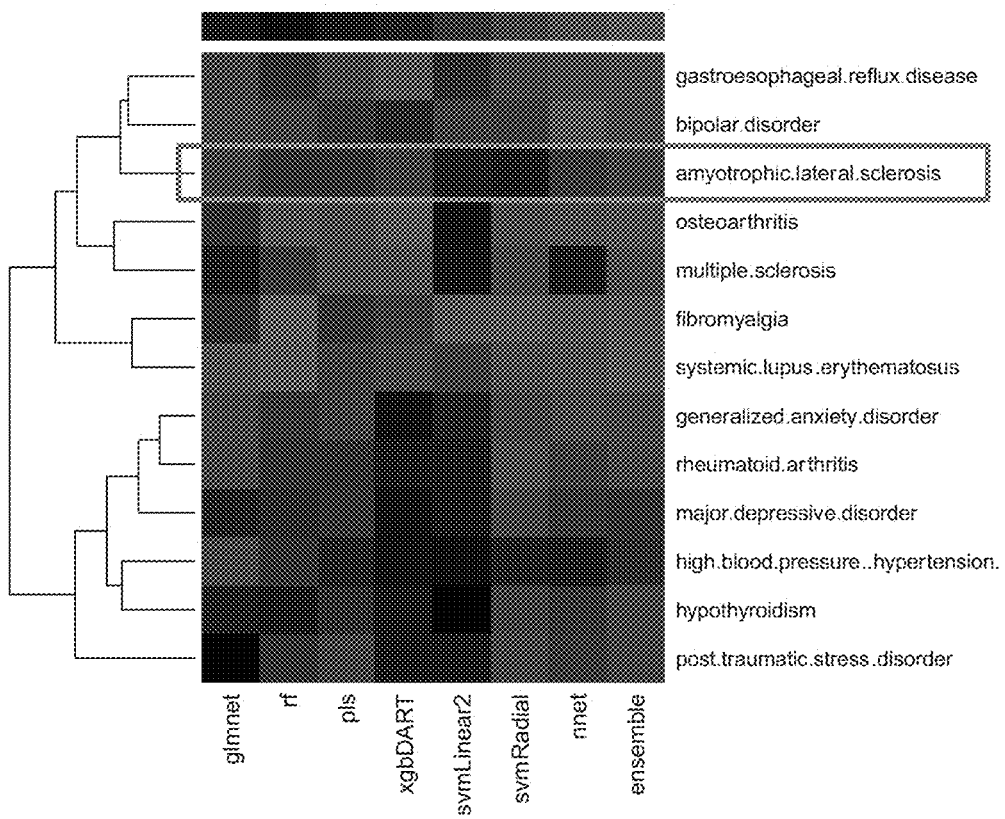
FIG. 25B ALS Ensemble AUC = 0.844
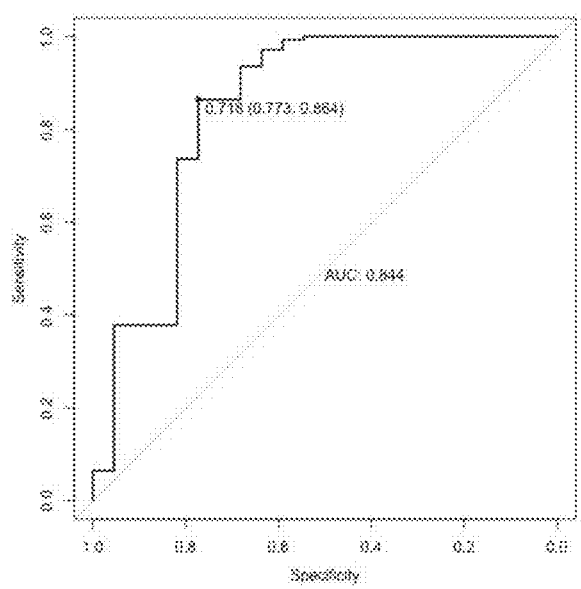

FIG. 25
FIG. 25C No Supplements - AUC
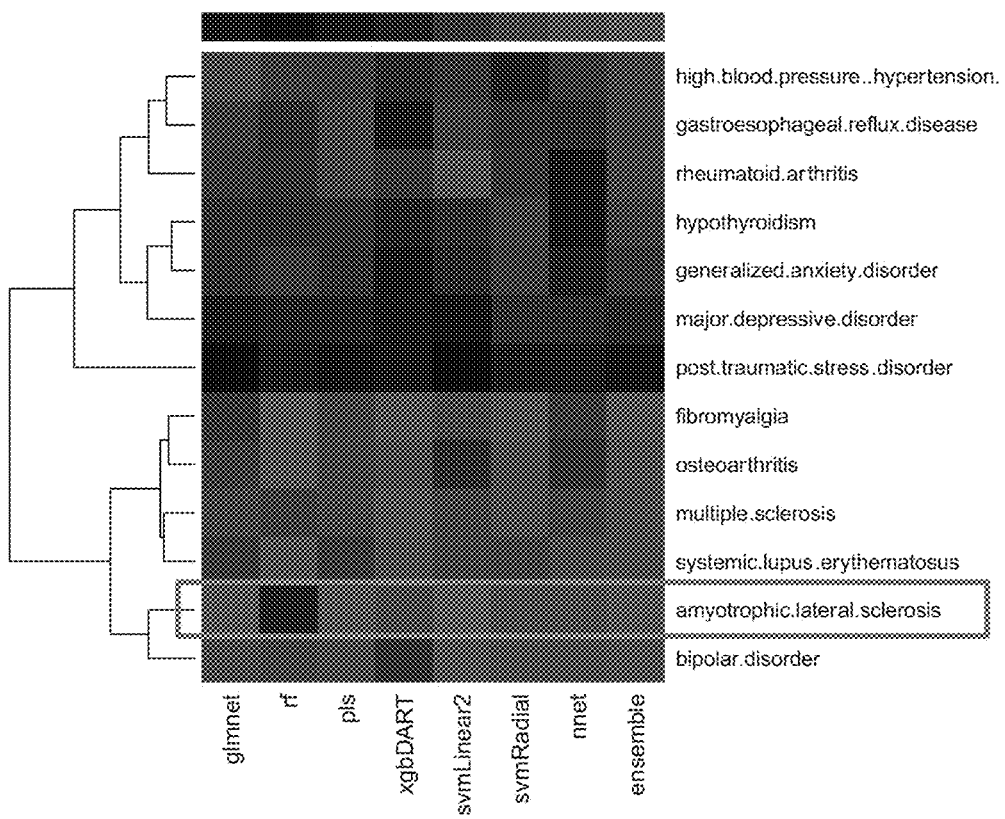
FIG. 25D ALS Ensemble AUC = 0.908
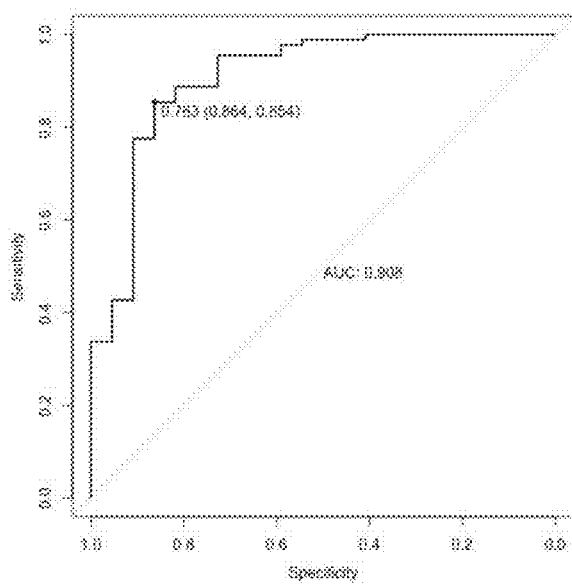

Systemic Lupus Erythematosus

FIG. 27A

| # | probe | symbol | SUPER_PATHWAY | SUB_PATHWAY |
|---|---|---|---|---|
| 1 | mlon_22116 | 4-methyl-2-oxopentanoate | Amino Acid | Leucine, Isoleucine and Valine Metabolism |
| 2 | mlon_32458 | oleamide | Lipid | Fatty Acid, Amide |
| 3 | mlon_60 | leucine | Amino Acid | Leucine, Isoleucine and Valine Metabolism |
| 4 | mlon_15676 | 3-methyl-2-oxovalerate | Amino Acid | Leucine, Isoleucine and Valine Metabolism |
| 5 | mlon_1649 | valine | Amino Acid | Leucine, Isoleucine and Valine Metabolism |
| 6 | mlon_44526 | 3-methyl-2-oxobutyrate | Amino Acid | Leucine, Isoleucine and Valine Metabolism |
| 7 | mlon_40062 | 4-hydroxy-2-oxoglutaric acid | Lipid | Fatty Acid, Dicarboxylate |
| 8 | mlon_15506 | choline | Lipid | Phospholipid Metabolism |
| 9 | mlon_554 | adenine | Nucleotide | Purine Metabolism, Adenine containing |
| 10 | mlon_42095 | palmitamide (16:0) | Lipid | Fatty Acid, Amide |
| 11 | mlon_35136 | 5-methyluridine (ribothymidine) | Nucleotide | Pyrimidine Metabolism, Uracil containing |
| 12 | mlon_1419 | 5-methylthioadenosine (MTA) | Amino Acid | Polyamine Metabolism |
| 13 | mlon_33946 | N-acetylhistidine | Amino Acid | Histidine Metabolism |
| 14 | mlon_18369 | gamma-glutamylleucine | Peptide | Gamma-glutamyl Amino Acid |
| 15 | mlon_57421 | glycosyl-N-behenoyl-sphingadienine (d18:2/22:0)* | Lipid | Hexosylceramides (HCER) |
| 16 | mlon_1125 | isoleucine | Amino Acid | Leucine, Isoleucine and Valine Metabolism |
| 17 | mlon_52281 | 2-hydroxybutyrate/2-hydroxyisobutyrate | Amino Acid | Glutathione Metabolism |
| 18 | mlon_34258 | 2-docosahexaenoyl-GPE (22:6)* | Lipid | Lysophospholipid |
| 19 | mlon_33967 | N-acetylisoleucine | Amino Acid | Leucine, Isoleucine and Valine Metabolism |
| 20 | mlon_52463 | 1-palmitoyl-2-eicosapentaenoyl-GPC (16:0/20:5)* | Lipid | Phosphatidylcholine (PC) |
| 21 | mlon_36594 | 1-linoleoyl-GPI* (18:2)* | Lipid | Lysophospholipid |

FIG. 27B

| # | glm | rf | pls | xgbDART |
|---|---|---|---|---|
| 1 | 1.64573376 | 52.2423244 | 30.7283794 | 100 |
| 2 | 50.7876517 | 66.1423706 | 94.7657748 | 97.7472434 |
| 3 | 0 | 42.055829 | 21.722457 | 57.4990296 |
| 4 | 0 | 49.8367182 | 33.13291 | 49.3745351 |
| 5 | 0 | 35.8701733 | 24.1169326 | 46.6370407 |
| 6 | 37.3653929 | 44.9008459 | 9.49992137 | 43.5137592 |
| 7 | 46.8704757 | 62.8744172 | 55.3170206 | 35.9196989 |
| 8 | 58.7048284 | 58.2229155 | 38.3437557 | 30.5693089 |
| 9 | 97.2085107 | 38.0607008 | 69.651179 | 26.6788706 |
| 10 | 0 | 43.6830464 | 81.7788111 | 25.003869 |
| 11 | 99.2370963 | 56.4018753 | 25.8538304 | 22.6845128 |
| 12 | 45.2603503 | 64.8221166 | 77.8259508 | 19.495484 |
| 13 | 0 | 61.1293831 | 61.2830443 | 19.3809025 |
| 14 | 3.72199544 | 55.8803744 | 25.8237436 | 18.4642589 |
| 15 | 45.7839603 | 47.7276437 | 58.3692886 | 17.319736 |
| 16 | 2.32237006 | 47.3798246 | 20.9640049 | 15.2127333 |
| 17 | 11.7140383 | 50.8684462 | 27.6096165 | 12.0808493 |
| 18 | 0 | 35.9989135 | 12.7812796 | 11.5152483 |
| 19 | 2.50106169 | 68.0947662 | 20.333487 | 11.4721393 |
| 20 | 32.4724139 | 56.2995652 | 29.9645809 | 10.5119016 |
| 21 | 60.6373884 | 58.4971079 | 100 | 9.22328398 |

FIG. 28

| Generic Treatment Name | Count (out of 731) | Percent |
|---|---|---|
| Hydroxychloroquine | 648 | 89% |
| Prednisone | 543 | 74% |
| Methotrexate | 237 | 32% |
| Methylprednisolone | 124 | 17% |
| Azathioprine | 122 | 17% |
| Mycophenolate mofetil | 111 | 15% |
| Belimumab | 97 | 13% |
| Cyclophosphamide | 51 | 7% |
| Naproxen OTC | 19 | 3% |
| Quinacrine | 3 | 0% |
| Multivitamins | 2 | 0% |
| Gabapentin | 2 | 0% |
| Leflunomide | 2 | 0% |
| Dapsone (DDS) | 1 | 0% |
| Naproxen Prescription | 1 | 0% |
| Vitamin D2 (ergocalciferol) | 1 | 0% |
| Ibuprofen Prescription | 1 | 0% |
| Vitamin D | 1 | 0% |
| Methotrexate injections | 1 | 0% |
| Sulfasalazine | 1 | 0% |
| Chloroquine | 1 | 0% |
| Oxycodone | 1 | 0% |
| Cevimeline | 1 | 0% |
| Lubricant Eye Drops | 1 | 0% |
| Cyclosporine ophthalmic | 1 | 0% |
| Meloxicam | 1 | 0% |
| Diclofenac | 1 | 0% |
| Abatacept | 1 | 0% |
| Hydrocodone-Acetaminophen | 1 | 0% |
| Mercaptopurine | 1 | 0% |
| Levothyroxine | 1 | 0% |
| Colchicine | 1 | 0% |

FIG. 29A

| # | probe | symbol | SUPER_PATHWAY | SUB_PATHWAY |
|---|---|---|---|---|
| 1 | mlon_22116 | 4-methyl-2-oxopentanoate | Amino Acid | Leucine, Isoleucine and Valine Metabolism |
| 2 | mlon_32458 | oleamide | Lipid | Fatty Acid, Amide |
| 3 | mlon_60 | leucine | Amino Acid | Leucine, Isoleucine and Valine Metabolism |
| 4 | mlon_15676 | 3-methyl-2-oxovalerate | Amino Acid | Leucine, Isoleucine and Valine Metabolism |
| 5 | mlon_1649 | valine | Amino Acid | Leucine, Isoleucine and Valine Metabolism |
| 6 | mlon_44526 | 3-methyl-2-oxobutyrate | Amino Acid | Leucine, Isoleucine and Valine Metabolism |
| 7 | mlon_40062 | 4-hydroxy-2-oxoglutaric acid | Lipid | Fatty Acid, Dicarboxylate |
| 8 | mlon_15506 | choline | Lipid | Phospholipid Metabolism |
| 9 | mlon_554 | adenine | Nucleotide | Purine Metabolism, Adenine containing |
| 10 | mlon_42095 | palmitamide (16:0) | Lipid | Fatty Acid, Amide |
| 11 | mlon_35136 | 5-methyluridine (ribothymidine) | Nucleotide | Pyrimidine Metabolism, Uracil containing |
| 12 | mlon_1419 | 5-methylthioadenosine (MTA) | Amino Acid | Polyamine Metabolism |
| 13 | mlon_33946 | N-acetylhistidine | Amino Acid | Histidine Metabolism |
| 14 | mlon_18369 | gamma-glutamylleucine | Peptide | Gamma-glutamyl Amino Acid |
| 15 | mlon_57421 | glycosyl-N-behenoyl-sphingadienine (d18:2/22:0)* | Lipid | Hexosylceramides (HCER) |
| 16 | mlon_1125 | isoleucine | Amino Acid | Leucine, Isoleucine and Valine Metabolism |
| 17 | mlon_52281 | 2-hydroxybutyrate/2-hydroxyisobutyrate | Amino Acid | Glutathione Metabolism |
| 18 | mlon_34258 | 2-docosahexaenoyl-GPE (22:6)* | Lipid | Lysophospholipid |
| 19 | mlon_33967 | N-acetylisoleucine | Amino Acid | Leucine, Isoleucine and Valine Metabolism |
| 20 | mlon_52463 | 1-palmitoyl-2-eicosapentaenoyl-GPC (16:0/20:5)* | Lipid | Phosphatidylcholine (PC) |
| 21 | mlon_36594 | 1-linoleoyl-GPI* (18:2)* | Lipid | Lysophospholipid |
| 22 | mlon_40730 | imidazole propionate | Amino Acid | Histidine Metabolism |
| 23 | mlon_42374 | 2-aminobutyrate | Amino Acid | Glutathione Metabolism |
| 24 | mlon_35631 | 1-palmitoyl-GPE (16:0) | Lipid | Lysophospholipid |
| 25 | mlon_55015 | gamma-glutamyl-alpha-lysine | Peptide | Gamma-glutamyl Amino Acid |

FIG. 29B

| # | logFC (SLE+ vs SLE-) | adj.P.Val (SLE+ vs. SLE-) | DRUGBANK ENTRY | Supplements |
|---|---|---|---|---|
| 1 | -0.630641 | 0.00069864 | No entry | no |
| 2 | 0.57635784 | 0.001977 | No entry | yes |
| 3 | -0.5742564 | 0.001977 | The following drugs decrease leucine: Citalopram, aspirin, sertraline | yes |
| 4 | -0.5346764 | 0.00595955 | No entry | no |
| 5 | -0.5214855 | 0.00630761 | The following drugs decrease valine: Citalopram, aspirin | yes |
| 6 | -0.5164785 | 0.00630761 | #N/A | no |
| 7 | -0.5162608 | 0.00630761 | No entry | no |
| 8 | -0.5069092 | 0.00741007 | The following drugs increase choline: Choline | yes |
| 9 | 0.50360091 | 0.00741007 | No entry | yes |
| 10 | 0.48656139 | 0.01073786 | No entry | no |
| 11 | -0.4839867 | 0.01073786 | #N/A | no |
| 12 | 0.4827669 | 0.01073786 | #N/A | no |
| 13 | 0.46878558 | 0.01520718 | #N/A | no |
| 14 | -0.46334 | 0.01605848 | No entry | no |
| 15 | -0.4588736 | 0.01605848 | No entry | no |
| 16 | -0.456182 | 0.01605848 | Sertraline decreases isoleucine. | yes |
| 17 | -0.4555309 | 0.01605848 | No entry | yes |
| 18 | -0.455278 | 0.01605848 | No entry | no |
| 19 | -0.4542226 | 0.01605848 | No entry | yes |
| 20 | -0.449824 | 0.01687592 | No entry | no |
| 21 | 0.44910133 | 0.01687592 | #N/A | no |
| 22 | 0.44686178 | 0.01719084 | No entry | no |
| 23 | -0.437231 | 0.02167655 | No entry | yes |
| 24 | -0.4304681 | 0.02364006 | #N/A | no |
| 25 | -0.4301806 | 0.02364006 | No entry | no |

FIG. 30
FIG. 30A With Supplements - AUC
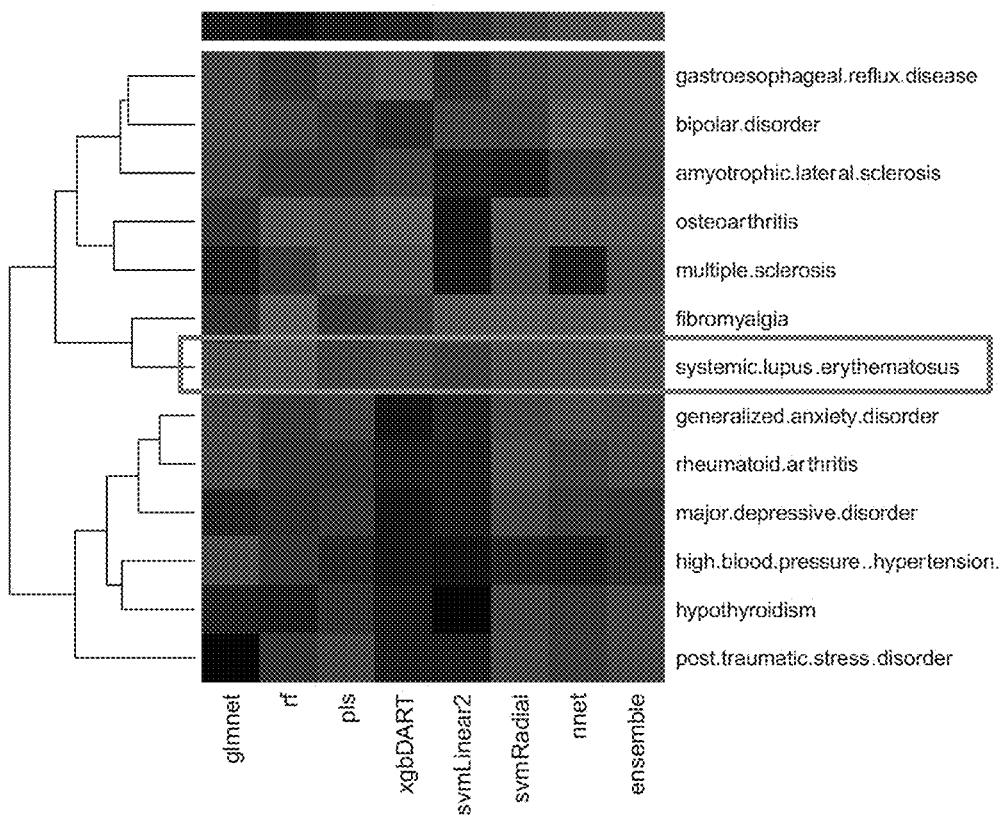
FIG. 30B SLE Ensemble AUC = 0.902
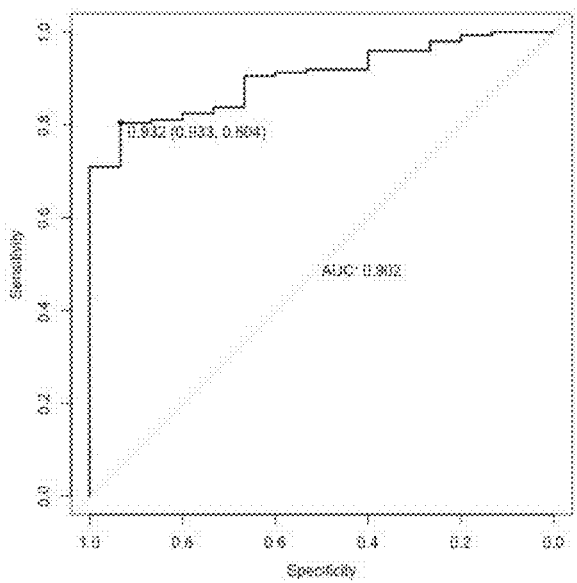

FIG. 30
FIG. 30C No Supplements - AUC
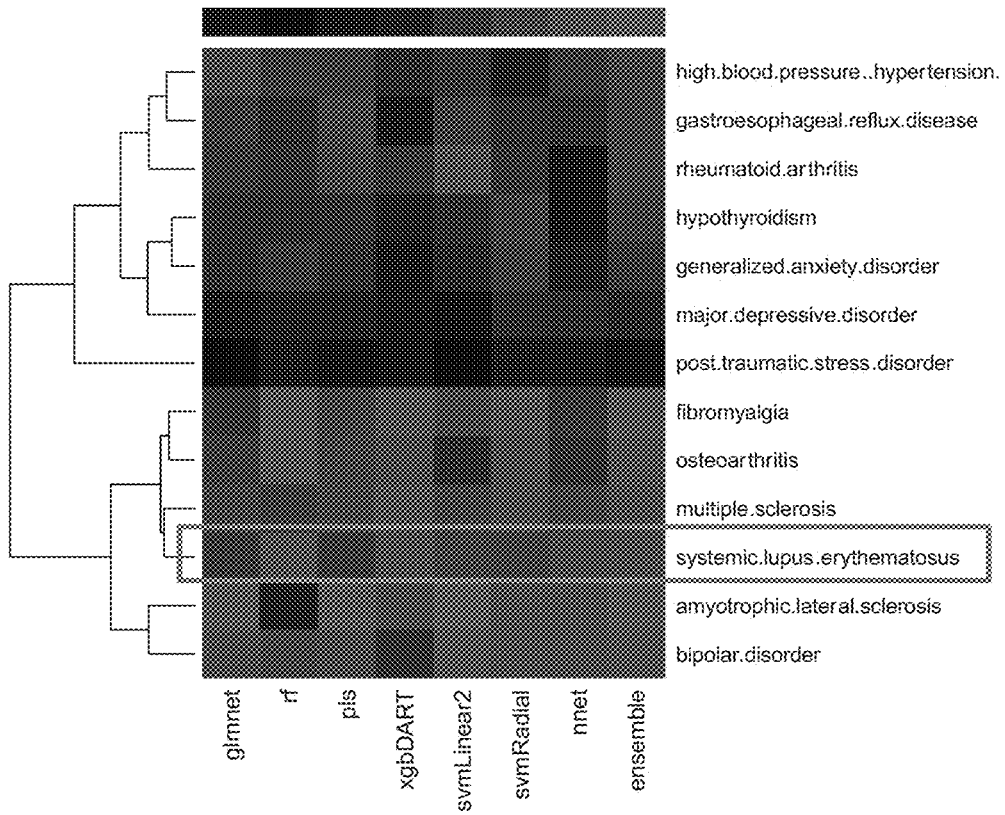
FIG. 30D SLE Ensemble AUC = 0.845
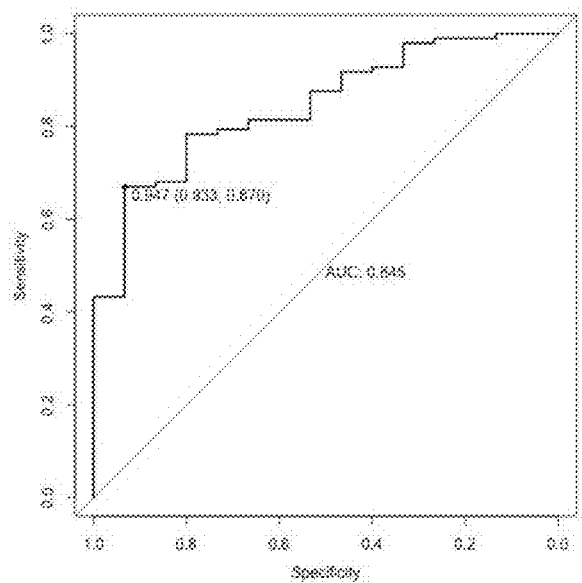

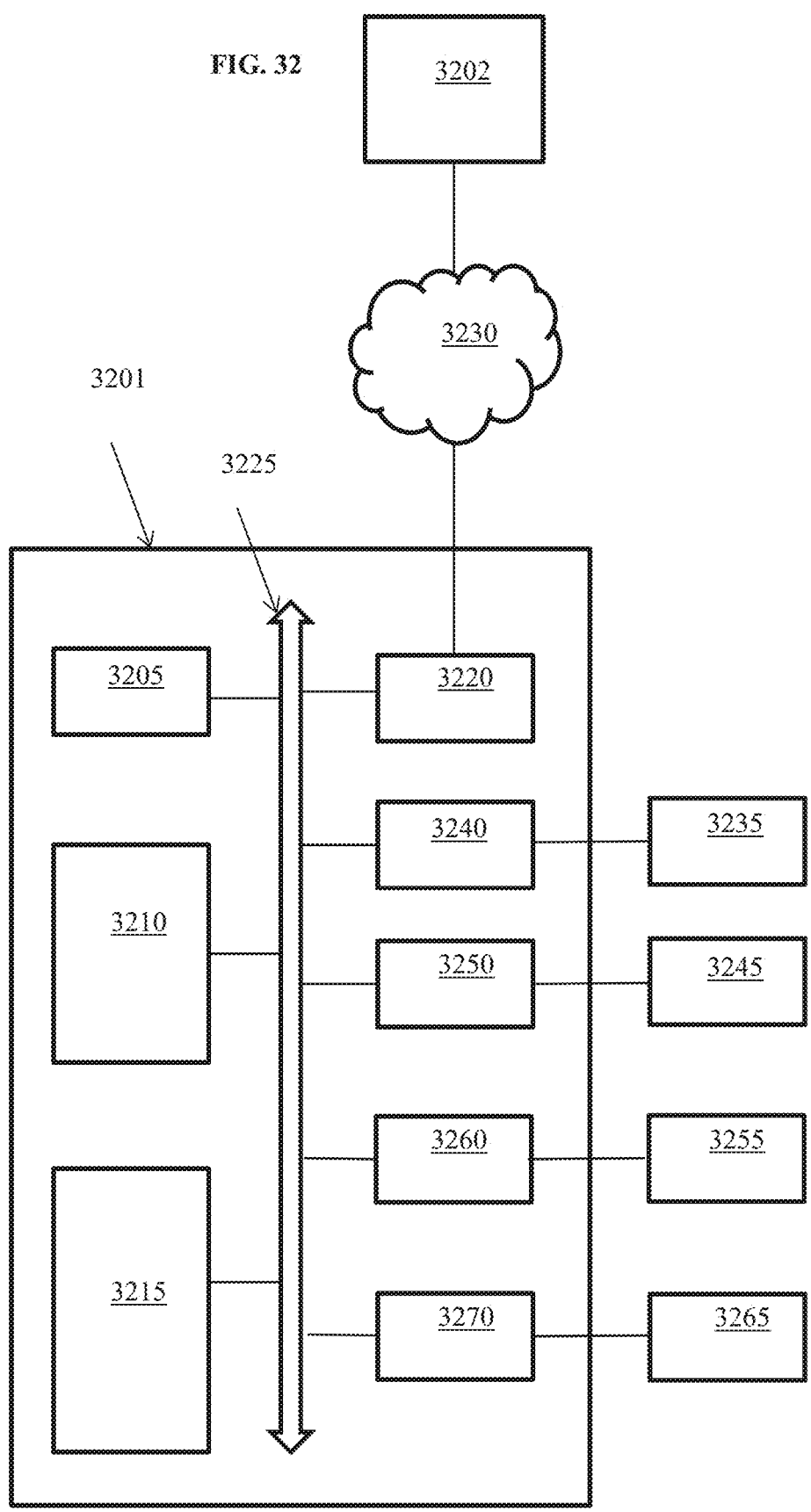

DISEASE SPECTRUM CLASSIFICATION

CROSS-REFERENCE

This application claims the benefit of U.S. Provisional Application No. 62/774,788, filed Dec. 3, 2018, and U.S. Provisional Application No. 62/818,310, filed Mar. 14, 2019, the contents of each of which is hereby incorporated herein by reference.

BACKGROUND

Personalized medicine has the potential to detect various possible diseases, disorders, or conditions that are personalized to the individual patient based on molecular profiling. However, many challenges remain in generating therapeutically useful diagnoses.

SUMMARY

Described herein are platforms, systems, media, and methods for assessing an individual for one or more diseases, disorders, or conditions. A machine learning algorithm can be used to provide the assessment based on personalized data derived from the individual. The personalized data can include metabolite data from a specimen or biological sample of the individual.

In one aspect, described herein is a system for assessing an individual, comprising: (a) a processor; (b) a non-transitory computer readable medium encoded with software comprising one or more machine learning algorithms together with instructions configured to cause the processor to: (i) receive data related to a specimen taken from the individual; and (ii) provide the data as input to the one or more machine learning algorithms, wherein the one or more machine learning algorithms use the data to generate a classification of the individual relative to a plurality of related classifications. In some instances, the one or more machine learning algorithms comprise an ensemble of machine learning algorithms. Sometimes, the ensemble comprises at least three machine learning algorithms. In certain cases, the ensemble of machine learning algorithms comprises a Generalized Linear algorithm, a Random Forests algorithm, a Partial Least Squares algorithm, and Extreme Gradient Boosting algorithm, a Support Vector Machines with Linear Basis Function Kernel algorithm, a Support Vector Machines with Radial Basis Function Kernel, and a Neural Networks algorithm. In some cases, each machine learning algorithm of the ensemble of machine learning algorithms produces an output that is averaged by the software. Sometimes, each machine learning algorithm of the ensemble of machine learning algorithms produces an output and wherein at least one output is an input for at least one of the machine learning algorithms. In certain instances, the at least one machine learning algorithm is trained using data relating to specimens from other individuals. Oftentimes, the specimen comprises a biological sample. In some cases, the specimen comprises at least one of a sputum sample, a urine sample, a blood sample, a cerebrospinal fluid sample, a stool sample, a hair sample, and a biopsy. The data often relates to a metabolite. In certain instances, the metabolite comprises at least one of oleamide, creatine, and 4-methyl-2-oxopentanoate. Sometimes, the instructions are further configured to cause the processor to receive a parameter related to the individual and wherein the one or more machine learning algorithms use the parameter together with the data to generate the classification of the individual relative to the plurality of related classifications. The parameter often comprises at least one of an age, a gender, a race, a weight, a BMI, a height, a waist size, a blood pressure, a heart rate, and a temperature. Sometimes, the classification comprises a disease. In various instances, the disease comprises at least one of multiple sclerosis, amyotrophic lateral sclerosis, systemic lupus erythematosus, fibromyalgia, and gastrointestinal reflux disease. In certain cases, the plurality of related classifications comprise a spectrum of severity of a single disease. Sometimes, the plurality of related classifications comprise a spectrum of prognoses of a single disease. In certain instances, the plurality of related classifications comprise a spectrum of related diseases. The spectrum of related diseases comprise a plurality of neurological diseases that share at least one common feature, in various cases.

In another aspect, disclosed herein is a computer implemented method for assessing an individual, comprising: (a) receiving data relating to a specimen taken from the individual; (b) providing the data as input to one or more machine learning algorithms; and (c) generating, using the one or more machine learning algorithms, a classification of the individual relative to a plurality of related classifications based on the data. In some instances, the one or more machine learning algorithms comprise an ensemble of machine learning algorithms. Sometimes, the ensemble comprises at least three machine learning algorithms. In certain cases, the ensemble of machine learning algorithms comprises a Generalized Linear algorithm, a Random Forests algorithm, a Partial Least Squares algorithm, and Extreme Gradient Boosting algorithm, a Support Vector Machines with Linear Basis Function Kernel algorithm, a Support Vector Machines with Radial Basis Function Kernel, and a Neural Networks algorithm. In some cases, each machine learning algorithm of the ensemble of machine learning algorithms produces an output that is averaged by the software. Sometimes, each machine learning algorithm of the ensemble of machine learning algorithms produces an output and wherein at least one output is an input for at least one of the machine learning algorithms. In certain instances, the at least one machine learning algorithm is trained using data relating to specimens from other individuals. Oftentimes, the specimen comprises a biological sample. In some cases, the specimen comprises at least one of a sputum sample, a urine sample, a blood sample, a cerebrospinal fluid sample, a stool sample, a hair sample, and a biopsy. The data often relates to a metabolite. In certain instances, the metabolite comprises at least one of oleamide, creatine, and 4-methyl-2-oxopentanoate. Sometimes, the instructions are further configured to cause the processor to receive a parameter related to the individual and wherein the one or more machine learning algorithms use the parameter together with the data to generate the classification of the individual relative to the plurality of related classifications. The parameter often comprises at least one of an age, a gender, a race, a weight, a BMI, a height, a waist size, a blood pressure, a heart rate, and a temperature. Sometimes, the classification comprises a disease. In various instances, the disease comprises at least one of multiple sclerosis, amyotrophic lateral sclerosis, systemic lupus erythematosus, fibromyalgia, and gastrointestinal reflux disease. In certain cases, the plurality of related classifications comprise a spectrum of severity of a single disease. Sometimes, the plurality of related classifications comprise a spectrum of prognoses of a single disease. In certain instances, the plurality of related classifications comprise a spectrum of related diseases. The spectrum of related diseases comprise a plurality of neurological diseases that share at least one common feature, in various cases.

In another aspect, disclosed herein is a system for assessing an individual, comprising: (a) a processor; (b) a non-transitory computer readable medium encoded with software comprising one or more machine learning algorithms together with instructions configured to cause the processor to: (i) receive data related to a specimen taken from the individual; and (ii) provide the data as input to the one or more machine learning algorithms, wherein the one or more machine learning algorithms use the data to generate an assessment of one or more traits of the individual. In some cases, the one or more machine learning algorithms comprise an ensemble of machine learning algorithms. Sometimes, the ensemble comprises at least three machine learning algorithms. In some aspects, the ensemble of machine learning algorithms comprises a Generalized Linear algorithm, a Random Forests algorithm, a Partial Least Squares algorithm, and Extreme Gradient Boosting algorithm, a Support Vector Machines with Linear Basis Function Kernel algorithm, a Support Vector Machines with Radial Basis Function Kernel, and a Neural Networks algorithm. In certain instances, each machine learning algorithm of the ensemble of machine learning algorithms produces an output that is averaged by the software. In various aspects, each machine learning algorithm of the ensemble of machine learning algorithms produces an output and wherein at least one output is an input for at least one of the machine learning algorithms. In certain cases, at least one machine learning algorithm is trained using data relating to specimens from other individuals. Sometimes, the specimen comprises a biological sample. In some instances, the specimen comprises at least one of a sputum sample, a urine sample, a blood sample, a cerebrospinal fluid sample, a stool sample, a hair sample, and a biopsy. In certain aspects, the data relates to a metabolite, a protein, a nucleic acid, or any combination thereof. In various cases, the metabolite comprises at least one of oleamide, creatine, and 4-methyl-2-oxopentanoate. Sometimes, the instructions are further configured to cause the processor to receive a parameter related to the individual and wherein the one or more machine learning algorithms use the parameter together with the data to generate the assessment of the individual. In some cases, the parameter comprises at least one of an age, a gender, a race, a weight, a BMI, a height, a waist size, a blood pressure, a heart rate, and a temperature. In certain aspects, the assessment comprises at least one trait selected from a category that is personal characteristics, general health, mental health, health behaviors, interventions, organ systems, environmental, or conditions. In some instances, the one or more traits comprises at least one of sex, age, BMI, race, ethnicity, personality, traits, family history, current, conditions, acute infection, allergies, perceived health, circadian cycle, menstrual cycle, genetic predisposition, thrive, cognition, energy, depression, anxiety, stress, coping ability, feels good or bad, fitness, substances, sleep, diet, sun exposure, sex drive, vaccines, treatment, procedures, supplement, circulatory, dental, digestive, endocrine, lymph or immune system, metabolism, musculoskeletal system, nervous system, renal system, reproductive system, respiratory system, skin, life events including trauma, living environment, work environment, chemical, exposures, social functioning, diagnostic history, disease severity, symptoms and signs, potential, complications, and, comorbidities, monitoring labs and tests, or treatment.

In another aspect, disclosed herein is a computer implemented method for assessing an individual, comprising: (a) receiving data relating to a specimen taken from the individual; (b) providing the data as input to one or more machine learning algorithms; and (c) generating, using the one or more machine learning algorithms, an assessment of one or more traits of the individual. In some cases, the one or more machine learning algorithms comprise an ensemble of machine learning algorithms. Sometimes, the ensemble comprises at least three machine learning algorithms. In some aspects, the ensemble of machine learning algorithms comprises a Generalized Linear algorithm, a Random Forests algorithm, a Partial Least Squares algorithm, and Extreme Gradient Boosting algorithm, a Support Vector Machines with Linear Basis Function Kernel algorithm, a Support Vector Machines with Radial Basis Function Kernel, and a Neural Networks algorithm. In certain instances, each machine learning algorithm of the ensemble of machine learning algorithms produces an output that is averaged by the software. In various aspects, each machine learning algorithm of the ensemble of machine learning algorithms produces an output and wherein at least one output is an input for at least one of the machine learning algorithms. In certain cases, at least one machine learning algorithm is trained using data relating to specimens from other individuals. Sometimes, the specimen comprises a biological sample. In some instances, the specimen comprises at least one of a sputum sample, a urine sample, a blood sample, a cerebrospinal fluid sample, a stool sample, a hair sample, and a biopsy. In certain aspects, the data relates to a metabolite, a protein, a nucleic acid, or any combination thereof. In various cases, the metabolite comprises at least one of oleamide, creatine, and 4-methyl-2-oxopentanoate. Sometimes, the method further comprises receiving a parameter related to the individual and wherein the one or more machine learning algorithms use the parameter together with the data to generate the assessment of the individual. In some cases, the parameter comprises at least one of an age, a gender, a race, a weight, a BMI, a height, a waist size, a blood pressure, a heart rate, and a temperature. In certain aspects, the assessment comprises at least one trait selected from a category that is personal characteristics, general health, mental health, health behaviors, interventions, organ systems, environmental, or conditions. In some instances, the one or more traits comprises at least one of sex, age, BMI, race, ethnicity, personality, traits, family history, current, conditions, acute infection, allergies, perceived health, circadian cycle, menstrual cycle, genetic predisposition, thrive, cognition, energy, depression, anxiety, stress, coping ability, feels good or bad, fitness, substances, sleep, diet, sun exposure, sex drive, vaccines, treatment, procedures, supplement, circulatory, dental, digestive, endocrine, lymph or immune system, metabolism, musculoskeletal system, nervous system, renal system, reproductive system, respiratory system, skin, life events including trauma, living environment, work environment, chemical, exposures, social functioning, diagnostic history, disease severity, symptoms and signs, potential, complications, and, comorbidities, monitoring labs and tests, or treatment.

BRIEF DESCRIPTION OF THE DRAWINGS

The novel features of the invention are set forth with particularity in the appended claims. The file of this patent contains at least one drawing/photograph executed in color. Copies of this patent with color drawing(s)/photograph(s) will be provided by the Office upon request and payment of the necessary fee. A better understanding of the features and advantages of the present invention will be obtained by reference to the following detailed description that sets forth illustrative embodiments, in which the principles of the invention are utilized, and the accompanying drawings of which:

FIG. 1 shows a list of conditions and the corresponding number of participants having metabolite data that are reported to have each condition. Those conditions that have been evaluated according to the methods described herein have at least 35 participants and are bracketed by the box;

FIG. 2A, FIG. 2B, and FIG. 2C show heat maps of the AUC performance of 8 different machine learning algorithms or classifiers including the Ensemble classifier that are trained and tested using 3 different subpopulations of the participant data. The classifiers are listed on the X-axis, and the various diseases, disorders, or conditions are listed on the Y-axis. The classifiers were trained and tested using participant metabolite data.

FIG. 5A, FIG. 5B, FIG. 5C, FIG. 5D, FIG. 5E, FIG. 5F, FIG. 5G, FIG. 5H, FIG. 5I, and FIG. 5J show some high performing Ensemble classifiers based on disease, disorder, or condition. FIG. 5A shows the AUC curve for amyotrophic lateral sclerosis. FIG. 5B shows the AUC curve for multiple sclerosis. FIG. 5C shows the AUC curve for bipolar disorder. FIG. 5D shows the AUC curve for systemic lupus erythematosus. FIG. 5E shows the AUC curve for fibromyalgia. FIG. 5F shows the AUC curve for generalized anxiety disorder. FIG. 5G shows the AUC curve for osteoarthritis. FIG. 5H shows the AUC curve for gastroesophageal reflux disease. FIG. 5I shows the AUC curve for high blood pressure. FIG. 5J shows the AUC curve for major depressive disorder.

FIG. 6A shows a diagram of disease spectrum metabolite scores showing a healthy range (green/non-disease) overlaid with a participant score (red). FIG. 6B shows a diagram of disease spectrum metabolite scores for an individual on a diet. The disease spectrum metabolite scores can be monitored over time (e.g., from repeated metabolite sampling) to determine progression of a disease, disorder, or condition as well as response to various therapeutic interventions such as, for example, diet as shown in FIG. 6B.

FIG. 7A shows the model score for diet participants with a threshold of 0.85 for positive classification of osteoarthritis. FIG. 7B shows the model scores for diet participants with a threshold of 0.91 for positive classification of high blood pressure.

FIG. 8A, FIG. 8B, FIG. 8C, FIG. 8D, FIG. 8E, FIG. 8F, and FIG. 8G show diagrams of before (left) and after (right) disease spectrum metabolite scores for diet participants.

FIG. 9A shows a diagram of disease spectrum scores for a participant who has multiple sclerosis and amyotrophic lateral sclerosis. FIG. 9B shows the model scores for diet participants with a threshold of 0.46 for positive classification of multiple sclerosis.

FIG. 10A shows a diagram of disease spectrum scores for a participant who has amyotrophic lateral sclerosis. FIG. 10B shows the model scores for diet participants with a threshold of 0.56 for positive classification of amyotrophic lateral sclerosis.

FIGS. 11A-11B shows training and testing statistics for multiple sclerosis using 7 different machine learning models based on 89 MS positive cases and 292 MS negative cases. The results are based on 100 re-samplings of 5-fold cross-validation repeated 20 times. FIG. 11A shows the 0.95 confidence interval for ROC for 7 different machine learning algorithms or classifiers. FIG. 11B shows the 0.95 confidence interval for sensitivity for 7 different machine learning algorithms or classifiers. FIG. 11C shows the 0.95 confidence interval for specificity for 7 different machine learning algorithms or classifiers.

FIG. 12 shows AUC curves for the 7 different machine learning algorithms or classifiers and the Ensemble classifier with respect to multiple sclerosis (22 MS positive cases; 89 MS negative cases): FIG. 12A generalized linear model; FIG. 12B partial least squares; FIG. 12C support vector machine; FIG. 12D radial kernel SVM; FIG. 12E random forest; FIG. 12F extreme gradient boosting; FIG. 12G neural network; FIG. 12H Ensemble.

FIG. 13A shows an AUC curve for an Ensemble classifier for classifying multiple sclerosis with an AUC of 0.891. The model correctly called 47 of 53 MS positive cases (89%) with 6 false negatives (11%) and correctly called 141 of 179 MS negative cases (79%) with 38 false positives (21%). Of the 38 false positives, 28 were ALS positive, indicating that using a combination of MS and ALS classifiers would enhance performance.

FIG. 13B shows the same AUC curve as FIG. 13A but using an alternative threshold that maximizes specificity (see dotted line). Using this alternative threshold, the model correctly called 39 of 53 MS positive cases (74%) with 14 false negatives (26%) and correctly called 158 of 179 MS negative cases (88%) with 21 false positives (12%). Of the 21 false positives, 17 were ALS positive.

FIG. 14 shows a list of 38 participants classified as false positives according to the model from FIG. 13. FIG. 14 shows various relevant parameters including the participant number, reported MS status, score, call (prediction according to FIG. 13A), optimal specificity (call/prediction according to FIG. 13B when optimizing specificity), participant condition, number, and ALS and MS status.

FIG. 15A shows a table with various features used in MS classifiers and corresponding pathway information. FIG. 15B shows the same feature list with corresponding feature importance based on the best performing models in CV.

FIG. 16 shows self-reported multiple sclerosis treatments.

FIG. 17A shows a table with various features used in MS classifiers and corresponding pathway information. FIG. 17B shows the same feature list with drugs and/or specific supplements identified for the various metabolites in the feature list.

FIG. 18A shows a map of the AUC performance of 8 different machine learning algorithms or classifiers including the Ensemble classifier when supplements are not excluded from the feature list. FIG. 18B shows an AUC curve for the MS Ensemble classifier for MS with an AUC of 0.866 with supplements. FIG. 18C shows a map of the AUC performance of 8 different machine learning algorithms or classifiers including the Ensemble classifier when supplements are excluded from the feature list. FIG. 18D shows an AUC curve for the MS Ensemble classifier for MS with an AUC of 0.845 without supplements.

FIGS. 19A-19B shows training and testing statistics for amyotrophic lateral sclerosis using 7 different machine learning models based on 84 ALS positive cases and 296 ALS negative cases. The results are based on 100 re-samplings of cross-validation. FIG. 19A shows the 0.95 confidence interval for ROC for 7 different machine learning algorithms or classifiers. FIG. 19B shows the 0.95 confidence interval for sensitivity for 7 different machine learning algorithms or classifiers. FIG. 19C shows the 0.95 confidence interval for specificity for 7 different machine learning algorithms or classifiers.

FIG. 20 shows AUC curves for the 7 different machine learning algorithms or classifiers and the Ensemble classifier with respect to amyotrophic lateral sclerosis (21 ALS positive cases; 91 ALS negative cases): FIG. 20A generalized linear model; FIG. 20B partial least squares; FIG. 20C support vector machine; FIG. 20D SVMR; FIG. 20E random forest; FIG. 20F extreme gradient boosting; FIG. 20G neural network; FIG. 20H Ensemble.

FIG. 22A shows a table with various features used in ALS classifiers and corresponding pathway information. FIG. 22B shows the same feature list with corresponding feature importance based on the best performing models in CV.

FIG. 23 shows self-reported amyotrophic lateral sclerosis treatments.

FIG. 24A shows a table with various features used in ALS classifiers and corresponding pathway information. FIG. 24B shows the same feature list with drugs and/or specific supplements identified for the various metabolites in the feature list.

FIG. 25A shows a map of the AUC performance of 8 different machine learning algorithms or classifiers including the Ensemble classifier when supplements are not excluded from the feature list. FIG. 25B shows an AUC curve for the ALS Ensemble classifier for MS with an AUC of 0.844 with supplements. FIG. 25C shows a map of the AUC performance of 8 different machine learning algorithms or classifiers including the Ensemble classifier when supplements are excluded from the feature list. FIG. 25D shows an AUC curve for the ALS Ensemble classifier with an AUC of 0.908 without supplements. This demonstrates an improvement when supplements are excluded.

FIG. 27A shows a table with various features used in SLE classifiers and corresponding pathway information. FIG. 27B shows the same feature list with corresponding feature importance based on the best performing models in CV.

FIG. 28 shows self-reported systemic lupus erythematosus treatments.

FIG. 29A shows a table with various features used in SLE classifiers and corresponding pathway information. FIG. 29B shows the same feature list with drugs and/or specific supplements identified for the various metabolites in the feature list.

FIG. 30A shows a map of the AUC performance of 8 different machine learning algorithms or classifiers including the Ensemble classifier when supplements are not excluded from the feature list. FIG. 30B shows an AUC curve for the SLE Ensemble classifier with an AUC of 0.902 with supplements. FIG. 30C shows a map of the AUC performance of 8 different machine learning algorithms or classifiers including the Ensemble classifier when supplements are excluded from the feature list. FIG. 30D shows an AUC curve for the ALS Ensemble classifier with an AUC of 0.845 without supplements. This demonstrates an improvement when supplements are excluded.

FIG. 32 shows an exemplary embodiment of a system as described herein.

DETAILED DESCRIPTION

Figure 3:
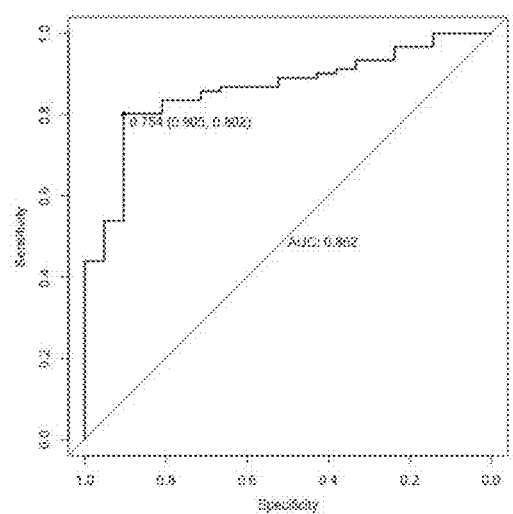
FIG. 3A, FIG. 3B, and FIG. 3C show the AUC curves of the Ensemble classifier trained and tested using for 3 different subpopulations of participant data for multiple sclerosis.
FIG. 3D shows a model summary that averages the individual Ensembles from FIGS. 3A-3C.
Figure 3A:
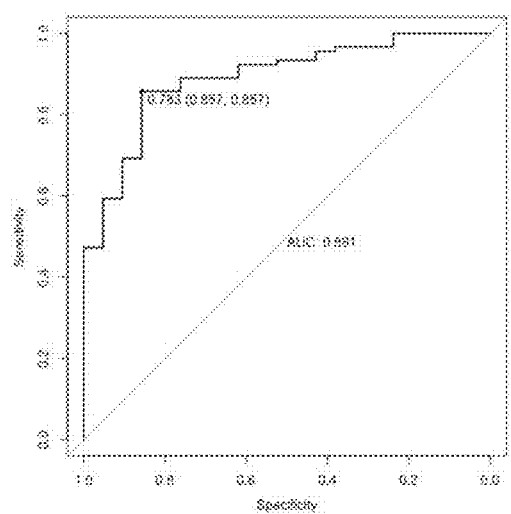
Figure 3B:
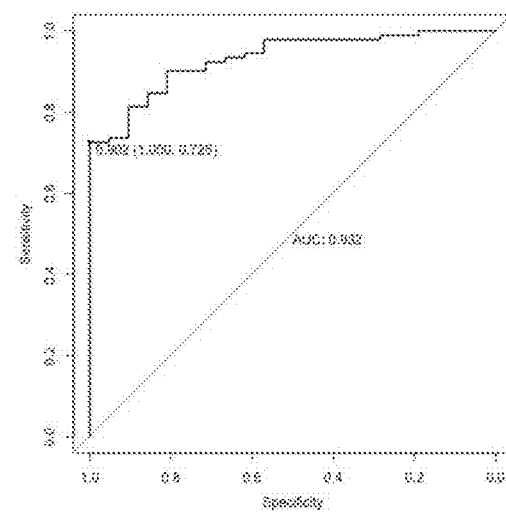
Figure 3C:
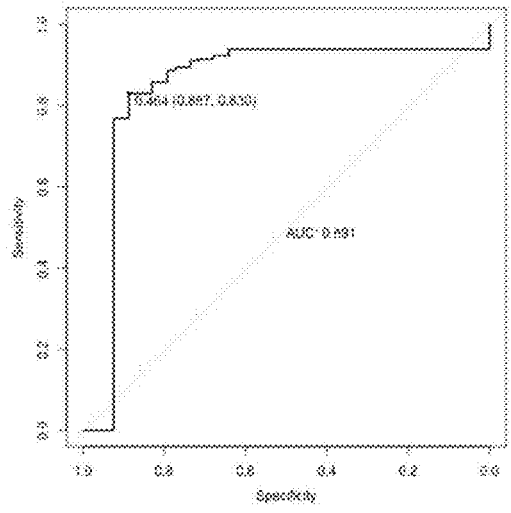

Described herein are devices, software, systems, and methods for assessing an individual for a disease, disorder, or condition by generating a classification relative to a plurality of related classifications based on data obtained from the individual. More specifically, the data comprises metabolite data suitable for detecting at least one of the presence, severity, duration, or status of a disease, disorder, or condition. In some instances, the metabolite data is obtained from a biological sample of the individual and evaluated to determine the presence and/or quantitation of one or more metabolites in the sample. The metabolite data may be obtained multiple times from the individual to enable monitoring over time. The data can also include non-metabolite data such as nucleic acid sequencing and/or expression data. In some cases, the data includes protein or polypeptide data such as expression or quantitation level for a panel of proteins or polypeptides. Machine learning algorithms can be trained to generate classifiers or models that comprise a panel or list of features such as discriminating metabolites or other biomarkers. Multiple machine learning algorithms may be utilized to assess the sample. In some cases, an Ensemble classifier that consolidates two or more machine learning algorithms is used to generate the classification. The classification can include a grade, severity, or class of a particular disease, disorder, or condition. In some embodiments, the systems, devices, software, and methods described herein are configured to identify a diagnostic modality that should be used as an additional step in evaluating an individual who is found by the systems, devices, software, and methods to have a particular disease, disorder, or condition. In some embodiments, the systems, devices, software, and methods described herein are configured to identify a therapy for an individual based on the results of the classification.

Disease Scoring or Classification

In some aspects, described herein are devices, software, systems, and methods for providing disease scoring or classification for an individual based on data such as a molecular profile. An individual's molecular profile can be compared to a broad spectrum of disease, disorder, or condition-associated profiles to generate one or more scores or matches using a classifier or model. The molecular profile can be a metabolite profile comprising one or more metabolites. The metabolites can be associated with one or more metabolic pathways such as, for example, lipid, carbohydrate, or protein metabolism. In some embodiments, the molecular profile comprises a metabolite profile, a protein/polypeptide profile, a gene expression profile, or any combination thereof. In some embodiments, the protein/polypeptide profile comprises quantification or abundance data for one or more proteins or polypeptides. In some embodiments, the gene expression profile comprises RNA sequencing data for one or more biomarkers.

The disease, disorder, or condition-associated profiles can correspond to a plurality of related classifications. In some cases, the related classifications share at least one common feature. In certain aspects, the algorithms described herein provide a classification that stratifies a disease, disorder, or condition. The stratification can be based on severity, grade, class, prognosis, or treatment of a particular disease, disorder, or condition, and/or other relevant factors. In some cases, a subject can be classified for a spectrum of a plurality of diseases, disorders, or conditions, which are optionally further classified into subcategories of the diseases, disorders, or conditions (e.g., subtypes or varying degrees of severity of a disease). For example, autoimmune diseases may be further subcategorized based on biomarkers such as one or more of the metabolite biomarkers disclosed herein.

An individual specimen such as a biological sample can be evaluated to generate a metabolite profile. The metabolite profile can be classified on a spectrum of a plurality of diseases, disorders, or conditions. In some cases, the classification is generated using classifiers trained using one or more machine learning algorithms. Sometimes, the classification comprises a score and/or indicator of the accuracy or confidence of the classification. In certain instances, the score is produced by ensemble machine learning methods, trained to a variety of complex patterns that are tightly associated with disease conditions reported by other individuals or patients. The classification can include a probability that a new sample belongs to a previously learned class of patient-reported outcomes.

The score can be used to evaluate individual disease states and track signs of progress or decline associated with given conditions and interventions, over periods of time. In some cases, a spectrum of multiple classifications are generated for an individual using one or more machine learning algorithms or classifiers. The spectrum of multiple classifications can comprise a plurality of classifications that are related, for example, sharing one or more common predictive features. As an example, MS and ALS share common features, which can lead to misclassification between MS and ALS positive cases. Thus, the generation of a spectrum of multiple classifications can help identify, resolve, and/or mitigate misclassifications between related diseases, disorders, or conditions. In some cases, a spectrum classification comprises a classification between two or more related classifications with a score and/or confidence or likelihood that the individual is positive for one or more of the related classifications. For example, the spectrum classification can be a score indicating a relative likelihood the individual has MS vs ALS (e.g., 35% MS score vs. 65% ALS score). In some instances, the spectrum classification comprises two or more of gastroesophageal reflux disease, bipolar disorder, amyotrophic lateral sclerosis, osteoarthritis, multiple sclerosis, fibromyalgia, systemic lupus erythematosus, generalized anxiety disorder, rheumatoid arthritis, major depressive disorder, high blood pressure hypertension, hypothyroidism, or post-traumatic stress disorder (see FIG. 2A-2B). In some instances, the spectrum classification comprises two, three, four, five, six, seven, eight, nine, ten, eleven, twelve, or thirteen diseases, disorders, or conditions selected from gastroesophageal reflux disease, bipolar disorder, amyotrophic lateral sclerosis, osteoarthritis, multiple sclerosis, fibromyalgia, systemic lupus erythematosus, generalized anxiety disorder, rheumatoid arthritis, major depressive disorder, high blood pressure hypertension, hypothyroidism, or post-traumatic stress disorder.

In some cases, the classifications for the plurality of multiple classification is output as a spectrum of various diseases, disorders, or conditions corresponding to the classifications. The output can be shown as a diagram indicating the score (e.g., as a percentage) of the individual overlaid over the "normal" score range corresponding to non-positive individuals (see FIG. 6A-6B). Thus, the output diagram can provide a simple and intuitive visual indication of whether the individual has or is at risk of developing one or more diseases, disorders, or conditions shown on the diagram. For example, the diagram in FIG. 6B shows that the individual has an osteoarthritis score that exceeds the normal range, thereby indicating the individual has or is at risk of developing osteoarthritis. Such diagrams are also useful for monitoring an individual over time, for example, allowing a simple visualization of an increase or decrease in score for a particular disease over time.

Metabolite profiles can be generated for two or more specimens obtained from an individual over a period of time. The metabolite profiles can be evaluated using the methods described herein to generate a classification or a spectrum of related classifications. The classification or spectrum of related classifications can be compared between specimens to assess an individual over a period of time. The period of time can be at least 1, 2, 3, 4, 5, 6, 7, 8, 9, 10, 15, 20, 25, 30, 35, 40, 45, 50, 55, 60 minutes and/or no more than 1, 2, 3, 4, 5, 6, 7, 8, 9, 10, 15, 20, 25, 30, 35, 40, 45, 50, 55, 60 minutes. In some cases, the period of time is at least 1, 2, 3, 4, 5, 6, 7, 8, 9, 10, 11, 12, 13, 14, 15, 16, 17, 18, 19, 20, 21, 22, 23, or 24 hours and/or no more than 1, 2, 3, 4, 5, 6, 7, 8, 9, 10, 11, 12, 13, 14, 15, 16, 17, 18, 19, 20, 21, 22, 23, or 24 hours. In certain instances, the period of time is at least 1, 2, 3, 4, 5, 6, or 7 days and/or no more than 1, 2, 3, 4, 5, 6, or 7 days. The period of time can be at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks and/or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks. Sometimes, the period of time is at least 1, 2, 3, 4, 5, 6, 7, 8, 9, or 10 years and/or no more than 1, 2, 3, 4, 5, 6, 7, 8, 9, or 10 years.

The accuracy, specificity, sensitivity, positive predictive value, negative predictive value, or any combination thereof may be determined for a classifier by testing it against a set of independent samples. True positive (TP) is a positive test result that detects the condition when the condition is present. True negative (TN) is a negative test result that does not detect the condition when the condition is absent. False positive (FP) is a test result that detects the condition when the condition is absent. False negative (FN) is a test result that does not detect the condition when the condition is present. Accuracy is defined by the formula: accuracy=(TP+TN)/(TP+FP+FN+TN). Specificity ("true negative rate") is defined by the formula: specificity=TN/(TN+FP). Sensitivity ("true positive rate") is defined by the formula: sensitivity=TP/(TP+FN). Positive predictive value (PPV or "precision") is defined by the formula: PPV=TP/(TP+FP). Negative predictive value (NPV) is defined by the formula: NPV=TN/(TN+FN).

In some cases, an individual or sample is classified with respect to one or more diseases, disorders, or conditions with an accuracy of at least about 80%, 85%, 90%, 95%, 96%, 97%, 98%, or 99% for at least 100, 150, or 200 independent samples. In some cases, an individual or sample is classified with respect to one or more diseases, disorders, or conditions with a specificity of at least about 80%, 85%, 90%, 95%, 96%, 97%, 98%, or 99% for at least 100, 150, or 200 independent samples. In some cases, an individual or sample is classified with respect to one or more diseases, disorders, or conditions with a sensitivity of at least about 80%, 85%, 90%, 95%, 96%, 97%, 98%, or 99% for at least 100, 150, or 200 independent samples. In some cases, an individual or sample is classified with respect to one or more diseases, disorders, or conditions with an AUC of at least about 0.80, 0.85 0.90, 0.95, 0.96, 0.97, 0.98, or 0.99 for at least 100, 150, or 200 independent samples.

Health data of an individual presented to a healthcare provider by the systems, media, or methods as described herein may include the diagnoses or classification, treatment regimen, and/or outcome of the individual. Non-limiting examples of health data presented to a healthcare provider may include metabolite data, classification, other data such as non-molecular/metabolite data, and therapeutic options.

In some embodiments an insight generated by the systems, media, or methods as described herein comprises one or more treatment regimens. For example, the system may present a treatment regimen to a healthcare provider that was deemed successful for subjects having metabolite profiles similar to that of the individual evaluated according to the systems, media, and methods described herein. A treatment regimen may be deemed successful, in some embodiments, when a goal of the patient is achieved through the application of the treatment regimen. An example of a treatment is diet, exercise, and statins for an individual determined to be overweight or obese and having atherosclerosis or heart disease.

Diseases, Disorders, and Conditions

Disclosed herein are algorithms, classifiers, or models that generate classifications of individuals based on input data. The classifications can correspond or relate to one or more diseases, disorders, or conditions. A disease can be identified as abnormalities or dysfunctions in systemic functions. A disorder can be identified as a disruption of the normal functions of the body. Accordingly, a disorder can be the resulting disruption caused by a disease in certain cases. A condition can be identified as an abnormal state of health, including states that interfere with normal activities or well-being of the individual. These categories may exhibit some overlap.

In some cases, the classification corresponds or relates to a neurological and/or autoimmune disease such as, for example, multiple sclerosis, systemic lupus erythematosus, or amyotrophic lateral sclerosis.

In some cases, the systems, media and methods disclosed herein provide a prediction or recommendation for treatment based on the classification or evaluation of one or more diseases, disorders, or conditions. In some cases, a report is generated comprising one or more findings such as the results of the classification or evaluation. In some cases, the report comprises or more diagnoses. In some cases, the report comprises one or more treatments or treatment recommendations. In some cases, the methods disclosed herein comprise providing treatment to the subject. In some instances, treatment is provided based at least on the classification or evaluation. The treatment can be a particular treatment for the one or more diseases, disorders, or conditions, for example, autoimmune diseases or disorders may be treated using an anti-inflammatory medication (e.g., acetaminophen, NSAIDs such as ibuprofen), corticosteroids (e.g., hydrocortisone, dexamethasone, prednisone, methylprednisolone, betamethasone), antimalarial drugs for skin and joint problems (e.g., hydroxychloroquine), immunosuppressants (e.g., azathioprine, mycophenolate mofetil, methotrexate), biologics such as antibodies (e.g., belimumab for treating SLE, and rituximab for treating MS, SLE, etc.), or any combination thereof. In some cases, the treatment comprises a drug treatment. Alternatively or in combination, the treatment comprises lifestyle changes such as to diet and/or exercise, or other non-pharmaceutical therapies. In some cases, the treatment comprises a drug treatment or therapy for a single disease, disorder, or condition identified according to the present disclosure. In some cases, the treatment comprises one or more drug treatments or therapies for multiple related diseases, disorders, or conditions.

In some cases, the treatment or treatment recommendation is generated for a subject who has not undergone treatment. In some cases, the subject is undergoing treatment and/or has previously been treated. In some cases, the classification or evaluation of a subject for one or more diseases, disorders, or conditions is used to monitor responsiveness to the treatment. For example, an algorithm or model that generates a result indicating severity or severity category for a disease, disorder, or condition may be used to evaluate a subject over time to determine whether the subject is responding to ongoing treatment as indicated by a decrease in severity over time. Accordingly, the systems and methods disclosed herein can include recommendations or steps to continue current treatment or therapy, cease treatment or therapy, or change/modify the current treatment or therapy (e.g., by changing a dose or adding another treatment).

In some instances, the systems and methods disclosed herein provide treatment(s) or treatment recommendation(s) for one or more diseases, disorders, or conditions selected from gastroesophageal reflux disease (e.g., antacids, H-2 receptor blockers such as cimetidine, famotidine, nizatidine, ranitidine, proton pump inhibitors such as esomeprazole, lansoprazole, omeprazole, pantoprazole, surgery), bipolar disorder (e.g., mood stabilizers such as valproic acid, antipsychotics such as Haldol decanoate, aripiprazole, olanzapine, risperidone, antidepressants such as selective serotonin reuptake inhibitors, citalopram, fluoxetine, paroxetine), amyotrophic lateral sclerosis (e.g., riluzole, edavarone, physical therapy, speech therapy), osteoarthritis (e.g., acetaminophen, NSAIDs, duloxetine, corticosteroids, surgery, physical therapy), multiple sclerosis (e.g., corticosteroids, such as prednisone and methylpredinisone, plasmapheresis, beta interferons, glatiramer acetate, fingolimod, teriflunomide, biologics such as ocrelizumab, natalizumab, alemtuzumab), fibromyalgia (acetaminophen, NSAIDs, antidepressants such as duloxetine, milnacipran, cyclobenzaprine, anti-seizure drugs such as gabapentin, pregabalin, physical therapy), systemic lupus erythematosus (acetaminophen, NSAIDs, steroid creams, corticosteroids, antimalarial drugs, immunotherapies), generalized anxiety disorder (e.g., antidepressants such as escitalopram, duloxetine, venlafaxine, paroxetine), rheumatoid arthritis (e.g., acetaminophen, NSAIDs, corticosteroids such as prednisone, disease modifying antirheumatic drugs (DMARMs) such as methotrexate, biologics such as adalimumab, certolizumab, etanercept, golimumab, occupational therapy, surgery), major depressive disorder (e.g., SSRIs, SNRIs, antidepressants, MAOIs), high blood pressure hypertension (e.g., angiotensin converting enzyme (ACE) inhibitors, beta-blockers, calcium channel blockers, alpha-blockers, alpha-agonists, renin inhibitors diuretics), hypothyroidism (e.g., synthetic levothyroxine), or post-traumatic stress disorder (e.g., antidepressants, anti-anxiety medication, prazosin, cognitive therapy, exposure therapy). Although an exhaustive list of pharmaceutical and non-pharmaceutical treatments is not provided for every disease, disorder, or condition described herein, the present disclosure contemplates any treatment known in the field for the diseases, disorders, or conditions including but not limited to treatments for those diseases, disorders, or conditions recited in Table 1.

The classifications can comprise conditions that are not necessarily associated with disease states. For example, a classification can include obesity, sleep deprivation, lack of exercise, oral health status, sleep apnea, and other health status indicators.

TABLE 1 shows non-limiting examples of diseases, disorders, and conditions.

abdominal adhesions
abdominal migraine
abdominal wall schwannoma
acanthosis nigricans
accidental fall
Achilles tendonosis
achondroplasia
ACL (anterior cruciate ligament) injury
acne
acoustic neuroma
acquired brain injury
acquired deformity of the ankle
actinic keratosis
acute angle-closure glaucoma
acute pericarditis
acute renal failure
acute respiratory distress syndrome
Addison's disease
adenocarcinoma (non-small cell lung cancer)
adenomyosis
adenosquamous carcinoma (non-small cell lung cancer)
adjustment disorder
adrenal adenoma
adrenal exhaustion
adrenal fatigue
adrenal insufficiency
adult apraxia of speech
aging
agoraphobia
Aicardi-Goutieres syndrome
alcohol use disorder
alexithymia
allergic asthma
allergic fungal sinusitis
allergic rhinitis
alopecia areata
alopecia universalis
alpha 1 antitrypsin deficiency
alternating hemiplegia of childhood
amyotrophic lateral sclerosis
anaesthesia dolorosa
anal fistula
anaphylaxis TABLE 1-continued shows non-limiting examples of diseases, disorders, and conditions.

anatomically narrow angle glaucoma
anatomically narrow angle without glaucoma
androgen deficiency
anemia of chronic disease
angina pectoris
angulation of the coccyx
anhidrosis
ankle sprain
ankylosing spondylitis
anorexia nervosa
anorexia nervosa binge eating purging type
anti-myelin associated glycoprotein polyneuropathy
antiphospholipid antibody syndrome
antisocial personality disorder
aortic aneurysm
aortic valve disorder
aortic valve regurgitation
aphakia
appendicitis
appendix cancer
arachnoid cyst
arachnoiditis
arachnophobia
arrhythmogenic right ventricular dysplasia
asbestosis
ascending cholangitis
Asperger's syndrome
aspiration pneumonia
aspirin induced asthma
asthma
astigmatism
atherosclerosis
atlantoaxial subluxation
atopic dermatitis
atrial fibrillation
atrial flutter
atrial septal defect
atrial tachycardia
attention deficit disorder
attention deficit/hyperactivity disorder
atypical choroid plexus papilloma
atypical depressive disorder
atypical facial pain
atypical hyperplasia of breast
atypical migraine
auditory processing disorder
autism spectrum disorder
autoimmune disease undefined
autoimmune hemolytic anemia
autoimmune hepatitis
autoimmune inner ear disease
autoimmune neutropenia
autoimmune pancreatitis
autoimmune progesterone dermatitis
autoimmune urticaria
autoimmune vasculitis
autonomic neuropathy
avoidant personality disorder
azygos vein stenosis
B cell prolymphocytic leukemia
Baastrup syndrome
bacterial conjunctivitis
bacterial overgrowth syndrome
bacterial vaginosis
Baker's cyst
balanced translocation
Barre-Lieou syndrome
Barrett's esophagus TABLE 1-continued shows non-limiting examples of diseases, disorders, and conditions.

basal cell skin cancer
battered person syndrome
Behcet's disease
Bell's palsy
below knee amputation (left)
below knee amputation (right)
benign adrenal tumor
benign brain tumor
benign breast tumor
benign fasciculation syndrome
benign ovarian tumor
benign paroxysmal positional vertigo
benign prostatic hyperplasia
benign retroperitoneal schwannoma
benzodiazepine withdrawal syndrome
bicep rupture
bicuspid aortic valve
bilateral vestibular hypofunction
bile duct obstruction
biliary reflux
binge eating disorder
bipolar disorder
bipolar I disorder
bipolar II disorder
Birt-Hogg-Dube syndrome
BK virus
bladder cancer
bladder infection (infective cystitis)
bladder ulcer
blepharitis
body dysmorphic disorder
bone marrow transplant
bone necrosis
bone spurs
borderline personality disorder
bowel obstruction
brachial plexus neuroma
brachioradial pruritus
brain aneurysm
brain damage in infancy
brain stem lesion
brain tumor
breast cancer
breast papilloma
broken ankle
broken arm (left)
broken arm (right)
broken clavicle
broken elbow (left)
broken elbow (right)
broken eye socket
broken foot
broken hand
broken hip (left)
broken hip (right)
broken jaw
broken knee
broken leg (left)
broken leg (right)
broken neck
broken nose
broken pelvis
broken ribs
broken shoulder
broken spine
broken toes
broken wrist
bronchiectasis
bronchiolitis obliterans
bronchitis
Brugada syndrome
bulimia nervosa
bullous emphysema TABLE 1-continued shows non-limiting examples of diseases, disorders, and conditions.

bullous pemphigoid
bundle branch block (right)
bunion
burning mouth syndrome
bursitis
burst fracture of spine
*C. diff* (*Clostridium difficile*) infection
candida (fungal) infection
car accident
carbon monoxide poisoning
cardiac arrest
cardiogenic shock
cardiomegaly
cardiomyopathy
carotid artery aneurysm
carotid artery dissection
carpal tunnel syndrome
cataplexy
cataracts
celiac disease
cellulitis
central pain syndrome
central sensitivity syndrome
central serous choroidopathy
central sleep apnea
central vertigo
cerebellar ataxia
cerebellar ataxia-neuropathy-vestibular areflexia syndrome
cerebral arteriovascular malformation
cerebral atrophy
cerebral malformation
cerebral palsy
cerebral small vessel disease
cerebral venous thrombosis
cerebrospinal fluid leak
cervical cancer
cervical dysplasia
cervical facet syndrome
cervical radiculopathy
cervical spondylosis
cervical vertebral subluxation
cervicitis
cervicogenic headache
cevical kyphosis
Charcot-Marie-Tooth disease
chemical menopause
chemical/venom allergy
Chiari malformation
chickenpox
chilblains
cholecystitis
cholesteatoma
cholinergic urticaria
chondromalacia patellae
chronic abdominal pain syndrome
chronic cerebrospinal venous insufficiency
chronic cutaneous lupus erythematosus
chronic diastolic heart failure
chronic Epstein-Barr
chronic headache disorder
chronic hyperglycemia
chronic idiopathic back pain
Chronic Idiopathic Constipation
chronic idiopathic hives
chronic inflammatory demyelinating polyneuropathy
chronic inflammatory response syndrome
chronic kidney disease
chronic lymphocytic leukemia
chronic mercury poisoning TABLE 1-continued shows non-limiting examples of diseases, disorders, and conditions.

chronic neuralgia
chronic obstructive bronchitis
chronic obstructive pulmonary
  disease
chronic pain syndrome
chronic pelvic pain syndrome
chronic pericarditis
chronic periodontitis
chronic recurrent multifocal
  osteomyelitis
chronic respiratory failure
chronic thromboembolic
  pulmonary hypertension
circadian rhythm sleep
  disorder
claustrophobia
cluster headaches
CNS lupus
cold sore (herpes simplex)
cold urticaria
colloid cysts
colon cancer
color blindness
coma
common variable
  immunodeficiency disorder
complex confusional migraine
complex migraine
complex post-traumatic stress
  disorder
complex regional pain
  syndrome type I
complex regional pain
  syndrome type II
complicated grief
compression fracture of spine
compulsive gambling
concussion
congenital afibrinogenemia
congenital anosmia
congenital cervical fusion
congenital disorders of
  glycosylation
congenital muscular dystrophy
  with arthrogryposis multiplex
  congenita
congenital nystagmus
congenital rubella
congenital spinal stenosis
congestive heart failure
Conn's syndrome
conversion disorder
corneal abrasion
corneal map-dot-fingerprint
  dystrophy
coronary artery disease
cortical blindness
corticobasal degeneration
costochondritis
cough variant asthma
CREST syndrome
critical illness polyneuropathy
Crohn's disease
cryptococcal pneumonia
cryptogenic cirrhose
cryptogenic organizing
  pneumonia
cubital tunnel syndrome
Cushing's disease
Cushing's syndrome
cyclic vomiting syndrome
cyclical neutropenia
cyclothymia
cystic fibrosis
cystic fibrosis-related diabetes
cystocele
cytomegalovirus TABLE 1-continued shows non-limiting examples of diseases, disorders, and conditions.

DCIS (Ductal carcinoma in
  situ)
de Quervain syndrome
decompression sickness
deep vein thrombosis
degenerative disc disease
degenerative myopia
delayed sleep phase syndrome
demyelinating disease of
  central nervous system
dengue
dental cavities
dentinogenesis imperfecta
dependent personality disorder
depersonalization disorder
Dercum's disease
dermatillomania
dermatographism
dermatomyositis
desquamative interstitial
  pneumonia
developmental delay
developmental language
  disorder
developmental trauma disorder
developmental venous
  anomaly
deviated nasal septum
diabetes insipidus
diabetes type 1
diabetes type 2
diabetic ketoacidosis
diabetic neuropathy
diabetic retinopathy
diastolic dysfunction
diffuse idiopathic skeletal
  hyperostosis
dilated cardiomyopathy
discoid lupus erythematosus
discoid meniscus
dislocated elbow (left)
dislocated thumb
dislocation of hip (left)
disruptive mood dysregulation
  disorder
dissociative identity disorder
diverticulitis
diverticulosis
DRESS syndrome
drug use disorder
dry eye syndrome
Duchenne muscular dystrophy
duodenal ulcer
Dupuytren's contracture
dysarthria
dysautonomia
dyshidrotic eczema
dyslexia
dysmenorrhea
dyspareunia
dysphasia
dystonia
*E. coli* infection
early onset dementia
eating disorder
Ebstein's anomaly
ectopic pregnancy
eczema
Ehlers-Danlos syndrome
elbow schwannoma
emphysema
encephalitis
endocarditis
endometrial cancer
endometrial intraepithelial
  neoplasia
endometriosis
eosinophilic esophagitis TABLE 1-continued shows non-limiting examples of diseases, disorders, and conditions.

eosinophilic polymyositis
epigastric hernia
epilepsy
episcleritis
episodic ataxia
erectile dysfunction
erosive osteoarthritis
erythromelalgia
esophageal achalasia
esophageal diverticulum
esophageal dysphagia
esophageal spasms
esophagitis
essential myoclonus
essential thrombocythemia
essential tremor
eustachian tube dysfunction
Evans syndrome
exotropia
facet joint osteoarthritis
factor V Leiden
factor VIII elevation
factor XIII deficiency
failed back syndrome
familial adenomatous
polyposis
familial hypercholesterolemia
familial mediterranean fever
fat malabsorption
female infertility
female pattern baldness
femoral acetabular
impingement-cam type
femoral anteversion
femoral hernia
fibrocystic breast tissue
fibromuscular dysplasia
fibromyalgia
fibrous dysplasia
finger amputation
flat feet (pes planus)
focal dystonia
folate deficiency anemia
follicular thyroid cancer
food additive allergy
food allergy
foot schwannoma
foot stress fracture
foreign accent syndrome
fractured calcaneus
fractured fingers
fractured tailbone
frontal fibrosing alopecia
frontotemporal dementia
fructose malabsorption
Fuchs' dystrophy
functional dyspepsia
functional movement disorder
functional neurologic symptom
disorder
fungal meningitis
gallstones
ganglion cyst
gastric antral vascular ectasia
gastric ulcer
gastritis
gastroesophageal reflux
disease
gastrointestinal fistula
gastrointestinal polyps
gastroparesis
gastroschisis
gender dysphoria
generalized anxiety disorder
genital herpes
Gilbert's syndrome
gingivitis
Glanzmann's thrombasthenia TABLE 1-continued shows non-limiting examples of diseases, disorders, and conditions.

glaucoma
glioblastoma
glomerulonephritis
glomus tympanicum jugulare
paraganglioma
glossopharyngeal neuralgia
glucose 6 phosphate
dehydrogenase deficiency
glucose transporter type 1
deficiency
glycogen storage disease
gonorrhea
gout
granuloma annulare
granulomatosis with
polyangiitis (Wegener's)
Graves' disease
growth hormone deficiency
gynecomastia
*H. pylori*
H1N1 influenza A
Haglund's deformity
hallux rigidus
Hashimoto encephalitis
Hashimoto's thyroiditis
head contusion
hearing loss
heart attack (myocardial
infarction)
heart block
heart failure
heart murmur
heart transplant
heavy metal toxicity
hemifacial spasm
hemiplegia
hemiplegic migraine
hemochromatosis
hemolytic anemia
hemophilia A
hemorrhoids
hepatic encephalopathy
hepatitis B
hepatitis C
hereditary fructose intolerance
hereditary hemorrhagic
telangiectasia
hereditary spastic paraplegia
hereditary spherocytosis
herniated disc
herpes simplex virus infection
herpes zoster ophthalmicus
hiatal hernia
hidradenitis suppurativa
high arches (pes cavus)
high blood pressure
(hypertension)
high cholesterol
(hypercholesterolemia)
hip bursitis
hip disarticulation (right)
hip dysplasia
hip labral tear
histamine intolerance
(histaminosis)
histoplasmosis
hormonal imbalance
human immunodeficiency
virus (HIV)
human papillomavirus
infection
Huntington's disease
hydrocephalus
hyperacusis
hypercalcemia
hyperhidrosis disorder
hyperinsulinemia
hyperinsulinemic TABLE 1-continued shows non-limiting examples of diseases, disorders, and conditions.

hypoglycemia with nesidioblastosis
hyperkalemia
hyperkyphosis
hyperlipidemia
hypermobility syndrome
hyperparathyroidism
hypersensitivity pneumonitis
hypersensitivity vasculitis
hyperthyroidism
hypertonic pelvic floor dysfunction
hypertriglyceridemia
hypertrophic obstructive cardiomyopathy
hypochondria
hypogammaglobulinemia
hypogonadism
hypokalemia
hypokalemic periodic paralysis
hypomania
hypoparathyroidism
hypotension
hypothyroidism
hypoxemia
ice pick headache
idiopathic adhesive capsulitis
idiopathic angioedema
idiopathic hypersomnia
idiopathic intracranial hypertension
idiopathic leukocytosis
idiopathic polymorphic ventricular tachycardia
idiopathic pulmonary arterial hypertension
idiopathic pulmonary fibrosis
idiopathic thrombocytopenia purpura
IgA deficiency
IgA nephropathy
IgE deficiency
IgG deficiency
iliac vein compression syndrome
iliotibial band syndrome
inappropriate sinus tachycardia
inclusion body myositis
indeterminate colitis
indolent systemic mastocytosis
infection of uncertain origin
infectious colitis
inferior alveolar nerve damage
influenza (the "flu")
infracalcaneal bursitis
ingrown hair
inguinal hernia
inherited pressure palsy neuropathy
insomnia
internal jugular vein stenosis
internuclear ophthalmoplegia
intersex
interstitial cystitis
interstitial lung disease
intestinal arteriovenous malformation
intracranial hemorrhage
invasive lobular carcinoma
iritis
Irlen syndrome
iron deficiency anemia
irritable bladder syndrome
irritable bowel syndrome
ischemia stroke
ischemic colitis
jock itch
keloid scar
keratitis
keratoconus
keratosis pilaris
kidney cyst
kidney stone
kidney transplant
kidney transplant rejection
Kikuchi disease
Klinefelter syndrome
knee injury
kneecap (patellar) dislocation
knock kneed
kyphoscoliosis
labile hypertension
labyrinthitis
lactose intolerance
laryngeal cancer
laryngopharyngeal reflux
leaky gut syndrome
Leber's optic atrophy
left ventricular hypertrophy
left ventricular systolic dysfunction
leukopenia
Lewy body disease
lichen planus
lichen sclerosus
lichen simplex chronicus
lipedema
lipoma(s)
liver cirrhosis
liver cysts
liver enlargement
liver impairment
liver toxicity
Lobular Carcinoma In Situ
logopenic progressive aphasia
long qt syndrome
longsightedness
lordosis
loss of loved one
low calcium (hypocalcemia)
lumbar disc annular tear
lumbar radiculopathy
lumbar spondylosis
lumbosacral radiculopathy
lung collapse (atelectasis)
lung nodules
lung transplant
lupus nephritis
lupus pneumonitis
lupus profundus
Lyme disease
lymphedema
lymphomatoid papuplosis
macular degeneration
macular drusen
macular edema
macular fibrosis
major depressive disorder
maladaptive daydreaming
malignant hyperthermia
Marfan syndrome
mast cell activation syndrome
mastitis
math learning disability
medial collateral ligament tear
medial epicondylitis
medullary sponge kidney
medullary thyroid cancer
meibomian gland dysfunction
melanoma
melorheostosis
Meniere's disease
meningioma
menopause
menorrhagia
meralgia paresthetica TABLE 1-continued shows non-limiting examples of diseases, disorders, and conditions.

metabolic syndrome
metal allergy
metallosis
metastatic melanoma
metathesiophobia
methicillin-resistant *Staphylococcus aureus*
methylenetetrahydrofolate reductase deficiency
microscopic colitis
microvascular angina
microvascular disease
mid foot sprain
migraine
migraine with brainstem aura
mild depression
military sexual trauma
miscarriage
mitochondrial disease
mitral valve disorder
mitral valve prolapse
mitral valve regurgitation
mitral valve stenosis
mixed connective tissue disease
mixed tension migraine
Mollaret's meningitis
monoclonal gammopathy of undetermined significance
mononucleosis
Morton's neuroma
mosaic 13q12.2-34 deletion
mucous cyst
multifocal motor neuropathy
multiple chemical sensitivity
multiple myeloma
multiple sclerosis
multiple system atrophy
mumps
muscle tension dysphonia
muscular dystrophy
musculocutaneous neuropathy
myalgic encephalomyelitis/chronic fatigue syndrome
myasthenia gravis
mycobacterium avium complex
myelopathy
myeloproliferative disorder
myoclonic dystonia
myofascial pain syndrome
myopathy
myositis
nail fungus
narcolepsy
nasal polyps
nasal turbinate hypertrophy
natural killer cell deficiency syndrome
nephropathy C1q
nervous breakdown
neurally mediated hypotension
neuroendocrine tumor
neurofibromatosis
neurogenic bladder
neurogenic bowel disorder
neuromyelitis optica
neurosarcoidosis
nevus anemicus
new daily persistent headache
nightmare disorder
non-alcoholic fatty liver disease
non-allergic rhinitis
non-celiac gluten intolerance
non-diabetic hypoglycemia
non-Hodgkin's lymphoma
non-progressive mild cognitive impairment
non-small cell lung cancer
nonalcoholic steatohepatitis
nondiabetic lumbosacral radiculoplexus neuropathy
nonverbal learning disability
normal pressure hydrocephalus
Nutcracker syndrome
obesity
obsessive compulsive hoarding disorder
obsessive compulsive personality disorder
obsessive-compulsive disorder
obstructive sleep apnea
occipital neuralgia
ocular hypertension
ocular migraine
ophthalmic rosacea
optic disc drusen
optic neuritis
oral allergy syndrome
oral lichen planus
organic brain syndrome
orthostatic hypotension
ossification of the posterior longitudinal ligament
osteoarthritis
osteogenesis imperfecta
osteomyelitis
osteopenia
osteoporosis
other specified dissociative disorder
otosclerosis
ovarian cancer
ovarian cyst
ovarian torsion
overeating disorder
Paget-Schroetter syndrome
Paget's disease of bone
painful legs and moving toes syndrome
palmoplantar pustulosis
pancreas divisum
pancreatic insufficiency
pancreatitis
pancreatogenous diabetes
panhypopituitarism
panic disorder
papillary thyroid carcinoma
papilledema
paranoid personality disorder
paranoid schizophrenia
paraovarian cysts
Parkinson's disease
parotid gland tumor
paroxysmal dyskinesia
passive aggressive personality disorder
patellar tracking disorder
patellofemoral pain syndrome
patent foramen ovale
pattern macular dystrophy
pelvic congestion syndrome
pelvic floor dyssynergia
pelvic inflammatory disease
pelvic organ prolapse
pelvic schwannoma
pelvic torsion
pemphigus
perennial allergy
pericardial cyst
pericardial effusion
perimenopause
perineal laceration during childbirth TABLE 1-continued shows non-limiting examples of diseases, disorders, and conditions.

periodic limb movement disorder
periodontal disease
perioral dermatitis
peripheral arterial disease
peripheral neuropathy
peripheral retinal degeneration
pernicious anemia
persistent depressive disorder (dysthymia)
personality disorder
petechiae
phimosis
phleboliths
phobic disorder
photodermatitis
phyllodes tumor
pigmentary dispersion syndrome
pineal gland cyst
piriformis syndrome
pituitary adenoma
pituitary deficiency
placenta accreta
placenta percreta
placenta previa
plantar fascial fibromatosis
plantar fasciitis
pleural effusion
pleurisy
pneumonia
poikilothermia
polyarteritis nodosa
polyarticular onset juvenile arthritis
polycystic kidney disease
polycystic ovary syndrome
polycythemia vera
polymyalgia rheumatica
polymyositis
portal hypertension
post intensive care unit syndrome
post-polio syndrome
post-concussion syndrome
post-surgical malabsorption
post-traumatic headache
post-traumatic stress disorder
post-treatment Lyme disease syndrome
posterior cruciate ligament injury
posterior tibial tendon dysfunction
postherpetic neuralgia
postmenopause
postpartum depression
postpartum psychosis
postural orthostatic tachycardia syndrome
pre-glaucoma
prediabetes
preeclampsia/eclampsia
pregnancy
prehypertension
premature atrial contractions
premature birth
premature menopause
premature ovarian failure
premature ventricular contractions
premenstrual dysphoric disorder
primary amenorrhea
primary biliary cholangitis
primary hyperhidrosis
primary lateral sclerosis
primary orthostatic tremors
primary progressive aphasia
primary spontaneous pneumothorax
Prinzmetal angina
progressive bulbar palsy
progressive muscular atrophy
progressive supranuclear palsy
prolactinoma
prosopagnosia
prostate cancer
protein S deficiency
prothrombin 20210 mutation thrombophilia
proximal myopathy
proximal neuropathy
pseudocyst
pseudodementia
psoriasis
psoriatic arthritis
psychogenic non-epileptic seizures
psychosis disorder
psychotic depression
pulmonary aneurysm
pulmonary edema
pulmonary embolism
pulmonary fibrosis
pulmonary hypertension
pulmonary sarcoidosis
pulmonary toxicity
pulmonary valve stenosis
pure autonomic failure
pyloric stenosis
pyroluria syndrome
quadriplegia
radiation exposure
radiculopathy
rage disorder
Rathke cleft cyst
Raynaud's disease
reactive airways dysfunction syndrome
reactive arthritis
reactive attachment disorder
reactive depression
reactive hypoglycemia
reactive thrombocytosis
rectal outlet dysfunction
rectal prolapse
rectocele
red skin syndrome/topical steroid withdrawal
redundant colon
REM sleep behavior disorder
renal artery stenosis
renal cell cancer
repetitive stress injury
residual schizophrenia
respiratory syncytial virus (RSV) infection
restless legs syndrome
restrictive lung disease
retained placenta
retinal detachment
retroperitoneal hernia
Reynolds syndrome
rhabdomyolysis
rheumatic fever
rheumatoid arthritis
rheumatoid lung disease
rib dysfunction
rocky mountain spotted fever
rosacea
rotator cuff syndrome
rupture of colon
rupture of spleen
ruptured hand tendon
sacroiliac joint dysfunction
sacroiliitis TABLE 1-continued shows non-limiting examples of diseases, disorders, and conditions.

salivary gland cancer
sarcoidosis
Scheuermann's kyphosis
schizoaffective disorder
schizoid personality disorder
schizophrenia
Schmorl's nodes
schwannoma of spinal cord
sciatic neuralgia
scleroderma
scoliosis
seasonal affective disorder
seasonal allergy
seborrheic dermatitis
Seborrheic Psoriasis
secondary hypogonadism
secondary immunodeficiency disorder
secondary polycythemia
sensory processing disorder
separation anxiety disorder
sepsis
serotonin deficiency syndrome
serotonin syndrome
severe combined immunodeficiency disease
sex addiction
sexual abuse
shared psychotic disorder
shingles (herpes zoster)
shortsightedness
shoulder injury
shoulder subluxation
SIADH
sialolithiasis
sickle cell disease
silent migraine
sinus bradycardia
sinus infection (sinusitis)
sinus node dysfunction
sinus tachycardia
sinus tarsi syndrome
Sjogren-Larsson syndrome
Sjogren's syndrome
skull fracture
sleep apnea disorder
sleep paralysis
sleep walking (somnambulism)
slow transit constipation
small cell lung cancer
small fiber sensory neuropathy
snapping hip disorder
social anxiety disorder
solar urticaria
somatization disorder
spasmodic dysphonia
spastic diplegia cerebral palsy
species dysphoria
speech disorder
sphenoid sinusitis
sphincter of Oddi dysfunction
spina bifida
spina bifida occulta
spinal accessory nerve injury
spinal cord injury
spinal hemangioma
spinal meningitis
spinal myoclonus
spinal stenosis
splenic artery aneurysm
splenomegaly
spondyloarthropathy
spondylolisthesis
spondylosis
squamous cell skin cancer
statin-induced myopathy
status migrainosus
steroid-induced diabetes
mellitus
steroid-induced myopathy
Stevens Johnson syndrome
stiff person syndrome
stillbirth
stomach cancer
stomach flu (gastroenteritis)
storage pool disease
strabismus amblyopia
strep throat
stroke
subacute cutaneous lupus erythematosus
subacute thyroiditis
subdural hematoma
superior mesenteric artery syndrome
supraventricular tachycardia
surgical menopause
Sweet syndrome
synovial cyst
syringomyelia
systemic candidiasis
systemic inflammatory response syndrome
systemic lupus erythematosus
Systemic Mast Cell Disorder (SMCD)
systemic onset juvenile arthritis
systemic vasculitis
tailor's bunion
tardive dyskinesia
Tarlov cyst
tarsal tunnel syndrome
telangiectasia macularis eruptiva perstans
telangiectasias
temporal arteritis
temporomandibular joint disc dislocation
temporomandibular joint syndrome
tendinitis
tendinopathy
tendonosis
tennis elbow (lateral epicondylitis)
tenosynovitis
tension headache
terminal esophageal web
testicular cancer
tethered cord syndrome
thalassemia
third degree burns
thoracic outlet syndrome
thoracic radiculopathy
thoracic spondylosis
thrombocytopathy
thrombotic thrombocytopenia purpura
thyroid cancer
thyroid nodule
Tietze's syndrome
tinea corporis
tinnitus
tobacco use disorder
toe amputation (left)
toe amputation (right)
tonsillitis
tooth abscess
tooth fractures
torn meniscus of knee
torticollis
Tourette syndrome
toxic encephalopathy
toxoplasmosis
tracheobronchomalacia
transient ischemic attack

TABLE 1-continued shows non-limiting examples of diseases, disorders, and conditions.

transient osteoporosis of hip
transverse myelitis
traumatic brain injury
trichotillomania
tricuspid valve regurgitation
trigeminal neuralgia
trimalleolar fracture
tuberculosis
Turner's syndrome
twisted bowel (intestinal volvulus)
typhlitis
ulcerative colitis
ulnar tunnel syndrome
umbilical hernia
undifferentiated connective tissue disease
undifferentiated inflammatory arthritis
unilateral vestibular hypofunction
unspecified dissociative disorder
upper airway resistance syndrome
urethral stricture
urge incontinence
urinary incontinence
urinary tract infection
urosepsis
uterine cancer
uterine fibroids
uterine polyp
uveitis
vaginismus
vagus nerve schwannoma
valvular heart disease
varicose veins of legs
vasovagal syncope
venous insufficiency
ventral hernia
ventribular fibrillation
ventricular septal defect
ventricular tachycardia
vestibular migraine
viral meningitis
vision loss
vitamin A deficiency
vitamin B12 deficiency
vitamin B2 deficiency
vitamin B6 deficiency
vitamin D deficiency
vitiligo
vocal cord dysfunction
vocal cord pharyngeal distal myopathy
von Willebrand disease
vulvar vestibulitis
vulvodynia
West Nile virus
whiplash
white matter disease
whooping cough
Wolff-Parkinson-White syndrome
written expression learning disability
xanthelasma Biological Samples In some aspects, the algorithms, models, or classifiers described herein utilize data derived from biological samples. Biological samples include any biological material from which biomolecules such as metabolites can be prepared and examined. Non-limiting examples include whole blood, plasma, saliva, cheek swab, fecal material, urine, cell mass, biopsy, or any other bodily fluid or tissue.

Metabolites

In some aspects, the algorithms, models, or classifiers described herein are configured to generate a classification or a spectrum of related classifications based on data such as metabolite data. The metabolite data can be obtained from a biological sample of an individual using various molecular detection techniques described herein. The metabolites can be implicated in one or more metabolic pathways. Metabolites include small molecules present in the cells, tissues, organs, and/or fluids that are involved in metabolism. A metabolite can be an intermediate end product of a metabolic pathway or process. Metabolites can have various functions, including use as a source of energy (e.g., ATP), a metabolic building block (e.g., acetyl coenzyme A), signaling, and other molecular pathways.

Metabolites can include components of biochemical classes of molecules such as amino acids, monosaccharides, nucleotides, and fatty acids/glycerol and other building blocks of proteins, carbohydrates, nucleic acids, and lipids, respectively. Metabolites can include coenzymes such as adenosine triphosphate (ATP) and nicotinamide adenine dinucleotide (NADH or NADPH) which play roles in various biochemical anabolic and catabolic reactions. Table 2 shows a non-limiting list of metabolites that can be evaluated by the algorithms described herein to generate one or more classifications of diseases, disorders, or conditions. In some cases, the panel of biomarkers used to classify or evaluate the status of a disease, disorder, or condition as disclosed herein comprises one or more metabolites selected from Table 2. In some cases, the panel of biomarkers comprises at least 1, 2, 3, 4, 5, 6, 7, 8, 19, 10, 15, 20, 25, 30, 35, 40, 45, 50, 60, 70, 80, 90, 100, 150, 200, 250, 300, 350, 400, 450, 500, 550, 600, 650, 700, 750, 800, 850, 900, or 950 or more metabolites from Table 2. In some cases, the panel of biomarkers comprises no more than 1, 2, 3, 4, 5, 6, 7, 8, 19, 10, 15, 20, 25, 30, 35, 40, 45, 50, 60, 70, 80, 90, 100, 150, 200, 250, 300, 350, 400, 450, 500, 550, 600, 650, 700, 750, 800, 850, 900, or 950 or more metabolites from Table 2. In some embodiments, the panel of biomarkers comprises a subset of metabolites selected from Table 2 that satisfy a threshold or performance metric as disclosed herein, for example, a correlation or association with one or more diseases, disorders, or conditions of interest having a certain p-value or metric such as PPV or AUC.

TABLE 2

| Probe name | platform | data_type | official_symbol | EGID/COMP_ID |
| --- | --- | --- | --- | --- |
| mlon_1101 | mlon | metabolomics | homovanillate (HVA) | 1101 |
| mlon_1105 | mlon | metabolomics | linoleate (18:2n6) | 1105 |
| mlon_1107 | mlon | metabolomics | allantoin | 1107 |
| mlon_1110 | mlon | metabolomics | arachidonate (20:4n6) | 1110 |
| mlon_1114 | mlon | metabolomics | deoxycholate | 1114 |
| mlon_1118 | mlon | metabolomics | arachidate (20:0) | 1118 |

TABLE 2-continued

| Probe name | platform | data_type | official_symbol | EGID/COMP_ID |
|---|---|---|---|---|
| mlon_1121 | mlon | metabolomics | margarate (17:0) | 1121 |
| mlon_1123 | mlon | metabolomics | inosine | 1123 |
| mlon_1124 | mlon | metabolomics | myo-inositol | 1124 |
| mlon_1125 | mlon | metabolomics | isoleucine | 1125 |
| mlon_1126 | mlon | metabolomics | alanine | 1126 |
| mlon_12017 | mlon | metabolomics | 3-methoxytyrosine | 12017 |
| mlon_12032 | mlon | metabolomics | 4-acetamidophenol | 12032 |
| mlon_12122 | mlon | metabolomics | naproxen | 12122 |
| mlon_12129 | mlon | metabolomics | beta-hydroxyisovalerate | 12129 |
| mlon_12261 | mlon | metabolomics | taurodeoxycholate | 12261 |
| mlon_1284 | mlon | metabolomics | threonine | 1284 |
| mlon_1299 | mlon | metabolomics | tyrosine | 1299 |
| mlon_1301 | mlon | metabolomics | lysine | 1301 |
| mlon_1302 | mlon | metabolomics | methionine | 1302 |
| mlon_1303 | mlon | metabolomics | malate | 1303 |
| mlon_1336 | mlon | metabolomics | palmitate (16:0) | 1336 |
| mlon_1356 | mlon | metabolomics | nonadecanoate (19:0) | 1356 |
| mlon_1358 | mlon | metabolomics | stearate (18:0) | 1358 |
| mlon_1361 | mlon | metabolomics | pentadecanoate (15:0) | 1361 |
| mlon_1365 | mlon | metabolomics | myristate (14:0) | 1365 |
| mlon_1412 | mlon | metabolomics | 2'-deoxyuridine | 1412 |
| mlon_1414 | mlon | metabolomics | 3-phosphoglycerate | 1414 |
| mlon_1417 | mlon | metabolomics | kynurenate | 1417 |
| mlon_1418 | mlon | metabolomics | 5,6-dihydrothymine | 1418 |
| mlon_1419 | mlon | metabolomics | 5-methylthioadenosine (MTA) | 1419 |
| mlon_1432 | mlon | metabolomics | 2-hydroxyphenylacetate | 1432 |
| mlon_1437 | mlon | metabolomics | succinate | 1437 |
| mlon_1444 | mlon | metabolomics | pipecolate | 1444 |
| mlon_1493 | mlon | metabolomics | ornithine | 1493 |
| mlon_1494 | mlon | metabolomics | 5-oxoproline | 1494 |
| mlon_1496 | mlon | metabolomics | methylmalonate (MMA) | 1496 |
| mlon_1498 | mlon | metabolomics | N6,N6,N6-trimethyllysine | 1498 |
| mlon_1505 | mlon | metabolomics | orotate | 1505 |
| mlon_1508 | mlon | metabolomics | pantothenate (Vitamin B5) | 1508 |
| mlon_1512 | mlon | metabolomics | picolinate | 1512 |
| mlon_15122 | mlon | metabolomics | glycerol | 15122 |
| mlon_15136 | mlon | metabolomics | xanthosine | 15136 |
| mlon_15140 | mlon | metabolomics | kynurenine | 15140 |
| mlon_1515 | mlon | metabolomics | salicylate | 1515 |
| mlon_1516 | mlon | metabolomics | sarcosine | 1516 |
| mlon_1519 | mlon | metabolomics | sucrose | 1519 |
| mlon_15336 | mlon | metabolomics | tartarate | 15336 |
| mlon_15443 | mlon | metabolomics | glucuronate | 15443 |
| mlon_1549 | mlon | metabolomics | 3-hydroxyisobutyrate | 1549 |
| mlon_15500 | mlon | metabolomics | carnitine | 15500 |
| mlon_15506 | mlon | metabolomics | choline | 15506 |
| mlon_1552 | mlon | metabolomics | erucate (22:1n9) | 1552 |
| mlon_1558 | mlon | metabolomics | 4-acetamidobutanoate | 1558 |
| mlon_15581 | mlon | metabolomics | xylose | 15581 |
| mlon_15586 | mlon | metabolomics | maltose | 15586 |
| mlon_1561 | mlon | metabolomics | alpha-tocopherol | 1561 |
| mlon_1563 | mlon | metabolomics | chenodeoxycholate | 1563 |
| mlon_1564 | mlon | metabolomics | citrate | 1564 |
| mlon_15650 | mlon | metabolomics | 1-methyladenosine | 15650 |
| mlon_1566 | mlon | metabolomics | 3-aminoisobutyrate | 1566 |
| mlon_15667 | mlon | metabolomics | 2-isopropylmalate | 15667 |
| mlon_1567 | mlon | metabolomics | vanillylmandelate (VMA) | 1567 |
| mlon_15676 | mlon | metabolomics | 3-methyl-2-oxovalerate | 15676 |
| mlon_15677 | mlon | metabolomics | 3-methylhistidine | 15677 |
| mlon_15679 | mlon | metabolomics | xanthurenate | 15679 |
| mlon_15681 | mlon | metabolomics | 4-guanidinobutanoate | 15681 |
| mlon_15685 | mlon | metabolomics | 5-hydroxylysine | 15685 |
| mlon_15705 | mlon | metabolomics | cystathionine | 15705 |
| mlon_15716 | mlon | metabolomics | imidazole lactate | 15716 |
| mlon_1572 | mlon | metabolomics | glycerate | 1572 |
| mlon_15720 | mlon | metabolomics | N-acetylglutamate | 15720 |
| mlon_15736 | mlon | metabolomics | 4-acetamidophenylglucuronide | 15736 |
| mlon_15745 | mlon | metabolomics | methylsuccinate | 15745 |
| mlon_15749 | mlon | metabolomics | 3-phenylpropionate (hydrocinnamate) | 15749 |
| mlon_15753 | mlon | metabolomics | hippurate | 15753 |
| mlon_15765 | mlon | metabolomics | ethylmalonate | 15765 |
| mlon_15772 | mlon | metabolomics | ribitol | 15772 |
| mlon_15778 | mlon | metabolomics | benzoate | 15778 |
| mlon_1584 | mlon | metabolomics | methyl indole-3-acetate | 1584 |
| mlon_1585 | mlon | metabolomics | N-acetylalanine | 1585 |
| mlon_1587 | mlon | metabolomics | N-acetylleucine | 1587 |
| mlon_1589 | mlon | metabolomics | N-acetylmethionine | 1589 |
| mlon_1591 | mlon | metabolomics | N-acetylvaline | 1591 |

TABLE 2-continued

| Probe name | platform | data_type | official_symbol | EGID/COMP_ID |
|---|---|---|---|---|
| mlon_15958 | mlon | metabolomics | phenylacetate | 15958 |
| mlon_15990 | mlon | metabolomics | glycerophosphorylcholine (GPC) | 15990 |
| mlon_1600 | mlon | metabolomics | phosphoethanolamine (PE) | 1600 |
| mlon_1604 | mlon | metabolomics | urate | 1604 |
| mlon_1605 | mlon | metabolomics | ursodeoxycholate | 1605 |
| mlon_1638 | mlon | metabolomics | arginine | 1638 |
| mlon_1642 | mlon | metabolomics | caprate (10:0) | 1642 |
| mlon_1643 | mlon | metabolomics | fumarate | 1643 |
| mlon_1644 | mlon | metabolomics | heptanoate (7:0) | 1644 |
| mlon_1645 | mlon | metabolomics | laurate (12:0) | 1645 |
| mlon_1648 | mlon | metabolomics | serine | 1648 |
| mlon_1649 | mlon | metabolomics | valine | 1649 |
| mlon_1651 | mlon | metabolomics | pyridoxal | 1651 |
| mlon_1669 | mlon | metabolomics | 4-hydroxyphenylpyruvate | 1669 |
| mlon_1670 | mlon | metabolomics | urea | 1670 |
| mlon_1712 | mlon | metabolomics | cortisol | 1712 |
| mlon_1769 | mlon | metabolomics | cortisone | 1769 |
| mlon_17747 | mlon | metabolomics | sphingosine | 17747 |
| mlon_17769 | mlon | metabolomics | sphinganine | 17769 |
| mlon_17799 | mlon | metabolomics | ibuprofen | 17799 |
| mlon_17805 | mlon | metabolomics | dihomolinoleate (20:2n6) | 17805 |
| mlon_17945 | mlon | metabolomics | 2-hydroxystearate | 17945 |
| mlon_18037 | mlon | metabolomics | metoprolol | 18037 |
| mlon_1806 | mlon | metabolomics | retinol (Vitamin A) | 1806 |
| mlon_18245 | mlon | metabolomics | gamma-glutamylhistidine | 18245 |
| mlon_18254 | mlon | metabolomics | paraxanthine | 18254 |
| mlon_18280 | mlon | metabolomics | gentisate | 18280 |
| mlon_18281 | mlon | metabolomics | 2-hydroxyhippurate (salicylurate) | 18281 |
| mlon_18335 | mlon | metabolomics | quinate | 18335 |
| mlon_18349 | mlon | metabolomics | indolelactate | 18349 |
| mlon_18362 | mlon | metabolomics | azelate (nonanedioate; C9) | 18362 |
| mlon_18368 | mlon | metabolomics | cys-gly, oxidized | 18368 |
| mlon_18369 | mlon | metabolomics | gamma-glutamylleucine | 18369 |
| mlon_18374 | mlon | metabolomics | methionine sulfoxide | 18374 |
| mlon_18392 | mlon | metabolomics | theobromine | 18392 |
| mlon_18394 | mlon | metabolomics | theophylline | 18394 |
| mlon_18467 | mlon | metabolomics | eicosapentaenoate (EPA; 20:5n3) | 18467 |
| mlon_18474 | mlon | metabolomics | estrone 3-sulfate | 18474 |
| mlon_18476 | mlon | metabolomics | glycocholate | 18476 |
| mlon_18477 | mlon | metabolomics | glycodeoxycholate | 18477 |
| mlon_18494 | mlon | metabolomics | taurochenodeoxycholate | 18494 |
| mlon_18497 | mlon | metabolomics | taurocholate | 18497 |
| mlon_1868 | mlon | metabolomics | cysteine | 1868 |
| mlon_1898 | mlon | metabolomics | proline | 1898 |
| mlon_1899 | mlon | metabolomics | quinolinate | 1899 |
| mlon_19130 | mlon | metabolomics | 1,2-dipalmitoyl-GPC (16:0/16:0) | 19130 |
| mlon_19258 | mlon | metabolomics | 1-myristoyl-2-palmitoyl-GPC (14:0/16:0) | 19258 |
| mlon_19260 | mlon | metabolomics | 1-oleoyl-GPS (18:1) | 19260 |
| mlon_19263 | mlon | metabolomics | 1-palmitoyl-2-oleoyl-GPE (16:0/18:1) | 19263 |
| mlon_19265 | mlon | metabolomics | 1-stearoyl-2-oleoyl-GPS (18:0/18:1) | 19265 |
| mlon_19266 | mlon | metabolomics | 2-arachidonoylglycerol (20:4) | 19266 |
| mlon_19324 | mlon | metabolomics | 1-stearoyl-GPI (18:0) | 19324 |
| mlon_19503 | mlon | metabolomics | stearoyl sphingomyelin (d18:1/18:0) | 19503 |
| mlon_20458 | mlon | metabolomics | 1-palmityl-GPC (O-16:0) | 20458 |
| mlon_20488 | mlon | metabolomics | glucose | 20488 |
| mlon_20675 | mlon | metabolomics | 1,5-anhydroglucitol (1,5-AG) | 20675 |
| mlon_20676 | mlon | metabolomics | maleate | 20676 |
| mlon_20693 | mlon | metabolomics | tartronate (hydroxymalonate) | 20693 |
| mlon_20694 | mlon | metabolomics | oxalate (ethanedioate) | 20694 |
| mlon_20699 | mlon | metabolomics | erythritol | 20699 |
| mlon_21025 | mlon | metabolomics | iminodiacetate (IDA) | 21025 |
| mlon_21049 | mlon | metabolomics | 1,6-anhydroglucose | 21049 |
| mlon_21127 | mlon | metabolomics | 1-palmitoylglycerol (16:0) | 21127 |
| mlon_21151 | mlon | metabolomics | saccharin | 21151 |
| mlon_21158 | mlon | metabolomics | 3-hydroxymyristate | 21158 |
| mlon_21184 | mlon | metabolomics | 1-oleoylglycerol (18:1) | 21184 |
| mlon_21232 | mlon | metabolomics | 2-oleoylglycerol (18:1) | 21232 |
| mlon_2125 | mlon | metabolomics | taurine | 2125 |
| mlon_2132 | mlon | metabolomics | citrulline | 2132 |
| mlon_2137 | mlon | metabolomics | biliverdin | 2137 |
| mlon_22001 | mlon | metabolomics | 3-hydroxyoctanoate | 22001 |
| mlon_22036 | mlon | metabolomics | 2-hydroxyoctanoate | 22036 |
| mlon_22053 | mlon | metabolomics | 3-hydroxydecanoate | 22053 |
| mlon_22116 | mlon | metabolomics | 4-methyl-2-oxopentanoate | 22116 |
| mlon_22130 | mlon | metabolomics | phenyllactate (PLA) | 22130 |
| mlon_22132 | mlon | metabolomics | alpha-hydroxyisocaproate | 22132 |
| mlon_22137 | mlon | metabolomics | homoarginine | 22137 |
| mlon_22138 | mlon | metabolomics | homocitrulline | 22138 |

TABLE 2-continued

| Probe name | platform | data_type | official_symbol | EGID/COMP_ID |
|---|---|---|---|---|
| mlon_22154 | mlon | metabolomics | bradykinin | 22154 |
| mlon_22163 | mlon | metabolomics | EDTA | 22163 |
| mlon_22176 | mlon | metabolomics | cysteine s-sulfate | 22176 |
| mlon_22185 | mlon | metabolomics | N-acetylaspartate (NAA) | 22185 |
| mlon_22194 | mlon | metabolomics | pyroglutamylglutamine | 22194 |
| mlon_22206 | mlon | metabolomics | theanine | 22206 |
| mlon_22290 | mlon | metabolomics | valproate (2-propylpentanoate) | 22290 |
| mlon_22842 | mlon | metabolomics | cholate | 22842 |
| mlon_2342 | mlon | metabolomics | serotonin | 2342 |
| mlon_2730 | mlon | metabolomics | gamma-glutamylglutamine | 2730 |
| mlon_2734 | mlon | metabolomics | gamma-glutamyltyrosine | 2734 |
| mlon_27414 | mlon | metabolomics | beta-sitosterol | 27414 |
| mlon_27447 | mlon | metabolomics | 1-linoleoylglycerol (18:2) | 27447 |
| mlon_27513 | mlon | metabolomics | indoleacetate | 27513 |
| mlon_2761 | mlon | metabolomics | thyroxine | 2761 |
| mlon_27665 | mlon | metabolomics | 1-methylnicotinamide | 27665 |
| mlon_27672 | mlon | metabolomics | 3-indoxyl sulfate | 27672 |
| mlon_27710 | mlon | metabolomics | N-acetylglycine | 27710 |
| mlon_27718 | mlon | metabolomics | creatine | 27718 |
| mlon_27719 | mlon | metabolomics | galactonate | 27719 |
| mlon_2772 | mlon | metabolomics | topiramate | 2772 |
| mlon_27731 | mlon | metabolomics | ribonate (ribonolactone) | 27731 |
| mlon_27738 | mlon | metabolomics | threonate | 27738 |
| mlon_2829 | mlon | metabolomics | N-formylmethionine | 2829 |
| mlon_30460 | mlon | metabolomics | 1-methylhistidine | 30460 |
| mlon_3127 | mlon | metabolomics | hypoxanthine | 3127 |
| mlon_3141 | mlon | metabolomics | betaine | 3141 |
| mlon_3147 | mlon | metabolomics | xanthine | 3147 |
| mlon_31536 | mlon | metabolomics | N-(2-furoyl)glycine | 31536 |
| mlon_31548 | mlon | metabolomics | DSGEGDFXAEGGGVR* | 31548 |
| mlon_3155 | mlon | metabolomics | 3-ureidopropionate | 3155 |
| mlon_31555 | mlon | metabolomics | pyridoxate | 31555 |
| mlon_31591 | mlon | metabolomics | androsterone sulfate | 31591 |
| mlon_31787 | mlon | metabolomics | 3-carboxy-4-methyl-5-propyl-2-furanpropanoate (CMPF) | 31787 |
| mlon_31904 | mlon | metabolomics | 7-ketodeoxycholate | 31904 |
| mlon_31912 | mlon | metabolomics | glycolithocholate | 31912 |
| mlon_31932 | mlon | metabolomics | propionylglycine (C3) | 31932 |
| mlon_31934 | mlon | metabolomics | 2-hydroxyadipate | 31934 |
| mlon_31938 | mlon | metabolomics | 5-hydroxyhexanoate | 31938 |
| mlon_31943 | mlon | metabolomics | 3-hydroxysebacate | 31943 |
| mlon_32197 | mlon | metabolomics | 3-(4-hydroxyphenyl)lactate (HPLA) | 32197 |
| mlon_32198 | mlon | metabolomics | acetylcarnitine (C2) | 32198 |
| mlon_32306 | mlon | metabolomics | hydroxyproline | 32306 |
| mlon_32328 | mlon | metabolomics | hexanoylcarnitine (C6) | 32328 |
| mlon_32342 | mlon | metabolomics | AMP | 32342 |
| mlon_32346 | mlon | metabolomics | glycochenodeoxycholate | 32346 |
| mlon_32350 | mlon | metabolomics | 1-methyl-4-imidazoleacetate | 32350 |
| mlon_32377 | mlon | metabolomics | N-acetylneuraminate | 32377 |
| mlon_32388 | mlon | metabolomics | dodecanedioate (C12) | 32388 |
| mlon_32390 | mlon | metabolomics | N-acetyltyrosine | 32390 |
| mlon_32391 | mlon | metabolomics | 1,3-dimethylurate | 32391 |
| mlon_32394 | mlon | metabolomics | pyroglutamylvaline | 32394 |
| mlon_32397 | mlon | metabolomics | 3-hydroxy-2-ethylpropionate | 32397 |
| mlon_32398 | mlon | metabolomics | sebacate (C10-DC) | 32398 |
| mlon_32401 | mlon | metabolomics | trigonelline (N'-methylnicotinate) | 32401 |
| mlon_32405 | mlon | metabolomics | indolepropionate | 32405 |
| mlon_32412 | mlon | metabolomics | butyrylcarnitine (C4) | 32412 |
| mlon_32415 | mlon | metabolomics | docosadienoate (22:2n6) | 32415 |
| mlon_32417 | mlon | metabolomics | docosatrienoate (22:3n3) | 32417 |
| mlon_32418 | mlon | metabolomics | myristoleate (14:1n5) | 32418 |
| mlon_32425 | mlon | metabolomics | dehydroisoandrosterone sulfate (DHEA-S) | 32425 |
| mlon_32426 | mlon | metabolomics | I-urobilinogen | 32426 |
| mlon_32445 | mlon | metabolomics | 3-methylxanthine | 32445 |
| mlon_32452 | mlon | metabolomics | propionylcarnitine (C3) | 32452 |
| mlon_32455 | mlon | metabolomics | linoleamide (18:2n6) | 32455 |
| mlon_32457 | mlon | metabolomics | 3-hydroxylaurate | 32457 |
| mlon_32458 | mlon | metabolomics | oleamide | 32458 |
| mlon_32462 | mlon | metabolomics | N-linoleoylglycine | 32462 |
| mlon_32463 | mlon | metabolomics | arachidonoyl ethanolamide | 32463 |
| mlon_32489 | mlon | metabolomics | caproate (6:0) | 32489 |
| mlon_32492 | mlon | metabolomics | caprylate (8:0) | 32492 |
| mlon_32497 | mlon | metabolomics | 10-undecenoate (11:1n1) | 32497 |
| mlon_32504 | mlon | metabolomics | docosapentaenoate (DPA; 22:5n3) | 32504 |
| mlon_32506 | mlon | metabolomics | 2-linoleoylglycerol (18:2) | 32506 |
| mlon_32553 | mlon | metabolomics | phenol sulfate | 32553 |
| mlon_32562 | mlon | metabolomics | pregnen-diol disulfate* | 32562 |
| mlon_32586 | mlon | metabolomics | bilirubin (E,E)* | 32586 |

TABLE 2-continued

| Probe name | platform | data_type | official_symbol | EGID/COMP_ID |
|---|---|---|---|---|
| mlon_32599 | mlon | metabolomics | glycocholenate sulfate* | 32599 |
| mlon_32619 | mlon | metabolomics | pregnenediol sulfate (C21H34O5S)* | 32619 |
| mlon_32620 | mlon | metabolomics | glycolithocholate sulfate* | 32620 |
| mlon_32807 | mlon | metabolomics | taurocholenate sulfate* | 32807 |
| mlon_32815 | mlon | metabolomics | 2-arachidonoyl-GPE* (20:4)* | 32815 |
| mlon_32827 | mlon | metabolomics | andro steroid monosulfate C19H28O6S (1)* | 32827 |
| mlon_32836 | mlon | metabolomics | HWESASXX* | 32836 |
| mlon_32882 | mlon | metabolomics | hydroxybupropion | 32882 |
| mlon_32980 | mlon | metabolomics | adrenate (22:4n6) | 32980 |
| mlon_33009 | mlon | metabolomics | homostachydrine* | 33009 |
| mlon_33161 | mlon | metabolomics | 2-methoxyacetaminophen glucuronide* | 33161 |
| mlon_33173 | mlon | metabolomics | 2-hydroxyacetaminophen sulfate* | 33173 |
| mlon_33228 | mlon | metabolomics | 1-arachidonoyl-GPC* (20:4)* | 33228 |
| mlon_33230 | mlon | metabolomics | 1-palmitoleoyl-GPC* (16:1)* | 33230 |
| mlon_33364 | mlon | metabolomics | gamma-glutamylthreonine | 33364 |
| mlon_33384 | mlon | metabolomics | salicyluric glucuronide* | 33384 |
| mlon_33387 | mlon | metabolomics | 2-arachidonoyl-GPC* (20:4)* | 33387 |
| mlon_33419 | mlon | metabolomics | 2-palmitoylglycerol (16:0) | 33419 |
| mlon_33422 | mlon | metabolomics | gamma-glutamylphenylalanine | 33422 |
| mlon_33441 | mlon | metabolomics | isobutyrylcarnitine (C4) | 33441 |
| mlon_33442 | mlon | metabolomics | pseudouridine | 33442 |
| mlon_33447 | mlon | metabolomics | palmitoleate (16:1n7) | 33447 |
| mlon_33587 | mlon | metabolomics | eicosenoate (20:1n9 or 1n11) | 33587 |
| mlon_33821 | mlon | metabolomics | 1-eicosatrienoyl-GPC* (20:3)* | 33821 |
| mlon_33822 | mlon | metabolomics | 1-docosahexaenoyl-GPC* (22:6)* | 33822 |
| mlon_33871 | mlon | metabolomics | 1-eicosadienoyl-GPC* (20:2)* | 33871 |
| mlon_33934 | mlon | metabolomics | gamma-glutamyl-epsilon-lysine | 33934 |
| mlon_33935 | mlon | metabolomics | piperine | 33935 |
| mlon_33936 | mlon | metabolomics | octanoylcarnitine (C8) | 33936 |
| mlon_33937 | mlon | metabolomics | alpha-hydroxyisovalerate | 33937 |
| mlon_33939 | mlon | metabolomics | N-acetylthreonine | 33939 |
| mlon_33941 | mlon | metabolomics | decanoylcarnitine (C10) | 33941 |
| mlon_33943 | mlon | metabolomics | N-acetylglutamine | 33943 |
| mlon_33946 | mlon | metabolomics | N-acetylhistidine | 33946 |
| mlon_33947 | mlon | metabolomics | gamma-glutamyltryptophan | 33947 |
| mlon_33949 | mlon | metabolomics | gamma-glutamylglycine | 33949 |
| mlon_33950 | mlon | metabolomics | N-acetylphenylalanine | 33950 |
| mlon_33952 | mlon | metabolomics | myristoylcarnitine (C14) | 33952 |
| mlon_33953 | mlon | metabolomics | N-acetylarginine | 33953 |
| mlon_33955 | mlon | metabolomics | 1-palmitoyl-GPC (16:0) | 33955 |
| mlon_33959 | mlon | metabolomics | N-acetyltryptophan | 33959 |
| mlon_33961 | mlon | metabolomics | 1-stearoyl-GPC (18:0) | 33961 |
| mlon_33962 | mlon | metabolomics | (Hyp-3)-Bradykinin | 33962 |
| mlon_33967 | mlon | metabolomics | N-acetylisoleucine | 33967 |
| mlon_33968 | mlon | metabolomics | 5-dodecenoate (12:1n7) | 33968 |
| mlon_33969 | mlon | metabolomics | stearidonate (18:4n3) | 33969 |
| mlon_33971 | mlon | metabolomics | 10-heptadecenoate (17:1n7) | 33971 |
| mlon_33972 | mlon | metabolomics | 10-nonadecenoate (19:1n9) | 33972 |
| mlon_33973 | mlon | metabolomics | epiandrosterone sulfate | 33973 |
| mlon_33983 | mlon | metabolomics | tauro-beta-muricholate | 33983 |
| mlon_33997 | mlon | metabolomics | campesterol | 33997 |
| mlon_34035 | mlon | metabolomics | linolenate (18:3n3 or 3n6) | 34035 |
| mlon_34093 | mlon | metabolomics | hyocholate | 34093 |
| mlon_34109 | mlon | metabolomics | metoprolol acid metabolite* | 34109 |
| mlon_34214 | mlon | metabolomics | 1-arachidonoyl-GPI* (20:4)* | 34214 |
| mlon_34258 | mlon | metabolomics | 2-docosahexaenoyl-GPE (22:6)* | 34258 |
| mlon_34365 | mlon | metabolomics | 3-(cystein-S-yl)acetaminophen* | 34365 |
| mlon_34384 | mlon | metabolomics | stachydrine | 34384 |
| mlon_34387 | mlon | metabolomics | N-acetylproline | 34387 |
| mlon_34389 | mlon | metabolomics | 1-methylxanthine | 34389 |
| mlon_34390 | mlon | metabolomics | 7-methylxanthine | 34390 |
| mlon_34393 | mlon | metabolomics | 1-linolenoylglycerol (18:3) | 34393 |
| mlon_34395 | mlon | metabolomics | 1-methylurate | 34395 |
| mlon_34396 | mlon | metabolomics | phosphocholine | 34396 |
| mlon_34397 | mlon | metabolomics | 1-arachidonylglycerol (20:4) | 34397 |
| mlon_34399 | mlon | metabolomics | 3,7-dimethylurate | 34399 |
| mlon_34400 | mlon | metabolomics | 1,7-dimethylurate | 34400 |
| mlon_34401 | mlon | metabolomics | 5-acetylamino-6-formylamino-3-methyluracil | 34401 |
| mlon_34404 | mlon | metabolomics | 1,3,7-trimethylurate | 34404 |
| mlon_34407 | mlon | metabolomics | isovalerylcarnitine (C5) | 34407 |
| mlon_34409 | mlon | metabolomics | stearoylcarnitine (C18) | 34409 |
| mlon_34419 | mlon | metabolomics | 1-linoleoyl-GPC (18:2) | 34419 |
| mlon_34420 | mlon | metabolomics | bradykinin, des-arg(9) | 34420 |
| mlon_34424 | mlon | metabolomics | 5-acetylamino-6-amino-3-methyluracil | 34424 |
| mlon_34437 | mlon | metabolomics | 1-stearoyl-GPG (18:0) | 34437 |
| mlon_34445 | mlon | metabolomics | sphingosine 1-phosphate | 34445 |
| mlon_34456 | mlon | metabolomics | gamma-glutamylisoleucine* | 34456 |
| mlon_34534 | mlon | metabolomics | laurylcarnitine (C12) | 34534 |

TABLE 2-continued

| Probe name | platform | data_type | official_symbol | EGID/COMP_ID |
|---|---|---|---|---|
| mlon_34565 | mlon | metabolomics | 1-palmitoleoyl-GPE (16:1)* | 34565 |
| mlon_35107 | mlon | metabolomics | isovalerylglycine | 35107 |
| mlon_35114 | mlon | metabolomics | 7-methylguanine | 35114 |
| mlon_35126 | mlon | metabolomics | phenylacetylglutamine | 35126 |
| mlon_35127 | mlon | metabolomics | prolylhydroxyproline | 35127 |
| mlon_35130 | mlon | metabolomics | N4-acetylcytidine | 35130 |
| mlon_35136 | mlon | metabolomics | 5-methyluridine (ribothymidine) | 35136 |
| mlon_35137 | mlon | metabolomics | N2,N2-dimethylguanosine | 35137 |
| mlon_35153 | mlon | metabolomics | 1-docosahexaenoylglycerol (22:6) | 35153 |
| mlon_35157 | mlon | metabolomics | N6-carbamoylthreonyladenosine | 35157 |
| mlon_35159 | mlon | metabolomics | cysteine-glutathione disulfide | 35159 |
| mlon_35160 | mlon | metabolomics | oleoylcarnitine (C18) | 35160 |
| mlon_35172 | mlon | metabolomics | orotidine | 35172 |
| mlon_35186 | mlon | metabolomics | 1-arachidonoyl-GPE (20:4n6)* | 35186 |
| mlon_35253 | mlon | metabolomics | 2-palmitoyl-GPC* (16:0)* | 35253 |
| mlon_35257 | mlon | metabolomics | 2-linoleoyl-GPC* (18:2)* | 35257 |
| mlon_35305 | mlon | metabolomics | 1-palmitoyl-GPI* (16:0) | 35305 |
| mlon_35320 | mlon | metabolomics | catechol sulfate | 35320 |
| mlon_35322 | mlon | metabolomics | hydroquinone sulfate | 35322 |
| mlon_35428 | mlon | metabolomics | tiglyl carnitine (C5) | 35428 |
| mlon_35436 | mlon | metabolomics | hexanoylglycine (C6) | 35436 |
| mlon_35437 | mlon | metabolomics | isobutyrylglycine (C4) | 35437 |
| mlon_35527 | mlon | metabolomics | 4-hydroxyhippurate | 35527 |
| mlon_35625 | mlon | metabolomics | 1-myristoylglycerol (14:0) | 35625 |
| mlon_35626 | mlon | metabolomics | 2-myristoyl-GPC* (14:0)* | 35626 |
| mlon_35628 | mlon | metabolomics | 1-oleoyl-GPE (18:1) | 35628 |
| mlon_35631 | mlon | metabolomics | 1-palmitoyl-GPE (16:0) | 35631 |
| mlon_35635 | mlon | metabolomics | 3-(3-hydroxyphenyl)propionate | 35635 |
| mlon_35637 | mlon | metabolomics | cysteinylglycine | 35637 |
| mlon_35651 | mlon | metabolomics | ectoine | 35651 |
| mlon_35665 | mlon | metabolomics | N-acetyl-aspartyl-glutamate (NAAG) | 35665 |
| mlon_35669 | mlon | metabolomics | tetradecanedioate (C14) | 35669 |
| mlon_35675 | mlon | metabolomics | 2-hydroxypalmitate | 35675 |
| mlon_35678 | mlon | metabolomics | hexadecanedioate (C16) | 35678 |
| mlon_35718 | mlon | metabolomics | dihomolinolenate (20:3n3 or 3n6) | 35718 |
| mlon_36095 | mlon | metabolomics | thymol sulfate | 36095 |
| mlon_36098 | mlon | metabolomics | 4-vinylphenol sulfate | 36098 |
| mlon_36099 | mlon | metabolomics | 4-ethylphenyl sulfate | 36099 |
| mlon_36103 | mlon | metabolomics | p-cresol sulfate | 36103 |
| mlon_36593 | mlon | metabolomics | 2-linoleoyl-GPE* (18:2)* | 36593 |
| mlon_36594 | mlon | metabolomics | 1-linoleoyl-GPI* (18:2)* | 36594 |
| mlon_36600 | mlon | metabolomics | 1-linoleoyl-GPE (18:2)* | 36600 |
| mlon_36602 | mlon | metabolomics | 1-oleoyl-GPI (18:1)* | 36602 |
| mlon_36618 | mlon | metabolomics | 1-palmitoleoyl-GPI* (16:1)* | 36618 |
| mlon_36649 | mlon | metabolomics | sucralose | 36649 |
| mlon_36713 | mlon | metabolomics | N6-carboxymethyllysine | 36713 |
| mlon_36738 | mlon | metabolomics | gamma-glutamylglutamate | 36738 |
| mlon_36746 | mlon | metabolomics | 2-hydroxy-3-methylvalerate | 36746 |
| mlon_36747 | mlon | metabolomics | deoxycarnitine | 36747 |
| mlon_36751 | mlon | metabolomics | N2-acetyllysine | 36751 |
| mlon_36752 | mlon | metabolomics | N6-acetyllysine | 36752 |
| mlon_36754 | mlon | metabolomics | octadecanedioate (C18) | 36754 |
| mlon_36776 | mlon | metabolomics | 7-HOCA | 36776 |
| mlon_36808 | mlon | metabolomics | dimethylarginine (ADMA + SDMA) | 36808 |
| mlon_36845 | mlon | metabolomics | o-cresol sulfate | 36845 |
| mlon_36850 | mlon | metabolomics | taurolithocholate 3-sulfate | 36850 |
| mlon_37020 | mlon | metabolomics | carbamazepine 10,11-epoxide* | 37020 |
| mlon_37033 | mlon | metabolomics | carbamazepine | 37033 |
| mlon_37058 | mlon | metabolomics | succinylcarnitine (C4) | 37058 |
| mlon_37059 | mlon | metabolomics | malonylcarnitine | 37059 |
| mlon_37063 | mlon | metabolomics | gamma-glutamylalanine | 37063 |
| mlon_37073 | mlon | metabolomics | alpha-hydroxycaproate | 37073 |
| mlon_37076 | mlon | metabolomics | N-acetylserine | 37076 |
| mlon_37097 | mlon | metabolomics | tryptophan betaine | 37097 |
| mlon_37112 | mlon | metabolomics | chiro-inositol | 37112 |
| mlon_37174 | mlon | metabolomics | 21-hydroxypregnenolone monosulfate (1) | 37174 |
| mlon_37181 | mlon | metabolomics | 4-allylphenol sulfate | 37181 |
| mlon_37183 | mlon | metabolomics | 5alpha-androstan-3alpha,17alpha-diol monosulfate | 37183 |
| mlon_37184 | mlon | metabolomics | 5alpha-androstan-3alpha,17beta-diol disulfate | 37184 |
| mlon_37185 | mlon | metabolomics | 5alpha-androstan-3alpha,17beta-diol monosulfate (2) | 37185 |
| mlon_37186 | mlon | metabolomics | 5alpha-androstan-3alpha,17beta-diol monosulfate (1) | 37186 |
| mlon_37187 | mlon | metabolomics | 5alpha-androstan-3beta,17alpha-diol disulfate | 37187 |
| mlon_37190 | mlon | metabolomics | 5alpha-androstan-3beta,17beta-diol disulfate | 37190 |
| mlon_37192 | mlon | metabolomics | 5alpha-androstan-3beta,17beta-diol monosulfate (2) | 37192 |
| mlon_37196 | mlon | metabolomics | 5alpha-pregnan-3beta,20beta-diol monosulfate (1) | 37196 |
| mlon_37198 | mlon | metabolomics | 5alpha-pregnan-3beta,20alpha-diol disulfate | 37198 |
| mlon_37200 | mlon | metabolomics | 5alpha-pregnan-3beta,20alpha-diol monosulfate (2) | 37200 |
| mlon_37202 | mlon | metabolomics | androstenediol (3beta,17beta) disulfate (1) | 37202 |

TABLE 2-continued

| Probe name | platform | data_type | official_symbol | EGID/COMP_ID |
|---|---|---|---|---|
| mlon_37203 | mlon | metabolomics | androstenediol (3beta,17beta) disulfate (2) | 37203 |
| mlon_37207 | mlon | metabolomics | androstenediol (3alpha,17alpha) monosulfate (2) | 37207 |
| mlon_37209 | mlon | metabolomics | androstenediol (3alpha,17alpha) monosulfate (3) | 37209 |
| mlon_37210 | mlon | metabolomics | androstenediol (3beta,17beta) monosulfate (2) | 37210 |
| mlon_37211 | mlon | metabolomics | androstenediol (3beta,17beta) monosulfate (1) | 37211 |
| mlon_37231 | mlon | metabolomics | 1-docosapentaenoyl-GPC* (22:5n3)* | 37231 |
| mlon_37418 | mlon | metabolomics | 1-pentadecanoyl-GPC (15:0)* | 37418 |
| mlon_37419 | mlon | metabolomics | 1-margaroyl-GPE (17:0)* | 37419 |
| mlon_37431 | mlon | metabolomics | N-methylproline | 37431 |
| mlon_37432 | mlon | metabolomics | N-acetyl-beta-alanine | 37432 |
| mlon_37443 | mlon | metabolomics | cysteine sulfinic acid | 37443 |
| mlon_37445 | mlon | metabolomics | 4-hydroxycoumarin | 37445 |
| mlon_37455 | mlon | metabolomics | glycerophoethanolamine | 37455 |
| mlon_37459 | mlon | metabolomics | ergothioneine | 37459 |
| mlon_37475 | mlon | metabolomics | 4-acetaminophen sulfate | 37475 |
| mlon_37478 | mlon | metabolomics | docosapentaenoate (n6 DPA; 22:5n6) | 37478 |
| mlon_37480 | mlon | metabolomics | 5alpha-pregnan-3beta-ol,20-one sulfate | 37480 |
| mlon_37482 | mlon | metabolomics | 17alpha-hydroxypregnenolone 3-sulfate | 37482 |
| mlon_37496 | mlon | metabolomics | N-acetylputrescine | 37496 |
| mlon_37506 | mlon | metabolomics | palmitoyl sphingomyelin (d18:1/16:0) | 37506 |
| mlon_37529 | mlon | metabolomics | sphingomyelin (d18:1/18:1, d18:2/18:0) | 37529 |
| mlon_37536 | mlon | metabolomics | 12-HETE | 37536 |
| mlon_37538 | mlon | metabolomics | 15-HETE | 37538 |
| mlon_37752 | mlon | metabolomics | 13-HODE + 9-HODE | 37752 |
| mlon_38102 | mlon | metabolomics | oleoyl ethanolamide | 38102 |
| mlon_38116 | mlon | metabolomics | indole-3-carboxylate | 38116 |
| mlon_38125 | mlon | metabolomics | 4-cholesten-3-one | 38125 |
| mlon_38127 | mlon | metabolomics | S-methylmethionine | 38127 |
| mlon_38165 | mlon | metabolomics | palmitoyl ethanolamide | 38165 |
| mlon_38168 | mlon | metabolomics | 16a-hydroxy DHEA 3-sulfate | 38168 |
| mlon_38170 | mlon | metabolomics | pregnenolone sulfate | 38170 |
| mlon_38178 | mlon | metabolomics | cis-4-decenoylcarnitine (C10:1) | 38178 |
| mlon_38276 | mlon | metabolomics | 2,3-dihydroxyisovalerate | 38276 |
| mlon_38293 | mlon | metabolomics | (12 or 13)-methylmyristate (a15:0 or i15:0) | 38293 |
| mlon_38296 | mlon | metabolomics | (16 or 17)-methylstearate (a19:0 or i19:0) | 38296 |
| mlon_38306 | mlon | metabolomics | metformin | 38306 |
| mlon_38309 | mlon | metabolomics | 4-hydroxynonenal | 38309 |
| mlon_38321 | mlon | metabolomics | allopurinol riboside | 38321 |
| mlon_38366 | mlon | metabolomics | ibuprofen acyl glucuronide | 38366 |
| mlon_38395 | mlon | metabolomics | 12,13-DiHOME | 38395 |
| mlon_38399 | mlon | metabolomics | 9,10-DiHOME | 38399 |
| mlon_38595 | mlon | metabolomics | ranitidine | 38595 |
| mlon_38599 | mlon | metabolomics | celecoxib | 38599 |
| mlon_38600 | mlon | metabolomics | omeprazole | 38600 |
| mlon_38609 | mlon | metabolomics | pantoprazole | 38609 |
| mlon_38623 | mlon | metabolomics | venlafaxine | 38623 |
| mlon_38637 | mlon | metabolomics | cinnamoylglycine | 38637 |
| mlon_38658 | mlon | metabolomics | atenolol | 38658 |
| mlon_38661 | mlon | metabolomics | hydroxycotinine | 38661 |
| mlon_38662 | mlon | metabolomics | cotinine N-oxide | 38662 |
| mlon_38667 | mlon | metabolomics | 3-methylglutaconate | 38667 |
| mlon_38669 | mlon | metabolomics | diphenhydramine | 38669 |
| mlon_38686 | mlon | metabolomics | gabapentin | 38686 |
| mlon_38768 | mlon | metabolomics | (14 or 15)-methylpalmitate (a17:0 or i17:0) | 38768 |
| mlon_39221 | mlon | metabolomics | 2-linoleoyl-GPI (18:2)* | 39221 |
| mlon_39223 | mlon | metabolomics | 2-stearoyl-GPI (18:0)* | 39223 |
| mlon_39270 | mlon | metabolomics | 1-(1-enyl-palmitoyl)-GPE (P-16:0)* | 39270 |
| mlon_39271 | mlon | metabolomics | 1-(1-enyl-stearoyl)-GPE (P-18:0)* | 39271 |
| mlon_39273 | mlon | metabolomics | doxycycline | 39273 |
| mlon_39346 | mlon | metabolomics | alpha-CEHC glucuronide* | 39346 |
| mlon_39378 | mlon | metabolomics | tauroursodeoxycholate | 39378 |
| mlon_39379 | mlon | metabolomics | glycoursodeoxycholate | 39379 |
| mlon_39586 | mlon | metabolomics | pseudoephedrine | 39586 |
| mlon_39592 | mlon | metabolomics | S-methylcysteine | 39592 |
| mlon_39598 | mlon | metabolomics | 7-methylurate | 39598 |
| mlon_396 | mlon | metabolomics | glutarate (C5-DC) | 396 |
| mlon_39600 | mlon | metabolomics | 3-hydroxyhippurate | 39600 |
| mlon_39603 | mlon | metabolomics | ethyl glucuronide | 39603 |
| mlon_39609 | mlon | metabolomics | 16-hydroxypalmitate | 39609 |
| mlon_39625 | mlon | metabolomics | hydrochlorothiazide | 39625 |
| mlon_39730 | mlon | metabolomics | N-stearoyltaurine | 39730 |
| mlon_39732 | mlon | metabolomics | N-oleoyltaurine | 39732 |
| mlon_39757 | mlon | metabolomics | sertraline | 39757 |
| mlon_39767 | mlon | metabolomics | quinine | 39767 |
| mlon_39787 | mlon | metabolomics | quetiapine | 39787 |
| mlon_39788 | mlon | metabolomics | solanidine | 39788 |
| mlon_39792 | mlon | metabolomics | 1-behenoyl-GPC (22:0) | 39792 |
| mlon_39831 | mlon | metabolomics | eicosanodioate (C20-DC) | 39831 |

TABLE 2-continued

| Probe name | platform | data_type | official_symbol | EGID/COMP_ID |
|---|---|---|---|---|
| mlon_39835 | mlon | metabolomics | N-palmitoyltaurine | 39835 |
| mlon_39837 | mlon | metabolomics | docosadioate (C22-DC) | 39837 |
| mlon_39994 | mlon | metabolomics | valylleucine | 39994 |
| mlon_40007 | mlon | metabolomics | carboxyethyl-GABA | 40007 |
| mlon_40062 | mlon | metabolomics | 4-hydroxy-2-oxoglutaric acid | 40062 |
| mlon_40173 | mlon | metabolomics | L-urobilin | 40173 |
| mlon_40406 | mlon | metabolomics | trimethylamine N-oxide | 40406 |
| mlon_40450 | mlon | metabolomics | duloxetine | 40450 |
| mlon_40456 | mlon | metabolomics | fluvoxamine | 40456 |
| mlon_40459 | mlon | metabolomics | escitalopram | 40459 |
| mlon_40461 | mlon | metabolomics | paroxetine | 40461 |
| mlon_40469 | mlon | metabolomics | N1-Methyl-2-pyridone-5-carboxamide | 40469 |
| mlon_40473 | mlon | metabolomics | hydantoin-5-propionate | 40473 |
| mlon_40481 | mlon | metabolomics | dihydroferulic acid | 40481 |
| mlon_40499 | mlon | metabolomics | 4-hydroxyglutamate | 40499 |
| mlon_40685 | mlon | metabolomics | methionylalanine | 40685 |
| mlon_40703 | mlon | metabolomics | prolylglycine | 40703 |
| mlon_40708 | mlon | metabolomics | pregnanediol-3-glucuronide | 40708 |
| mlon_40730 | mlon | metabolomics | imidazole propionate | 40730 |
| mlon_41220 | mlon | metabolomics | 2-stearoyl-GPE (18:0)* | 41220 |
| mlon_41377 | mlon | metabolomics | phenylalanyltryptophan | 41377 |
| mlon_41494 | mlon | metabolomics | alliin | 41494 |
| mlon_41754 | mlon | metabolomics | heme | 41754 |
| mlon_41888 | mlon | metabolomics | succinimide | 41888 |
| mlon_42002 | mlon | metabolomics | lanthionine | 42002 |
| mlon_42021 | mlon | metabolomics | fexofenadine | 42021 |
| mlon_42027 | mlon | metabolomics | histidylalanine | 42027 |
| mlon_42077 | mlon | metabolomics | seryltyrosine | 42077 |
| mlon_42087 | mlon | metabolomics | indoleacetylglutamine | 42087 |
| mlon_42092 | mlon | metabolomics | N-palmitoylglycine | 42092 |
| mlon_42095 | mlon | metabolomics | palmitamide (16:0) | 42095 |
| mlon_42109 | mlon | metabolomics | phosphate | 42109 |
| mlon_42370 | mlon | metabolomics | S-1-pyrroline-5-carboxylate | 42370 |
| mlon_42374 | mlon | metabolomics | 2-aminobutyrate | 42374 |
| mlon_42381 | mlon | metabolomics | gamma-CEHC glucuronide* | 42381 |
| mlon_42382 | mlon | metabolomics | S-adenosylhomocysteine (SAH) | 42382 |
| mlon_42398 | mlon | metabolomics | 1-stearoyl-GPE (18:0) | 42398 |
| mlon_42420 | mlon | metabolomics | erythronate* | 42420 |
| mlon_42446 | mlon | metabolomics | 1-palmitoyl-2-linoleoyl-GPC (16:0/18:2) | 42446 |
| mlon_42448 | mlon | metabolomics | 1-stearoyl-2-oleoyl-GPE (18:0/18:1) | 42448 |
| mlon_42449 | mlon | metabolomics | 1-palmitoyl-2-linoleoyl-GPE (16:0/18:2) | 42449 |
| mlon_42450 | mlon | metabolomics | 1-stearoyl-2-arachidonoyl-GPC (18:0/20:4) | 42450 |
| mlon_42459 | mlon | metabolomics | sphingomyelin (d18:2/16:0, d18:1/16:1)* | 42459 |
| mlon_42463 | mlon | metabolomics | sphingomyelin (d18:1/14:0, d16:1/16:0)* | 42463 |
| mlon_42489 | mlon | metabolomics | 2-hydroxydecanoate | 42489 |
| mlon_42574 | mlon | metabolomics | glycohyocholate | 42574 |
| mlon_42613 | mlon | metabolomics | famotidine | 42613 |
| mlon_42989 | mlon | metabolomics | N-methyltaurine | 42989 |
| mlon_43231 | mlon | metabolomics | 6-oxopiperidine-2-carboxylate | 43231 |
| mlon_43239 | mlon | metabolomics | S-allylcysteine | 43239 |
| mlon_43249 | mlon | metabolomics | N-delta-acetylornithine | 43249 |
| mlon_43255 | mlon | metabolomics | N-acetyl-1-methylhistidine* | 43255 |
| mlon_43256 | mlon | metabolomics | N-acetyl-3-methylhistidine* | 43256 |
| mlon_43258 | mlon | metabolomics | acisoga | 43258 |
| mlon_43264 | mlon | metabolomics | 3-hydroxybutyrylcarnitine (1) | 43264 |
| mlon_43265 | mlon | metabolomics | benzoylcarnitine* | 43265 |
| mlon_43266 | mlon | metabolomics | 2-aminophenol sulfate | 43266 |
| mlon_43330 | mlon | metabolomics | 2-hydroxyibuprofen | 43330 |
| mlon_43333 | mlon | metabolomics | carboxyibuprofen | 43333 |
| mlon_43334 | mlon | metabolomics | O-desmethylvenlafaxine | 43334 |
| mlon_43335 | mlon | metabolomics | warfarin | 43335 |
| mlon_43343 | mlon | metabolomics | 2-aminooctanoate | 43343 |
| mlon_43374 | mlon | metabolomics | indolin-2-one | 43374 |
| mlon_43378 | mlon | metabolomics | S-methylcysteine sulfoxide | 43378 |
| mlon_43400 | mlon | metabolomics | 2-piperidinone | 43400 |
| mlon_43424 | mlon | metabolomics | dimethyl sulfone | 43424 |
| mlon_43488 | mlon | metabolomics | N-acetylcarnosine | 43488 |
| mlon_43493 | mlon | metabolomics | formiminoglutamate | 43493 |
| mlon_43496 | mlon | metabolomics | 3-hydroxyquinine | 43496 |
| mlon_43507 | mlon | metabolomics | 3b-hydroxy-5-cholenoic acid | 43507 |
| mlon_43530 | mlon | metabolomics | N-acetyl-cadaverine | 43530 |
| mlon_43534 | mlon | metabolomics | allopurinol | 43534 |
| mlon_43582 | mlon | metabolomics | 5-(galactosylhydroxy)-L-lysine | 43582 |
| mlon_43591 | mlon | metabolomics | N2,N5-diacetylornithine | 43591 |
| mlon_43592 | mlon | metabolomics | 4-methylbenzenesulfonate | 43592 |
| mlon_43761 | mlon | metabolomics | 2-aminoheptanoate | 43761 |
| mlon_43802 | mlon | metabolomics | guanidinoacetate | 43802 |
| mlon_43807 | mlon | metabolomics | bilirubin | 43807 |

TABLE 2-continued

| Probe name | platform | data_type | official_symbol | EGID/COMP_ID |
|---|---|---|---|---|
| mlon_43829 | mlon | metabolomics | gamma-glutamylvaline | 43829 |
| mlon_43847 | mlon | metabolomics | glycerol 3-phosphate | 43847 |
| mlon_443 | mlon | metabolomics | aspartate | 443 |
| mlon_44526 | mlon | metabolomics | 3-methyl-2-oxobutyrate | 44526 |
| mlon_44560 | mlon | metabolomics | 1-eicosenoyl-GPC (20:1)* | 44560 |
| mlon_44563 | mlon | metabolomics | 1-eicosapentaenoyl-GPC (20:5)* | 44563 |
| mlon_44618 | mlon | metabolomics | 3-methoxytyramine sulfate | 44618 |
| mlon_44620 | mlon | metabolomics | 4-acetylphenyl sulfate | 44620 |
| mlon_44621 | mlon | metabolomics | 1-(1-enyl-oleoyl)-GPE (P-18:1)* | 44621 |
| mlon_44630 | mlon | metabolomics | 1-dihomo-linolenoyl-GPE (20:3n3 or 6)* | 44630 |
| mlon_44633 | mlon | metabolomics | 1-docosahexaenoyl-GPE (22:6)* | 44633 |
| mlon_44656 | mlon | metabolomics | isovalerate (C5) | 44656 |
| mlon_44657 | mlon | metabolomics | HWESASLLR | 44657 |
| mlon_44664 | mlon | metabolomics | glutaroylcarnitine (C5) | 44664 |
| mlon_44675 | mlon | metabolomics | docosahexaenoate (DHA; 22:6n3) | 44675 |
| mlon_44681 | mlon | metabolomics | palmitoylcarnitine (C16) | 44681 |
| mlon_44682 | mlon | metabolomics | 1-heptadecanoyl-GPC (17:0) | 44682 |
| mlon_44683 | mlon | metabolomics | 2-margaroyl-GPC (17:0)* | 44683 |
| mlon_44688 | mlon | metabolomics | maltotriose | 44688 |
| mlon_44872 | mlon | metabolomics | gamma-glutamylmethionine | 44872 |
| mlon_44876 | mlon | metabolomics | gamma-CEHC | 44876 |
| mlon_44877 | mlon | metabolomics | N-palmitoyl-sphingosine (d18:1/16:0) | 44877 |
| mlon_44878 | mlon | metabolomics | methionine sulfone | 44878 |
| mlon_45095 | mlon | metabolomics | 2-methylbutyroylcarnitine (C5) | 45095 |
| mlon_45404 | mlon | metabolomics | N-acetylalliin | 45404 |
| mlon_45413 | mlon | metabolomics | O-sulfo-L-tyrosine | 45413 |
| mlon_45415 | mlon | metabolomics | 3-(3-hydroxyphenyl)propionate sulfate | 45415 |
| mlon_45452 | mlon | metabolomics | 2-palmitoyl-GPE* (16:0)* | 45452 |
| mlon_45453 | mlon | metabolomics | 1-myristoyl-GPC (14:0) | 45453 |
| mlon_45455 | mlon | metabolomics | 2-oleoyl-GPE* (18:1)* | 45455 |
| mlon_45456 | mlon | metabolomics | 1-arachidoyl-GPC (20:0) | 45456 |
| mlon_45675 | mlon | metabolomics | 1-docosapentaenoyl-GPC* (22:5n6)* | 45675 |
| mlon_45721 | mlon | metabolomics | 3-(N-acetyl-L-cystein-S-yl) acetaminophen | 45721 |
| mlon_45951 | mlon | metabolomics | 1-linolenoyl-GPC (18:3)* | 45951 |
| mlon_45966 | mlon | metabolomics | 1-stearoyl-GPS (18:0)* | 45966 |
| mlon_45968 | mlon | metabolomics | 1-oleoyl-GPG (18:1)* | 45968 |
| mlon_45970 | mlon | metabolomics | 1-palmitoyl-GPG (16:0)* | 45970 |
| mlon_46106 | mlon | metabolomics | desmethylnaproxen sulfate | 46106 |
| mlon_46111 | mlon | metabolomics | guaiacol sulfate | 46111 |
| mlon_46115 | mlon | metabolomics | 21-hydroxypregnenolone disulfate | 46115 |
| mlon_46142 | mlon | metabolomics | mannitol/sorbitol | 46142 |
| mlon_46144 | mlon | metabolomics | methyl glucopyranoside (alpha + beta) | 46144 |
| mlon_46146 | mlon | metabolomics | 4-methylcatechol sulfate | 46146 |
| mlon_46164 | mlon | metabolomics | 3-methyl catechol sulfate (2) | 46164 |
| mlon_46165 | mlon | metabolomics | 3-methyl catechol sulfate (1) | 46165 |
| mlon_46172 | mlon | metabolomics | 5alpha-pregnan-diol disulfate | 46172 |
| mlon_46173 | mlon | metabolomics | aconitate [cis or trans] | 46173 |
| mlon_46203 | mlon | metabolomics | 2-docosahexaenoyl-GPC* (22:6)* | 46203 |
| mlon_46223 | mlon | metabolomics | linoleoylcarnitine (C18:2)* | 46223 |
| mlon_46225 | mlon | metabolomics | pyroglutamine* | 46225 |
| mlon_46301 | mlon | metabolomics | 9-HETE | 46301 |
| mlon_46331 | mlon | metabolomics | desmethylnaproxen | 46331 |
| mlon_46342 | mlon | metabolomics | leukotriene B5 | 46342 |
| mlon_46539 | mlon | metabolomics | N-acetylglucosamine/N-acetylgalactosamine | 46539 |
| mlon_46548 | mlon | metabolomics | 3-methylglutarylcarnitine (2) | 46548 |
| mlon_46798 | mlon | metabolomics | oleoyl-linoleoyl-glycerol (18:1/18:2) [1] | 46798 |
| mlon_46799 | mlon | metabolomics | oleoyl-linoleoyl-glycerol (18:1/18:2) [2] | 46799 |
| mlon_46957 | mlon | metabolomics | gulonate* | 46957 |
| mlon_46960 | mlon | metabolomics | sulfate* | 46960 |
| mlon_47031 | mlon | metabolomics | 2-methoxyacetaminophen sulfate* | 47031 |
| mlon_47101 | mlon | metabolomics | N-methylpipecolate | 47101 |
| mlon_47112 | mlon | metabolomics | etiocholanolone glucuronide | 47112 |
| mlon_47114 | mlon | metabolomics | ferulic acid 4-sulfate | 47114 |
| mlon_47118 | mlon | metabolomics | 2-palmitoleoyl-GPC* (16:1)* | 47118 |
| mlon_47120 | mlon | metabolomics | 9-hydroxystearate | 47120 |
| mlon_47132 | mlon | metabolomics | 5alpha-androstan-3alpha,17beta-diol 17-glucuronide | 47132 |
| mlon_47136 | mlon | metabolomics | N-acetyl-S-allyl-L-cysteine | 47136 |
| mlon_47153 | mlon | metabolomics | sphingomyelin (d18:1/24:1, d18:2/24:0)* | 47153 |
| mlon_47154 | mlon | metabolomics | sphingomyelin (d18:2/14:0, d18:1/14:1)* | 47154 |
| mlon_47403 | mlon | metabolomics | 17alpha-hydroxypregnanolone glucuronide | 47403 |
| mlon_47666 | mlon | metabolomics | alpha-CEHC sulfate | 47666 |
| mlon_47886 | mlon | metabolomics | bilirubin (E,Z or Z,E)* | 47886 |
| mlon_47888 | mlon | metabolomics | 1-eicosapentaenoyl-GPE (20:5)* | 47888 |
| mlon_47898 | mlon | metabolomics | 1-pentadecanoylglycerol (15:0) | 47898 |
| mlon_48143 | mlon | metabolomics | 2-propyl-4-pentenoate (4-ene-valproate) | 48143 |
| mlon_48153 | mlon | metabolomics | mannose | 48153 |
| mlon_48182 | mlon | metabolomics | myristoleoylcarnitine (C14:1)* | 48182 |

TABLE 2-continued

| Probe name | platform | data_type | official_symbol | EGID/COMP_ID |
|---|---|---|---|---|
| mlon_48187 | mlon | metabolomics | N-acetyltaurine | 48187 |
| mlon_48188 | mlon | metabolomics | alpha-CEHC | 48188 |
| mlon_48195 | mlon | metabolomics | fructose | 48195 |
| mlon_48255 | mlon | metabolomics | arabonate/xylonate | 48255 |
| mlon_48258 | mlon | metabolomics | 1-oleoyl-GPC (18:1) | 48258 |
| mlon_48259 | mlon | metabolomics | 2-oleoyl-GPC* (18:1)* | 48259 |
| mlon_48341 | mlon | metabolomics | 1-dihomo-linolenylglycerol (20:3) | 48341 |
| mlon_48351 | mlon | metabolomics | N1-methylinosine | 48351 |
| mlon_48394 | mlon | metabolomics | pregnanolone/allopregnanolone sulfate | 48394 |
| mlon_48406 | mlon | metabolomics | dopamine 4-sulfate | 48406 |
| mlon_48407 | mlon | metabolomics | dopamine 3-O-sulfate | 48407 |
| mlon_48408 | mlon | metabolomics | tyramine O-sulfate | 48408 |
| mlon_48425 | mlon | metabolomics | phenylacetylcarnitine | 48425 |
| mlon_48428 | mlon | metabolomics | pyrraline | 48428 |
| mlon_48429 | mlon | metabolomics | methyl-4-hydroxybenzoate sulfate | 48429 |
| mlon_48433 | mlon | metabolomics | N-formylphenylalanine | 48433 |
| mlon_48434 | mlon | metabolomics | N-acetylcitrulline | 48434 |
| mlon_48441 | mlon | metabolomics | 4-hydroxychlorothalonil | 48441 |
| mlon_48442 | mlon | metabolomics | 4-vinylguaiacol sulfate | 48442 |
| mlon_48445 | mlon | metabolomics | 2-methoxyresorcinol sulfate | 48445 |
| mlon_48448 | mlon | metabolomics | 3-hydroxypyridine sulfate | 48448 |
| mlon_48460 | mlon | metabolomics | propyl 4-hydroxybenzoate sulfate | 48460 |
| mlon_48490 | mlon | metabolomics | sphingomyelin (d18:1/20:0, d16:1/22:0)* | 48490 |
| mlon_48491 | mlon | metabolomics | sphingomyelin (d18:1/20:1, d18:2/20:0)* | 48491 |
| mlon_48492 | mlon | metabolomics | behenoyl sphingomyelin (d18:1/22:0)* | 48492 |
| mlon_48493 | mlon | metabolomics | sphingomyelin (d18:1/22:1, d18:2/22:0, d16:1/24:1)* | 48493 |
| mlon_485 | mlon | metabolomics | spermidine | 485 |
| mlon_48566 | mlon | metabolomics | valsartan | 48566 |
| mlon_48569 | mlon | metabolomics | acesulfame | 48569 |
| mlon_48580 | mlon | metabolomics | 2-acetamidophenol sulfate | 48580 |
| mlon_48674 | mlon | metabolomics | umbelliferone sulfate | 48674 |
| mlon_48693 | mlon | metabolomics | 3-acetylphenol sulfate | 48693 |
| mlon_48698 | mlon | metabolomics | 6-hydroxyindole sulfate | 48698 |
| mlon_48715 | mlon | metabolomics | eugenol sulfate | 48715 |
| mlon_48728 | mlon | metabolomics | daidzein sulfate (2) | 48728 |
| mlon_48733 | mlon | metabolomics | vanillic alcohol sulfate | 48733 |
| mlon_48757 | mlon | metabolomics | N-acetylkynurenine (2) | 48757 |
| mlon_48761 | mlon | metabolomics | 1,2,3-benzenetriol sulfate (1) | 48761 |
| mlon_48762 | mlon | metabolomics | 1,2,3-benzenetriol sulfate (2) | 48762 |
| mlon_48763 | mlon | metabolomics | 3-methoxycatechol sulfate (1) | 48763 |
| mlon_48782 | mlon | metabolomics | C-glycosyltryptophan | 48782 |
| mlon_48841 | mlon | metabolomics | p-cresol glucuronide* | 48841 |
| mlon_48857 | mlon | metabolomics | glycerophosphoglycerol | 48857 |
| mlon_48885 | mlon | metabolomics | arabitol/xylitol | 48885 |
| mlon_48990 | mlon | metabolomics | pyruvate | 48990 |
| mlon_48997 | mlon | metabolomics | isoeugenol sulfate | 48997 |
| mlon_49617 | mlon | metabolomics | 1-lignoceroyl-GPC (24:0) | 49617 |
| mlon_4968 | mlon | metabolomics | alpha-ketobutyrate | 4968 |
| mlon_5086 | mlon | metabolomics | dimethylglycine | 5086 |
| mlon_512 | mlon | metabolomics | asparagine | 512 |
| mlon_513 | mlon | metabolomics | creatinine | 513 |
| mlon_514 | mlon | metabolomics | cytidine | 514 |
| mlon_52234 | mlon | metabolomics | glycosyl-N-stearoyl-sphingosine (d18:1/18:0) | 52234 |
| mlon_52235 | mlon | metabolomics | 1-stearoyl-2-arachidonoyl-GPS (18:0/20:4) | 52235 |
| mlon_52281 | mlon | metabolomics | 2-hydroxybutyrate/2-hydroxyisobutyrate | 52281 |
| mlon_52285 | mlon | metabolomics | oleate/vaccenate (18:1) | 52285 |
| mlon_52294 | mlon | metabolomics | 2-hydroxyglutarate | 52294 |
| mlon_52322 | mlon | metabolomics | isoleucylleucine/leucylisoleucine | 52322 |
| mlon_52340 | mlon | metabolomics | N-carbamoylalanine | 52340 |
| mlon_52355 | mlon | metabolomics | N-desmethyl tramadol | 52355 |
| mlon_52357 | mlon | metabolomics | O-desmethyltramadol glucuronide | 52357 |
| mlon_52358 | mlon | metabolomics | N,O-didesmethylvenlafaxine glucuronide | 52358 |
| mlon_52415 | mlon | metabolomics | leucylphenylalanine/isoleucylphenylalanine | 52415 |
| mlon_52431 | mlon | metabolomics | 1-palmitoleoylglycerol (16:1)* | 52431 |
| mlon_52433 | mlon | metabolomics | sphingomyelin (d17:1/16:0, d18:1/15:0, d16:1/17:0)* | 52433 |
| mlon_52434 | mlon | metabolomics | palmitoyl dihydrosphingomyelin (d18:0/16:0)* | 52434 |
| mlon_52435 | mlon | metabolomics | sphingomyelin (d18:2/23:0, d18:1/23:1, d17:1/24:1)* | 52435 |
| mlon_52436 | mlon | metabolomics | tricosanoyl sphingomyelin (d18:1/23:0)* | 52436 |
| mlon_52437 | mlon | metabolomics | sphingomyelin (d18:2/24:1, d18:1/24:2)* | 52437 |
| mlon_52438 | mlon | metabolomics | 1-stearoyl-2-oleoyl-GPC (18:0/18:1) | 52438 |
| mlon_52446 | mlon | metabolomics | 1-stearoyl-2-linoleoyl-GPE (18:0/18:2)* | 52446 |
| mlon_52447 | mlon | metabolomics | 1-stearoyl-2-arachidonoyl-GPE (18:0/20:4) | 52447 |
| mlon_52449 | mlon | metabolomics | 1-stearoyl-2-arachidonoyl-GPI (18:0/20:4) | 52449 |
| mlon_52450 | mlon | metabolomics | 1-palmitoyl-2-linoleoyl-GPI (16:0/18:2) | 52450 |
| mlon_52452 | mlon | metabolomics | 1-stearoyl-2-linoleoyl-GPC (18:0/18:2)* | 52452 |
| mlon_52454 | mlon | metabolomics | 1-palmitoyl-2-dihomo-linolenoyl-GPC (16:0/20:3n3 or 6)* | 52454 |

TABLE 2-continued

| Probe name | platform | data_type | official_symbol | EGID/COMP_ID |
|---|---|---|---|---|
| mlon_52461 | mlon | metabolomics | 1-palmitoyl-2-oleoyl-GPC (16:0/18:1) | 52461 |
| mlon_52462 | mlon | metabolomics | 1-palmitoyl-2-arachidonoyl-GPC (16:0/20:4n6) | 52462 |
| mlon_52463 | mlon | metabolomics | 1-palmitoyl-2-eicosapentaenoyl-GPC (16:0/20:5)* | 52463 |
| mlon_52464 | mlon | metabolomics | 1-palmitoyl-2-arachidonoyl-GPE (16:0/20:4)* | 52464 |
| mlon_52465 | mlon | metabolomics | 1-palmitoyl-2-docosahexaenoyl-GPE (16:0/22:6)* | 52465 |
| mlon_52466 | mlon | metabolomics | 1-stearoyl-2-docosahexaenoyl-GPE (18:0/22:6)* | 52466 |
| mlon_52467 | mlon | metabolomics | 1-palmitoyl-2-arachidonoyl-GPI (16:0/20:4)* | 52467 |
| mlon_52468 | mlon | metabolomics | 1-stearoyl-2-linoleoyl-GPI (18:0/18:2) | 52468 |
| mlon_52470 | mlon | metabolomics | 1-palmitoyl-2-palmitoleoyl-GPC (16:0/16:1)* | 52470 |
| mlon_52471 | mlon | metabolomics | 1-palmitoyl-2-palmitoleoyl-GPE (16:0/16:1)* | 52471 |
| mlon_52473 | mlon | metabolomics | gamma-tocopherol/beta-tocopherol | 52473 |
| mlon_52474 | mlon | metabolomics | 1-(1-enyl-palmitoyl)-GPC (P-16:0)* | 52474 |
| mlon_52475 | mlon | metabolomics | 1-(1-enyl-stearoyl)-2-arachidonoyl-GPE (P-18:0/20:4)* | 52475 |
| mlon_52476 | mlon | metabolomics | 1-(1-enyl-stearoyl)-2-docosahexaenoyl-GPE (P-18:0/22:6)* | 52476 |
| mlon_52477 | mlon | metabolomics | 1-(1-enyl-palmitoyl)-2-oleoyl-GPE (P-16:0/18:1)* | 52477 |
| mlon_52478 | mlon | metabolomics | 1-(1-enyl-palmitoyl)-2-oleoyl-GPC (P-16:0/18:1)* | 52478 |
| mlon_52495 | mlon | metabolomics | sphingomyelin (d18:1/21:0, d17:1/22:0, d16:1/23:0)* | 52495 |
| mlon_52497 | mlon | metabolomics | 1-pentadecanoyl-2-linoleoyl-GPC (15:0/18:2)* | 52497 |
| mlon_52499 | mlon | metabolomics | 1-margaroyl-2-oleoyl-GPC (17:0/18:1)* | 52499 |
| mlon_52500 | mlon | metabolomics | 1-margaroyl-2-linoleoyl-GPC (17:0/18:2)* | 52500 |
| mlon_52603 | mlon | metabolomics | 1,2-dilinoleoyl-GPC (18:2/18:2) | 52603 |
| mlon_52604 | mlon | metabolomics | N-palmitoyl-sphinganine (d18:0/16:0) | 52604 |
| mlon_52605 | mlon | metabolomics | sphinganine-1-phosphate | 52605 |
| mlon_52608 | mlon | metabolomics | linoleoyl ethanolamide | 52608 |
| mlon_52610 | mlon | metabolomics | 1-palmitoyl-2-docosahexaenoyl-GPC (16:0/22:6) | 52610 |
| mlon_52611 | mlon | metabolomics | 1-stearoyl-2-docosahexaenoyl-GPC (18:0/22:6) | 52611 |
| mlon_52612 | mlon | metabolomics | 1-(1-enyl-stearoyl)-2-oleoyl-GPC (P-18:0/18:1) | 52612 |
| mlon_52613 | mlon | metabolomics | 1-(1-enyl-stearoyl)-2-arachidonoyl-GPC (P-18:0/20:4) | 52613 |
| mlon_52614 | mlon | metabolomics | 1-(1-enyl-stearoyl)-2-oleoyl-GPE (P-18:0/18:1) | 52614 |
| mlon_52615 | mlon | metabolomics | sphingomyelin (d18:1/17:0, d17:1/18:0, d19:1/16:0) | 52615 |
| mlon_52616 | mlon | metabolomics | 1-palmitoyl-2-stearoyl-GPC (16:0/18:0) | 52616 |
| mlon_52623 | mlon | metabolomics | 1-stearoyl-2-oleoyl-GPG (18:0/18:1) | 52623 |
| mlon_52629 | mlon | metabolomics | 1-stearoyl-2-dihomo-linolenoyl-GPC (18:0/20:3n3 or 6)* | 52629 |
| mlon_52630 | mlon | metabolomics | 1-(1-enyl-palmitoyl)-2-docosahexaenoyl-GPC (P-16:0/22:6)* | 52630 |
| mlon_52631 | mlon | metabolomics | palmitoleoyl-oleoyl-glycerol (16:1/18:1) [2]* | 52631 |
| mlon_52632 | mlon | metabolomics | palmitoleoyl-oleoyl-glycerol (16:1/18:1) [1]* | 52632 |
| mlon_52633 | mlon | metabolomics | palmitoyl-linoleoyl-glycerol (16:0/18:2) [1]* | 52633 |
| mlon_52634 | mlon | metabolomics | palmitoyl-linoleoyl-glycerol (16:0/18:2) [2]* | 52634 |
| mlon_52668 | mlon | metabolomics | 1-stearoyl-2-docosahexaenoyl-GPI (18:0/22:6)* | 52668 |
| mlon_52669 | mlon | metabolomics | 1-palmitoyl-2-oleoyl-GPI (16:0/18:1)* | 52669 |
| mlon_52672 | mlon | metabolomics | 1-(1-enyl-palmitoyl)-2-docosahexaenoyl-GPE (P-16:0/22:6)* | 52672 |
| mlon_52673 | mlon | metabolomics | 1-(1-enyl-palmitoyl)-2-arachidonoyl-GPE (P-16:0/20:4)* | 52673 |
| mlon_52677 | mlon | metabolomics | 1-(1-enyl-palmitoyl)-2-linoleoyl-GPE (P-16:0/18:2)* | 52677 |
| mlon_52682 | mlon | metabolomics | 1-(1-enyl-palmitoyl)-2-linoleoyl-GPC (P-16:0/18:2)* | 52682 |
| mlon_52687 | mlon | metabolomics | 1-oleoyl-2-linoleoyl-GPE (18:1/18:2)* | 52687 |
| mlon_52689 | mlon | metabolomics | 1-(1-enyl-palmitoyl)-2-arachidonoyl-GPC (P-16:0/20:4)* | 52689 |
| mlon_52690 | mlon | metabolomics | 1-linoleoyl-GPA (18:2)* | 52690 |
| mlon_52697 | mlon | metabolomics | 1-oleoyl-2-docosahexaenoyl-GPC (18:1/22:6)* | 52697 |
| mlon_52698 | mlon | metabolomics | 1-adrenoyl-GPC (22:4)* | 52698 |
| mlon_52699 | mlon | metabolomics | 1-stearoyl-2-docosapentaenoyl-GPC (18:0/22:5n3)* | 52699 |
| mlon_527 | mlon | metabolomics | lactate | 527 |
| mlon_52700 | mlon | metabolomics | 1-stearoyl-2-docosapentaenoyl-GPC (18:0/22:5n6)* | 52700 |
| mlon_52701 | mlon | metabolomics | 1-(1-enyl-oleoyl)-GPC (P-18:1)* | 52701 |
| mlon_52702 | mlon | metabolomics | 1-(1-enyl-stearoyl)-GPC (P-18:0)* | 52702 |
| mlon_52703 | mlon | metabolomics | 1-stearyl-GPC (O-18:0)* | 52703 |
| mlon_52704 | mlon | metabolomics | 1-(1-enyl-stearoyl)-2-docosahexaenoyl-GPC (P-18:0/22:6)* | 52704 |
| mlon_52705 | mlon | metabolomics | 1-oleoyl-2-dihomo-linolenoyl-GPC (18:1/20:3)* | 52705 |
| mlon_52706 | mlon | metabolomics | 1-palmitoyl-2-adrenoyl-GPC (16:0/22:4)* | 52706 |
| mlon_52707 | mlon | metabolomics | 1-myristoyl-2-linoleoyl-GPC (14:0/18:2)* | 52707 |
| mlon_52710 | mlon | metabolomics | 1-linoleoyl-2-arachidonoyl-GPC (18:2/20:4n6)* | 52710 |
| mlon_52712 | mlon | metabolomics | 1-(1-enyl-stearoyl)-2-linoleoyl-GPC (P-18:0/18:2)* | 52712 |
| mlon_52713 | mlon | metabolomics | 1-(1-enyl-palmitoyl)-2-palmitoleoyl-GPC (P-16:0/16:1)* | 52713 |
| mlon_52714 | mlon | metabolomics | 1-(1-enyl-palmitoyl)-2-dihomo-linolenoyl-GPC (P-16:0/20:3)* | 52714 |
| mlon_52715 | mlon | metabolomics | 1-(1-enyl-palmitoyl)-2-myristoyl-GPC (P-16:0/14:0)* | 52715 |
| mlon_52716 | mlon | metabolomics | 1-(1-enyl-palmitoyl)-2-palmitoyl-GPC (P-16:0/16:0)* | 52716 |
| mlon_52717 | mlon | metabolomics | 1-palmityl-2-oleoyl-GPC (0-16:0/18:1)* | 52717 |
| mlon_52718 | mlon | metabolomics | 1-palmityl-2-arachidonoyl-GPC (O-16:0/20:4)* | 52718 |
| mlon_52719 | mlon | metabolomics | phosphatidylcholine (16:0/22:5n3, 18:1/20:4)* | 52719 |
| mlon_52726 | mlon | metabolomics | 1-stearoyl-2-oleoyl-GPI (18:0/18:1)* | 52726 |

TABLE 2-continued

| Probe name | platform | data_type | official_symbol | EGID/COMP_ID |
|---|---|---|---|---|
| mlon_52748 | mlon | metabolomics | 1-(1-enyl-stearoyl)-2-linoleoyl-GPE (P-18:0/18:2)* | 52748 |
| mlon_528 | mlon | metabolomics | alpha-ketoglutarate | 528 |
| mlon_52913 | mlon | metabolomics | pregabalin | 52913 |
| mlon_52914 | mlon | metabolomics | 5-hydroxyindole sulfate | 52914 |
| mlon_52915 | mlon | metabolomics | 7-hydroxyindole sulfate | 52915 |
| mlon_52925 | mlon | metabolomics | phenylacetylglutamate | 52925 |
| mlon_52929 | mlon | metabolomics | 3,4-methyleneheptanoylcarnitine | 52929 |
| mlon_52932 | mlon | metabolomics | 4-hydroxyphenylacetatoylcarnitine | 52932 |
| mlon_52944 | mlon | metabolomics | palmitoylcholine | 52944 |
| mlon_52949 | mlon | metabolomics | enalapril | 52949 |
| mlon_52954 | mlon | metabolomics | sitagliptin | 52954 |
| mlon_52955 | mlon | metabolomics | ezetimibe | 52955 |
| mlon_52958 | mlon | metabolomics | rivaroxaban | 52958 |
| mlon_52974 | mlon | metabolomics | glycochenodeoxycholate sulfate | 52974 |
| mlon_52975 | mlon | metabolomics | glycodeoxycholate sulfate | 52975 |
| mlon_52983 | mlon | metabolomics | glycochenodeoxycholate glucuronide (1) | 52983 |
| mlon_52984 | mlon | metabolomics | 3-hydroxybutyrylcarnitine (2) | 52984 |
| mlon_52988 | mlon | metabolomics | adipoylcarnitine (C6-DC) | 52988 |
| mlon_52990 | mlon | metabolomics | suberoylcarnitine (C8-DC) | 52990 |
| mlon_53 | mlon | metabolomics | glutamine | 53 |
| mlon_53010 | mlon | metabolomics | lactosyl-N-palmitoyl-sphingosine (d18:1/16:0) | 53010 |
| mlon_53013 | mlon | metabolomics | glycosyl-N-palmitoyl-sphingosine (d18:1/16:0) | 53013 |
| mlon_53026 | mlon | metabolomics | 3,4-methyleneheptanoate | 53026 |
| mlon_53031 | mlon | metabolomics | methylsuccinoylcarnitine | 53031 |
| mlon_531 | mlon | metabolomics | 3-hydroxy-3-methylglutarate | 531 |
| mlon_53174 | mlon | metabolomics | 1,2-dilinoleoyl-GPE (18:2/18:2)* | 53174 |
| mlon_53175 | mlon | metabolomics | 1-palmityl-2-linoleoyl-GPC (O-16:0/18:2)* | 53175 |
| mlon_53176 | mlon | metabolomics | 1-linoleoyl-2-linolenoyl-GPC (18:2/18:3)* | 53176 |
| mlon_53177 | mlon | metabolomics | phosphatidylcholine (14:0/14:0, 16:0/12:0) | 53177 |
| mlon_53178 | mlon | metabolomics | phosphatidylcholine (15:0/18:1, 17:0/16:1, 16:0/17:1)* | 53178 |
| mlon_53190 | mlon | metabolomics | 1-palmitoyl-2-eicosapentaenoyl-GPE (16:0/20:5)* | 53190 |
| mlon_53192 | mlon | metabolomics | phosphatidylcholine (18:0/20:2, 20:0/18:2)* | 53192 |
| mlon_53193 | mlon | metabolomics | 1-margaroyl-2-arachidonoyl-GPC (17:0/20:4)* | 53193 |
| mlon_53194 | mlon | metabolomics | 1-pentadecanoyl-2-arachidonoyl-GPC (15:0/20:4)* | 53194 |
| mlon_53195 | mlon | metabolomics | 1-myristoyl-2-arachidonoyl-GPC (14:0/20:4)* | 53195 |
| mlon_53196 | mlon | metabolomics | 1-myristoyl-2-docosahexaenoyl-GPC (14:0/22:6)* | 53196 |
| mlon_53197 | mlon | metabolomics | 1-pentadecanoyl-2-docosahexaenoyl-GPC (15:0/22:6)* | 53197 |
| mlon_53198 | mlon | metabolomics | 1-margaroyl-2-docosahexaenoyl-GPC (17:0/22:6)* | 53198 |
| mlon_53199 | mlon | metabolomics | 1-linoleoyl-2-docosahexaenoyl-GPC (18:2/22:6)* | 53199 |
| mlon_53202 | mlon | metabolomics | 1-oleoyl-2-docosapentaenoyl-GPC (18:1/22:5n3)* | 53202 |
| mlon_53209 | mlon | metabolomics | 1-oleoyl-2-docosahexaenoyl-GPE (18:1/22:6)* | 53209 |
| mlon_53211 | mlon | metabolomics | 1-linoleoyl-2-docosapentaenyol-GPC (18:2/22:5n3)* | 53211 |
| mlon_53223 | mlon | metabolomics | palmitoleoylcarnitine (C16:1)* | 53223 |
| mlon_53224 | mlon | metabolomics | pimeloylcarnitine/3-methyladipoylcarnitine (C7-DC) | 53224 |
| mlon_53230 | mlon | metabolomics | 3-hydroxyhexanoate | 53230 |
| mlon_53231 | mlon | metabolomics | thioproline | 53231 |
| mlon_53239 | mlon | metabolomics | O-desmethyltramadol | 53239 |
| mlon_53241 | mlon | metabolomics | tramadol | 53241 |
| mlon_53242 | mlon | metabolomics | 5-bromotryptophan | 53242 |
| mlon_53243 | mlon | metabolomics | catechol glucuronide | 53243 |
| mlon_53254 | mlon | metabolomics | caffeic acid sulfate | 53254 |
| mlon_53257 | mlon | metabolomics | palmitoleoylcholine | 53257 |
| mlon_53260 | mlon | metabolomics | oleoylcholine | 53260 |
| mlon_53261 | mlon | metabolomics | arachidonoylcholine | 53261 |
| mlon_53262 | mlon | metabolomics | dihomo-linolenoyl-choline | 53262 |
| mlon_53263 | mlon | metabolomics | docosahexaenoylcholine | 53263 |
| mlon_54 | mlon | metabolomics | tryptophan | 54 |
| mlon_542 | mlon | metabolomics | 3-hydroxybutyrate (BHBA) | 542 |
| mlon_54742 | mlon | metabolomics | prednisolone | 54742 |
| mlon_54745 | mlon | metabolomics | cetirizine | 54745 |
| mlon_54762 | mlon | metabolomics | lamotrigine | 54762 |
| mlon_54784 | mlon | metabolomics | chlorthalidone | 54784 |
| mlon_54805 | mlon | metabolomics | 3beta-hydroxy-5-cholestenoate | 54805 |
| mlon_54812 | mlon | metabolomics | 1-palmitoyl-2-gamma-linolenoyl-GPC (16:0/18:3n6)* | 54812 |
| mlon_54885 | mlon | metabolomics | 1-linoleoyl-GPG (18:2)* | 54885 |
| mlon_54907 | mlon | metabolomics | hexanoylglutamine | 54907 |
| mlon_54910 | mlon | metabolomics | vanillactate | 54910 |
| mlon_54923 | mlon | metabolomics | beta-citrylglutamate | 54923 |
| mlon_54942 | mlon | metabolomics | palmitoyl-oleoyl-glycerol (16:0/18:1) [2]* | 54942 |
| mlon_54943 | mlon | metabolomics | palmitoyl-oleoyl-glycerol (16:0/18:1) [1]* | 54943 |
| mlon_54945 | mlon | metabolomics | oleoyl-oleoyl-glycerol (18:1/18:1) [1]* | 54945 |
| mlon_54946 | mlon | metabolomics | oleoyl-oleoyl-glycerol (18:1/18:1) [2]* | 54946 |
| mlon_54953 | mlon | metabolomics | diacylglycerol (14:0/18:1, 16:0/16:1) [1]* | 54953 |
| mlon_54954 | mlon | metabolomics | diacylglycerol (14:0/18:1, 16:0/16:1) [2]* | 54954 |
| mlon_54955 | mlon | metabolomics | linoleoyl-arachidonoyl-glycerol (18:2/20:4) [1]* | 54955 |
| mlon_54956 | mlon | metabolomics | linoleoyl-arachidonoyl-glycerol (18:2/20:4) [2]* | 54956 |
| mlon_54957 | mlon | metabolomics | palmitoyl-arachidonoyl-glycerol (16:0/20:4) [1]* | 54957 |
| mlon_54958 | mlon | metabolomics | palmitoyl-arachidonoyl-glycerol (16:0/20:4) [2]* | 54958 |

TABLE 2-continued

| Probe name | platform | data_type | official_symbol | EGID/COMP_ID |
|---|---|---|---|---|
| mlon_54960 | mlon | metabolomics | oleoyl-arachidonoyl-glycerol (18:1/20:4) [1]* | 54960 |
| mlon_54961 | mlon | metabolomics | oleoyl-arachidonoyl-glycerol (18:1/20:4) [2]* | 54961 |
| mlon_54963 | mlon | metabolomics | linoleoyl-linolenoyl-glycerol (18:2/18:3) [1]* | 54963 |
| mlon_54964 | mlon | metabolomics | linoleoyl-linolenoyl-glycerol (18:2/18:3) [2]* | 54964 |
| mlon_54966 | mlon | metabolomics | diacylglycerol (16:1/18:2 [2], 16:0/18:3 [1])* | 54966 |
| mlon_54967 | mlon | metabolomics | palmitoleoyl-linoleoyl-glycerol (16:1/18:2) [1]* | 54967 |
| mlon_54968 | mlon | metabolomics | linoleoyl-linoleoyl-glycerol (18:2/18:2) [1]* | 54968 |
| mlon_54969 | mlon | metabolomics | linoleoyl-linoleoyl-glycerol (18:2/18:2) [2]* | 54969 |
| mlon_54970 | mlon | metabolomics | oleoyl-linolenoyl-glycerol (18:1/18:3) [2]* | 54970 |
| mlon_54979 | mlon | metabolomics | N-stearoyl-sphingosine (d18:1/18:0)* | 54979 |
| mlon_54984 | mlon | metabolomics | 1-stearoyl-2-dihomo-linolenoyl-GPI (18:0/20:3n3 or 6)* | 54984 |
| mlon_54990 | mlon | metabolomics | palmitoyl-palmitoyl-glycerol (16:0/16:0) [2]* | 54990 |
| mlon_55 | mlon | metabolomics | beta-alanine | 55 |
| mlon_55003 | mlon | metabolomics | 1-myristoyl-2-palmitoleoyl-GPC (14:0/16:1)* | 55003 |
| mlon_55007 | mlon | metabolomics | 1-palmityl-GPE (O-16:0)* | 55007 |
| mlon_55015 | mlon | metabolomics | gamma-glutamyl-alpha-lysine | 55015 |
| mlon_55017 | mlon | metabolomics | 4-hydroxyphenylacetylglutamine | 55017 |
| mlon_55037 | mlon | metabolomics | 1-(1-enyl-oleoyl)-2-docosahexaenoyl-GPE (P-18:1/22:6)* | 55037 |
| mlon_55040 | mlon | metabolomics | 1-palmityl-2-stearoyl-GPC (O-16:0/18:0)* | 55040 |
| mlon_55061 | mlon | metabolomics | 1-stearoyl-2-adrenoyl-GPC (18:0/22:4)* | 55061 |
| mlon_55062 | mlon | metabolomics | 1-arachidoyl-2-arachidonoyl-GPC (20:0/20:4)* | 55062 |
| mlon_55070 | mlon | metabolomics | 1-erucoyl-GPC (22:1)* | 55070 |
| mlon_55072 | mlon | metabolomics | 2-oxoarginine* | 55072 |
| mlon_553 | mlon | metabolomics | cotinine | 553 |
| mlon_554 | mlon | metabolomics | adenine | 554 |
| mlon_555 | mlon | metabolomics | adenosine | 555 |
| mlon_558 | mlon | metabolomics | adenosine 5'-diphosphoribose (ADP-ribose) | 558 |
| mlon_56 | mlon | metabolomics | cystine | 56 |
| mlon_566 | mlon | metabolomics | phenylpyruvate | 566 |
| mlon_568 | mlon | metabolomics | biotin | 568 |
| mlon_569 | mlon | metabolomics | caffeine | 569 |
| mlon_57 | mlon | metabolomics | glutamate | 57 |
| mlon_57317 | mlon | metabolomics | 1-palmitoleoyl-2-arachidonoyl-GPC (16:1/20:4)* | 57317 |
| mlon_57330 | mlon | metabolomics | lignoceroyl sphingomyelin (d18:1/24:0) | 57330 |
| mlon_57331 | mlon | metabolomics | behenoyl dihydrosphingomyelin (d18:0/22:0)* | 57331 |
| mlon_57332 | mlon | metabolomics | 1-palmityl-2-palmitoyl-GPC (O-16:0/16:0)* | 57332 |
| mlon_57333 | mlon | metabolomics | 1-stearyl-2-arachidonoyl-GPC (O-18:0/20:4)* | 57333 |
| mlon_57334 | mlon | metabolomics | 1-stearyl-2-docosapentaenoyl-GPC (O-18:0/22:5n3)* | 57334 |
| mlon_57335 | mlon | metabolomics | phosphatidylcholine (16:0/20:4n3; 18:1/18:3n6)* | 57335 |
| mlon_57336 | mlon | metabolomics | 1-stearoyl-2-dihomo-linolenoyl-GPE (18:0/20:3n3 or 6)* | 57336 |
| mlon_57338 | mlon | metabolomics | 1-stearoyl-2-docosapentaenoyl-GPE (18:0/22:5n6)* | 57338 |
| mlon_57339 | mlon | metabolomics | 1-stearoyl-2-adrenoyl-GPE (18:0/22:4)* | 57339 |
| mlon_57342 | mlon | metabolomics | 1-(1-enyl-stearoyl)-2-docosapentaenoyl-GPE (P-18:0/22:5n3)* | 57342 |
| mlon_57343 | mlon | metabolomics | 1-(1-enyl-stearoyl)-2-dihomo-linolenoyl-GPE (P-18:0/20:3)* | 57343 |
| mlon_57365 | mlon | metabolomics | myristoyl dihydrosphingomyelin (d18:0/14:0)* | 57365 |
| mlon_57370 | mlon | metabolomics | lactosyl-N-nervonoyl-sphingosine (d18:1/24:1)* | 57370 |
| mlon_57372 | mlon | metabolomics | N-behenoyl-sphingadienine (d18:2/22:0)* | 57372 |
| mlon_57373 | mlon | metabolomics | palmitoyl-docosahexaenoyl-glycerol (16:0/22:6) [1]* | 57373 |
| mlon_57406 | mlon | metabolomics | palmitoleoyl-arachidonoyl-glycerol (16:1/20:4) [2]* | 57406 |
| mlon_57407 | mlon | metabolomics | myristoyl-linoleoyl-glycerol (14:0/18:2) [1]* | 57407 |
| mlon_57408 | mlon | metabolomics | myristoyl-linoleoyl-glycerol (14:0/18:2) [2]* | 57408 |
| mlon_57411 | mlon | metabolomics | phosphatidylethanolamine (P-18:1/20:4, P-16:0/22:5n3)* | 57411 |
| mlon_57415 | mlon | metabolomics | 1-palmitoyl-2-(hydroxylinoleoyl)-GPC (16:0/18:2(OH))* | 57415 |
| mlon_57421 | mlon | metabolomics | glycosyl-N-behenoyl-sphingadienine (d18:2/22:0)* | 57421 |
| mlon_57426 | mlon | metabolomics | sphingadienine | 57426 |
| mlon_57428 | mlon | metabolomics | hexadecasphingosine (d16:1)* | 57428 |
| mlon_57430 | mlon | metabolomics | N-palmitoyl-heptadecasphingosine (d17:1/16:0)* | 57430 |
| mlon_57432 | mlon | metabolomics | ceramide (d18:1/14:0, d16:1/16:0)* | 57432 |
| mlon_57434 | mlon | metabolomics | ceramide (d18:1/17:0, d17:1/18:0)* | 57434 |
| mlon_57437 | mlon | metabolomics | ceramide (d16:1/24:1, d18:1/22:1)* | 57437 |
| mlon_57440 | mlon | metabolomics | ceramide (d18:1/20:0, d16:1/22:0, d20:1/18:0)* | 57440 |
| mlon_57443 | mlon | metabolomics | ceramide (d18:2/24:1, d18:1/24:2)* | 57443 |
| mlon_57448 | mlon | metabolomics | glycosyl ceramide (d18:1/23:1, d17:1/24:1)* | 57448 |
| mlon_57449 | mlon | metabolomics | stearoyl-arachidonoyl-glycerol (18:0/20:4) [2]* | 57449 |
| mlon_57450 | mlon | metabolomics | stearoyl-arachidonoyl-glycerol (18:0/20:4) [1]* | 57450 |
| mlon_57453 | mlon | metabolomics | glycosyl ceramide (d18:2/24:1, d18:1/24:2)* | 57453 |
| mlon_57457 | mlon | metabolomics | glycosyl ceramide (d16:1/24:1, d18:1/22:1)* | 57457 |
| mlon_57461 | mlon | metabolomics | argininate* | 57461 |
| mlon_57463 | mlon | metabolomics | linoleoylcholine* | 57463 |
| mlon_57464 | mlon | metabolomics | stearoylcholine* | 57464 |
| mlon_57473 | mlon | metabolomics | sphingomyelin (d18:0/18:0, d19:0/17:0)* | 57473 |

TABLE 2-continued

| Probe name | platform | data_type | official_symbol | EGID/COMP_ID |
|---|---|---|---|---|
| mlon_57474 | mlon | metabolomics | sphingomyelin (d18:2/18:1)* | 57474 |
| mlon_57475 | mlon | metabolomics | sphingomyelin (d18:1/19:0, d19:1/18:0)* | 57475 |
| mlon_57476 | mlon | metabolomics | sphingomyelin (d18:0/20:0, d16:0/22:0)* | 57476 |
| mlon_57477 | mlon | metabolomics | sphingomyelin (d18:1/22:2, d18:2/22:1, d16:1/24:2)* | 57477 |
| mlon_57478 | mlon | metabolomics | sphingomyelin (d18:1/25:0, d19:0/24:1, d20:1/23:0, d19:1/24:0)* | 57478 |
| mlon_57479 | mlon | metabolomics | sphingomyelin (d18:2/24:2)* | 57479 |
| mlon_57480 | mlon | metabolomics | sphingomyelin (d18:2/21:0, d16:2/23:0)* | 57480 |
| mlon_57481 | mlon | metabolomics | sphingomyelin (d18:1/20:2, d18:2/20:1, d16:1/22:2)* | 57481 |
| mlon_57482 | mlon | metabolomics | sphingomyelin (d18:2/23:1)* | 57482 |
| mlon_57483 | mlon | metabolomics | sphingomyelin (d17:2/16:0, d18:2/15:0)* | 57483 |
| mlon_575 | mlon | metabolomics | arabinose | 575 |
| mlon_57509 | mlon | metabolomics | 1-linolenoyl-GPE (18:3)* | 57509 |
| mlon_57511 | mlon | metabolomics | linolenoylcarnitine (C18:3)* | 57511 |
| mlon_57512 | mlon | metabolomics | margaroylcarnitine (C17)* | 57512 |
| mlon_57513 | mlon | metabolomics | arachidoylcarnitine (C20)* | 57513 |
| mlon_57514 | mlon | metabolomics | behenoylcarnitine (C22)* | 57514 |
| mlon_57515 | mlon | metabolomics | lignoceroylcarnitine (C24)* | 57515 |
| mlon_57516 | mlon | metabolomics | cerotoylcarnitine (C26)* | 57516 |
| mlon_57517 | mlon | metabolomics | ximenoylcarnitine (C26:1)* | 57517 |
| mlon_57518 | mlon | metabolomics | arachidonoylcarnitine (C20:4) | 57518 |
| mlon_57519 | mlon | metabolomics | eicosenoylcarnitine (C20:1)* | 57519 |
| mlon_57520 | mlon | metabolomics | dihomo-linoleoylcarnitine (C20:2)* | 57520 |
| mlon_57521 | mlon | metabolomics | dihomo-linolenoylcarnitine (C20:3n3 or 6)* | 57521 |
| mlon_57523 | mlon | metabolomics | docosahexaenoylcarnitine (C22:6)* | 57523 |
| mlon_57528 | mlon | metabolomics | adrenoylcarnitine (C22:4)* | 57528 |
| mlon_57531 | mlon | metabolomics | nervonoylcarnitine (C24:1)* | 57531 |
| mlon_57547 | mlon | metabolomics | 2,3-dihydroxy-2-methylbutyrate | 57547 |
| mlon_57564 | mlon | metabolomics | perfluorooctanesulfonate (PFOS) | 57564 |
| mlon_57577 | mlon | metabolomics | isoursodeoxycholate | 57577 |
| mlon_57591 | mlon | metabolomics | beta-cryptoxanthin | 57591 |
| mlon_57595 | mlon | metabolomics | glycosyl ceramide (d18:1/20:0, d16:1/22:0)* | 57595 |
| mlon_57603 | mlon | metabolomics | 1-nervonoyl-2-arachidonoyl-GPC (24:1/20:4)* | 57603 |
| mlon_57614 | mlon | metabolomics | ciprofloxacin | 57614 |
| mlon_57635 | mlon | metabolomics | carotene diol (1) | 57635 |
| mlon_57636 | mlon | metabolomics | carotene diol (2) | 57636 |
| mlon_57637 | mlon | metabolomics | carotene diol (3) | 57637 |
| mlon_57641 | mlon | metabolomics | levetiracetam | 57641 |
| mlon_57652 | mlon | metabolomics | hexadecadienoate (16:2n6) | 57652 |
| mlon_57655 | mlon | metabolomics | 2'-O-methyluridine | 57655 |
| mlon_57659 | mlon | metabolomics | N-palmitoylserine | 57659 |
| mlon_57664 | mlon | metabolomics | N-oleoylserine | 57664 |
| mlon_57687 | mlon | metabolomics | N,N,N-trimethyl-5-aminovalerate | 57687 |
| mlon_57691 | mlon | metabolomics | trazadone | 57691 |
| mlon_57707 | mlon | metabolomics | fluconazole | 57707 |
| mlon_57709 | mlon | metabolomics | ADSGEGDFXAEGGGVR* | 57709 |
| mlon_57778 | mlon | metabolomics | 2-propyl-2-pentenoate (2-ene-valproate) | 57778 |
| mlon_57781 | mlon | metabolomics | 3-hydroxyvalproate | 57781 |
| mlon_58 | mlon | metabolomics | glycine | 58 |
| mlon_587 | mlon | metabolomics | gluconate | 587 |
| mlon_59 | mlon | metabolomics | histidine | 59 |
| mlon_590 | mlon | metabolomics | hypotaurine | 590 |
| mlon_594 | mlon | metabolomics | nicotinamide | 594 |
| mlon_5983 | mlon | metabolomics | corticosterone | 5983 |
| mlon_60 | mlon | metabolomics | leucine | 60 |
| mlon_601 | mlon | metabolomics | dihydroorotate | 601 |
| mlon_605 | mlon | metabolomics | uracil | 605 |
| mlon_606 | mlon | metabolomics | uridine | 606 |
| mlon_607 | mlon | metabolomics | trans-urocanate | 607 |
| mlon_6146 | mlon | metabolomics | 2-aminoadipate | 6146 |
| mlon_61832 | mlon | metabolomics | 5-hydroxyvalproate | 61832 |
| mlon_61844 | mlon | metabolomics | morphine-3-glucuronide | 61844 |
| mlon_61845 | mlon | metabolomics | morphine-6-glucuronide | 61845 |
| mlon_62479 | mlon | metabolomics | citalopram propionate* | 62479 |
| mlon_62480 | mlon | metabolomics | 4-hydroxy duloxetine glucuronide* | 62480 |
| mlon_62481 | mlon | metabolomics | 5-hydroxy-6-methoxy duloxetine sulfate* | 62481 |
| mlon_62483 | mlon | metabolomics | ezetimibe glucuronide * | 62483 |
| mlon_62484 | mlon | metabolomics | N-desalkylquetiapine* | 62484 |
| mlon_62485 | mlon | metabolomics | ranitidine N-oxide* | 62485 |
| mlon_63 | mlon | metabolomics | cholesterol | 63 |
| mlon_64 | mlon | metabolomics | phenylalanine | 64 |

Protein or Polypeptide Data

Disclosed herein are algorithms, classifiers, or models that generate classifications of individuals based on input data including protein or polypeptide data. Protein or polypeptide data can include information regarding the identity and/or quantity of one or more proteins or polypeptides obtained from a biological sample. In some embodiments, the data is obtained using proteomics techniques such as ELISA, proximity extension assay (PEA), mass spectrometry. In some embodiments, the data is obtained using antibodies that recognize the one or more proteins or polypeptides. Various techniques allow for multiplex analysis of a plurality of proteins or polypeptides in a single sample such as, for example, multiple reaction monitoring (MRM) mass spectrometry, ELISA, proximity extension assay, Western Blot, and protein detection techniques used in the field. In some embodiments, the protein or polypeptide data comprises information for a protein panel. The protein panel can be configured to address specific inquiries such as, for example, having protein biomarkers linked to cardiovascular health for purposes of assessing a heart condition.

In some embodiments, the protein panel comprises a list of proteins such as the ones provided by Olink Proteomics. In some embodiments, the protein panel comprises a cardiometabolic panel. In some embodiments, the protein panel comprises a cell regulation panel. In some embodiments, the protein panel comprises a cardiovascular panel. In some embodiments, the protein panel comprises a development panel. In some embodiments, the protein panel comprises an immune response panel. In some embodiments, the protein panel comprises an immune-oncology panel. In some embodiments, the protein panel comprises an inflammation panel. In some embodiments, the protein panel comprises a metabolism panel. In some embodiments, the protein panel comprises a neurology panel. In some embodiments, the protein panel comprises an oncology panel. In some embodiments, the protein panel comprises an organ damage panel.

In some embodiments, the protein panel comprises a plurality of proteins or polypeptide biomarkers. In some embodiments, the protein panel comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, or more proteins or polypeptides. In some embodiments, the protein panel comprises a shortened or filtered group of proteins or polypeptides. In some embodiments, the protein panel comprises a reduced group of proteins or polypeptides generated by curating an initial group of proteins or polypeptides for targeted properties or associations. For example, an initial group of proteins linked to ALS may be curated to generate a filtered list of proteins that has more robust experimental support for a causative role in ALS. Accordingly, in some embodiments, the protein panel (e.g., a reduced or filtered panel) has no more than 5, 10, 15, 20, 25, 30, 35, 40, 45, 50, 55, 60, 65, 70, 75, 80, 85, 90, 95, 100, 110, 120, 130, 140, 150, 160, 170, 180, 190, or no more than 200 proteins or polypeptides.

Gene Expression Data

Disclosed herein are algorithms, classifiers, or models that generate classifications of individuals based on input data including RNA sequencing and/or expression data. In some embodiments, input data is generated by performing RNA sequencing on a biological sample obtained from a subject. The input data can be generated using any number of available laboratory techniques including reverse transcriptase quantitative PCR (RT-qPCR) and various RNA sequencing technologies. Examples of RNA sequencing include mRNA sequencing, small RNA sequencing, whole RNA sequencing, targeted RNA sequencing, RNA exome targeted sequencing, and single-cell RNA sequencing. Small RNA sequencing targets small RNA molecules such as microRNA. Whole RNA sequencing targets the RNA transcripts in the transcriptome, and includes both coding and noncoding RNA. Targeted RNA sequencing allows for the selecting and sequencing of specific transcripts of interest using targeted enrichment or targeted amplicon. RNA exome capture sequencing enriches for the coding regions of the transcriptome. In some embodiments, the RNA data comprises information for a genetic panel. The genetic panel can be configured to address specific inquiries such as, for example, having genetic biomarkers linked to cardiovascular health for purposes of assessing a heart condition.

In some embodiments, the genetic panel comprises a list of genes or transcripts having some link or association with one or more health conditions or traits. In some embodiments, the genetic panel comprises RNA sequencing information for a plurality of genes or transcripts. In some embodiments, the genetic panel comprises a cardiometabolic panel. In some embodiments, the genetic panel comprises a cell regulation panel. In some embodiments, the genetic panel comprises a cardiovascular panel. In some embodiments, the genetic panel comprises a development panel. In some embodiments, the genetic panel comprises an immune response panel. In some embodiments, the genetic panel comprises an immune-oncology panel. In some embodiments, the genetic panel comprises an inflammation panel. In some embodiments, the genetic panel comprises a metabolism panel. In some embodiments, the genetic panel comprises a neurology panel. In some embodiments, the genetic panel comprises an oncology panel. In some embodiments, the genetic panel comprises an organ damage panel.

In some embodiments, the genetic panel comprises a plurality of genetic biomarkers. In some embodiments, the genetic panel comprises at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, or more genes or transcripts. In some embodiments, the genetic panel comprises a shortened or filtered group of genes or transcripts. In some embodiments, the genetic panel comprises a reduced group of genes generated by curating an initial group of genes or transcripts for targeted properties or associations. For example, an initial group of genes or transcripts linked to ALS may be curated to generate a filtered list of genes or transcripts that has more robust experimental support for a causative role in ALS. Accordingly, in some embodiments, the genetic panel (e.g., a reduced or filtered panel) has no more than 5, 10, 15, 20, 25, 30, 35, 40, 45, 50, 55, 60, 65, 70, 75, 80, 85, 90, 95, 100, 110, 120, 130, 140, 150, 160, 170, 180, 190, or no more than 200 genes or transcripts.

Feature Selection

Disclosed herein are algorithms, classifiers, or models that generate classifications of individuals based on input data. The algorithms, classifiers, or models incorporate various features such as, for example, one or more biomarkers selected from protein levels, RNA transcript levels, and/or metabolite levels obtained from a biological sample of a subject. The features can be selected through analyzing data obtained for an initial feature set to identify the features that are significantly associated with the biological trait of interest. Using prior knowledge and/or data-driven methods, such features can be selected prior to the application of machine learning algorithms to generate trained models. In some embodiments, features are using certain data transformations such as, for example, principal component analysis.

In some embodiments, an initial feature set is generated by selecting or screening for all biomarkers known to have some association with a particular biological trait or combination of traits. In some embodiments, the initial feature set is generated by mining scientific publications or studies.

For example, loose statistical associations from large-scale screening may generate statistical noise that makes it difficult to identify relevant biomarkers as features for the model. Thus, in some cases, prior knowledge from scientific publications is used to screen for relevant features. As an example, diabetes type 2, ALS, and MS models can be constructed based on publications that identified key biomarkers as indicators of these particular diseases or disorders. In some embodiments, feature selection comprises screening for or identifying features from scientific publications. In some embodiments, feature selection comprises screening for or identifying features from one or more databases. In some embodiments, the one or more databases comprises annotation(s) of one or more biomarkers. In some embodiments, feature selection comprises screening for or identifying features based on annotation(s) from one or more databases.

The annotation(s) can be a gene ontology of a particular biomarker such as an RNA transcript or a gene. The annotation or gene ontology for a biomarker can provide information about its function or relationship with other markers. As an example, the Gene Ontology (GO) resource provides a comprehensive knowledge base on genes and their products. In some embodiments, the gene ontology is represented as a keyword(s) or an identifier (a number, letter, or other unique combination of characters). The gene ontology can refer to a cellular component such as the parts of the cell or its extracellular environment associated with the biomarker. Illustrative and non-limiting examples of cellular components include cell junction, chromatin, membrane, organelle, or other component of the cell. In some embodiments, the gene ontology refers to a molecular function, which refers to the activities of the biomarker at the molecular level such as, for example, a chemical reaction catalyzed by the enzyme protein product of a gene or a binding activity of a transcription factor. Illustrative and non-limiting examples of molecular functions include antioxidant activity, protein folding chaperone, transcription regulator activity, and various other functions. In some embodiments, the gene ontology refers to a biological process, which refers to a set or sequence of one or more molecular activities that together play some role in the functioning of a living organism or component thereof. Illustrative and non-limiting examples of biological processes include actin filament polymerization, detoxification, hematopoiesis, phosphorus utilization, signaling, and various other processes. The annotation or gene ontology can be tiered or structured to provide more general information and/or more detailed information. For example, some biomarkers may be annotated with a cellular component gene ontology tag for cell junction, but a subset of these biomarkers may be further tagged with adherens junction while other biomarkers are instead tagged with desmosome depending on the specific cellular structure these individual biomarkers are associated with.

In some embodiments, the annotation for a biomarker is obtained from a database comprising biological pathway information. The database can include pathway maps of the relationships between genes or gene products and other biological molecules such as, for example, metabolites. As an example, the KEGG pathway database provides biological pathways that model molecular interactions between biological components. The pathway maps can include various types of information for biomarkers including genes, proteins, RNAs, chemical compounds, glycans, and chemical reactions. In some embodiments, additional information such as mutations associated with diseases and drug targets are included. In some embodiments, the pathway maps are classified into the sub-sections such as metabolism, genetic information processing (e.g., transcription, translation, replication, etc.), environmental information processing (e.g., signal transduction), cellular processes (e.g., cell proliferation), organismal systems (e.g., immune system), human diseases, and drug development.

In some embodiments, the systems, methods, and software disclosed herein utilize an automated or semi-automated feature selection process by which features are selected based on third party annotations such as gene ontology tags. In some embodiments, the features are at least partially selected or screened based on one or more annotations. In some embodiments, the biomarker(s) are annotated or associated with a gene ontology based on one or more tags or labels. These tags or labels can be standardized and formatted to facilitate automated or semi-automated analysis such as, for example, extraction and/or processing. In some embodiments, one or more biomarkers are extracted from a third party database based on one or more annotations. In some embodiments, the biomarkers are further processed or selected based on scientific publications to arrive at an initial feature set. This feature set can be trained using labeled data by a machine learning algorithm to generate a model and/or select for the most significantly associated features for a disease, disorder, or condition, or other trait. In some embodiments, feature selection comprises screening for biomarkers based on KEGG and/or GO annotations.

In some embodiments, the systems, methods, and software disclosed herein comprise a feature selection or feature transformation process. A goal of feature selection is to reduce the size of the feature set while retaining as much useful information as possible. In some embodiments, feature selection comprises filtering out or removing features based on variance. Such techniques include principal component analysis (PCA), partial least squares (PLS) regression, and independent component analysis (ICA).

Non-Molecular Data

Although various algorithms described herein utilize molecular information such as metabolite data to generate classifications of individuals, non-assayed information can also be used. The combination of molecular data and non-molecular data can be useful in enhancing classifier performance. For example, age and sex can serve as important discriminatory features for accurately classifying an individual. Non-molecular data can include patient information such as demographic information. In some cases, classifiers or machine learning models utilize data comprising non-molecular data such as, for example, age or age range, race, ethnicity, nationality, sex, smoking status, weight, body mass index (BMI), exercise (e.g., frequency, duration, and/or intensity), hobbies, household income, geographic location, disabilities, education, employment status, health status (e.g. a confirmed cancer diagnosis), children, marital status, or any combination thereof.

Non-molecular data can include measurable health parameters. Examples of health parameters include heart rate, blood pressure, body temperature, body fat percentage, height, waistline, VO2 max, and other relevant parameters.

Traits

Disclosed herein are algorithms, classifiers, or models that generate classifications or predictions pertaining to one or more traits. Traits are non-molecular information about a subject that can be related to the subject's general well-being or health status. In some embodiments, traits are not directed to a particular disease or disease spectrum. Examples of traits include non-molecular data such as age, sex, body mass index (BMI), race, ethnicity, personality traits, family history, and other measurable health parameters or demographics. Traits can be selected from or organized into various categories including personal characteristics, general health, mental health, health behaviors, interventions (e.g., treatments and therapies), systems (e.g., organ systems), environmental (e.g., work environment), conditions (e.g., diagnostic history), and other categories related to general health and well-being. In some embodiments, the algorithms, classifiers, or models disclosed herein are trained on data pertaining to one or more traits.

Accordingly, in some embodiments, predictions are generated for individuals that provide an assessment (e.g., a regression score) of one or more traits. In some embodiments, the prediction is an assessment of a composite well-being for an individual that incorporates multiple traits. In some embodiments, the prediction incorporates information about one or more traits to provide an assessment of one or more other traits. As an example, trait information or data for sleep, diet, and sun exposure may be included in a data set along with the "thrive" trait (e.g., a general assessment of health and well-being) that is used to train a model to predict a "thrive" assessment or score based at least in part on the trait information. In some embodiments, the model is trained to assess one or more traits using molecular data and/or trait information. As an example, a model can be trained to incorporate protein levels and RNA sequencing data in providing an assessment of an individual for a particular trait such as anxiety.

Alternatively, in some embodiments, predictions or classifications of a disease, disorder, or condition is generated based on input data incorporating trait information. In some embodiments, the systems, methods, and software disclosed herein identify certain traits that are significantly associated with or predictive of some mental health conditions such as depression. As an illustrative example, trait information for fitness and sleep may be identified as being associated with depression. Trait information and other data types such as molecular data can be combined as features in a single model or multiple models. In some embodiments, the model(s) undergoes machine learning using training data that incorporates trait information and/or molecular data such as RNA sequencing data and/or protein quantification. As a result, predictions can be generated that provide an assessment or evaluation of one or more traits and/or one or more diseases, disorders, or conditions. As an example, certain trait information may be associated with a particular disease or disorder that the subject is unaware of such as ALS.

In some embodiments, the systems, methods, and software disclosed herein incorporate input data including molecular data to generate predictions or evaluations of one or more traits. As an illustrative example, a model or algorithm undergoes machine learning using training data that includes metabolite data for individuals along with trait information relating to smoking, past smoking, alcohol load, amount of sleep, hours awake, or acute infection(s). Accordingly, certain metabolite levels can be identified as relevant to certain traits which can, for example, provide a metabolite signature for smokers. In some embodiments, the trait-related predictions or evaluations provided by the algorithms, models, or classifiers disclosed herein comprise a regression (e.g., a numerical or continuous output) instead of a classification (e.g., a categorical output such as yes/no).

In some embodiments, the systems, methods, and software disclosed herein incorporate input data such as patient-generated health data alone or in combination with other types of data (e.g., molecular data). In some embodiments, training data pertaining to one or more traits include a subject's self-assessment of a trait such as responses to questions. Trait information can include patient-generated health data. In some cases, trait information comprises yes/no responses to questions. In some cases, trait information comprises a response that is a number or score (e.g., an acute pain self-assessment from 1 to 10 with 10 being the highest possible level of pain). Examples of trait categories, traits, questions, and responses are provided in Table 3.

TABLE 3

| | | Traits | |
|---|---|---|---|
| Category | Trait | Question | Score |
| Personal characteristics | Sex | | F/M |
| | Age | | Chronological age |
| | BMI | weight at day of draw; height | weight (in kilograms) over your height squared (in centimeters) |
| | Race | | |
| | Ethnicity | | |
| | Personality traits | | |
| General Health | Family history | | |
| | Current conditions (not including acute conditions) | Reported conditions | |
| | Acute infection | Do you have any infections right now (that you know of)? (B) What kind of respiratory infection do you have (or think you have)? (B) What kind of gastrointestinal infection do you have (or think you have)? (B) | by the conditions |

TABLE 3-continued

| Category | Trait | | Question | Score |
|---|---|---|---|---|
| | Allergies | | | |
| | Perceived health | Overall perceived health | Over the last month, how has your health has been (B) | 5 levels |
| | | Impact of condition | Over the last month, how much has your <condition> affected your life? (B) | |
| | | Health change | Over the last month, how has your health changed? (B) | |
| | Circadian cycle | | How long ago did you wake up for the day (and not go back to sleep again?) (B) | |
| | | | How much sleep did you get last night? (B) | |
| | Menstrual cycle | | Which of the following best describes your menstruation? When did your last menstrual period start? (B) | Exclude I do have menstrual periods because of birth control OR I am past menopause, or I have had artificially-induced menopause OR This question doesn't apply to me |
| | Genetic predisposition | | | |
| | Thrive | Thrive ability | Over the last month, how well could you think, concentrate, and remember things? (B) | |
| | | | Over the last month, how well could you control your emotions? | |
| | | | Over the last month, how well could you take care of your personal needs? | |
| | | | Over the last month, how well could you meet your responsibilities at work, school or home? | |
| | | | Over the last month, how well could you participate in your favorite social and leisure activities? | |
| | | Thrive core symptoms | Please rate the severity of any pain over the past month | |
| | | | Please rate the severity of any depressed mood over the past month | |
| | | | Please rate the severity of any anxious mood over the past month | |
| | | | Please rate the severity of any fatigue over the past month | |
| | | | Please rate the severity of any stress over the past month | |
| | | Thrive mobility | Over the last month, how well could you walk without support? | |
| | | | Over the last month, how well could you climb stairs? | |
| | | Thriving experience | Over the last month, how often did you feel good about yourself? | |
| | | | Over the last month, how often did you find meaning in your life? | |
| | | | Over the last month, how often did you feel connected to others? | |
| | | | Over the last month, how often did you feel able to live the life your wanted | |

TABLE 3-continued

| Category | Trait | | Question | Score |
|---|---|---|---|---|
| Mental Health | Cognition | | over the last month, how well could you think, concentrate, and remember things? (B) | 5 levels |
| | Energy | | | |
| | Depression | | Please rare the severity of any depressive mood over the past month | |
| | Anxiety | | Please rate the severity of any anxious mood over the past month | |
| | Stress | | Please rate the severity of any stress over the past month | |
| | Coping ability (mental resilience) | stress, anxiety, depression, control emotions | Please rate the severity of any stress over the past month<br>Please rate the severity of any anxious mood over the past month<br>Please rate the severity of any anxious mood over the past month<br>Over the last month, how well could you control your emotions? | |
| | Feel good/bad | pain and fatigue | Please rate the severity of any fatigue over the past month<br>Please rate the severity of any pain over the past month | |
| Health behaviors | Fitness | | Over the last month, how well could you lift heavy things? (A)<br>Over the last month, for how long could you do exercise that made you breathe hard? (A) | Not at all = 0<br>Poorly = 1<br>fairly well = 2<br>very well = 3<br>extremely well = 4 |
| | Substances | Smoke now (are you on nicotine now) | Some common substances can affect what appears in your blood. Which of these have you used in the last 24 hours? (B)<br>How long ago did you last take nicotine other than tobacco? (B)<br>How long ago did you last take tobacco? (B) | yes to Tobacco less than 24 h less than 24 h |
| | | Past smoking | Do you smoke? (A)<br>Did you ever smoke cigarettes regularly (at least one cigarette per day)? (A)<br>Did you ever smoke at least one pack of cigarettes a day? (A) | No, but I used to OR No I never smoked AND<br>Yes OR yes |
| | | Past heavy Smoking now | Do you smoke? (A)<br>Did you ever smoke cigarettes regularly (at least one cigarette per day)? (A)<br>Did you ever smoke at least one pack of cigarettes a day? (A) | No, but I used to OR No I never smoked AND group smoke regularly AND at least one pack Vs no smoked regularly AND no to one pack a day |
| | | Alcohol Load | Some common substances can affect what appears in your blood. Which of these have you used in the last 24 hours? (B)<br>How long ago did you have alcohol? (B)<br>How many drinks did you have? (B) | no to alcohol Exclude less than 24 h |
| | | Recreational drug now | Some common substances can affect what appears in your blood. Which of these have you used in the last 24 hours? (B) | yes to Drugs not listed in my profile as treatment |
| | | Recreational drug past | Some common substances can affect what appears in your blood. Which of these have you used in the last 24 hours? (B)<br>Do you use any of these "recreational" drugs to manage your disease? Please select all that apply (B) | Exclude Drugs in the last 24 h yes to use any of these to manage disease |

TABLE 3-continued

| Category | Trait | | Question | Score |
|---|---|---|---|---|
| | | Caffeine load (time since caffeine) | How long ago did you have caffeine? (B) | hours |
| | Sleep | Sleep load last night | How much sleep did you get last night? (B) | hours |
| | | Sleep quality | Over the last month, how well could you fall asleep when you wanted to? (B) Over the last month, how well could you sleep through the night? (B) Last night, how well could you fall asleep when you wanted to? (B) Last night, how well could you sleep through the night? (B) | |
| | Diet | Diet quality | Over the last month, how healthy was your overall diet? (B) | |
| | | Food load (time since food) | When did you last eat or drink anything (other than water)? (B) | hours |
| | | Intervention | Fasting, vegan, paleo | |
| | Sun exposure | Sun exposure load | Over the last week, about how many hours did you spend outdoors, in direct sunlight? | hours |
| | Sex drive | | | |
| Interventions | Vaccines | | Have you had any vaccines in the past three months? Please select all that apply (B) | |
| | Treatment | Treatment "Special" Prescriptions drugs | We encourage you to share treatments on your profile. If you are taking any prescription drugs to manage your disease but are NOT comfortable showing them in your profile, please select them: (B) | |
| | Procedures | | | |
| | Supplement | | | |
| Systems | Circulatory | | | |
| | Dental | | | |
| | Digestive | | | |
| | Endocrine | | | |
| | Lymph/Immune | | | |
| | Metabolism | | | sugar, insulin, glucagon, IR, . . . |
| | Musculoskeletal | | | |
| | Nervous (including brain) | | | |
| | Renal | | | |
| | Reproductive (history and current) | | | including: pregnancy duration, breastfeeding, pre x post menopause, pre menopausal: with menstrual periods x without) |
| | Respiratory | | | |
| | Skin | | | |
| Environmental | Life events including trauma | | | |
| | Living environment | | | |
| | Work | | | |
| | Chemical exposures | | | |
| | Social functioning | | | |

TABLE 3-continued

| Category | Trait | | Question | Score |
|---|---|---|---|---|
| Conditions | Diagnostic history | Diagnosed by HCP | When were you diagnosed with <condition> by a healthcare provider? | e.g., onset of symptoms, diagnosis date, second opinions |
| | | Diagnosis prediction | | |
| | | Onset of symptoms | | |
| | | Diagnosed date | | |
| | | Second opinion | | |
| | | Diagnostic labs and tests | | |
| | | Diagnosis confidence index | | |
| | | PRO score | | |
| | Disease severity | Severity index | | |
| | Symptoms and Signs | | | |
| | Potential complications and comorbidities | | | |
| | Monitoring labs and tests | | | |
| | Treatment (current and history) | | | |

Metabolite Detection Techniques

Metabolites in a specimen can be determined using various molecular detection techniques such as mass spectrometry, nuclear magnetic resonance, chromatography, or other methods. Oftentimes, mass spectrometry is used in combination with a chromatography technique in order to separate metabolites of interest prior to mass spectrometry analysis in order to provide enhanced sensitivity of detection and/or quantitation of metabolites in complex samples. For example, high performance liquid chromatography (HPLC), gas chromatography (GC), and capillary electrophoresis (CE) may be coupled to mass spectrometric analysis to evaluate metabolites in a biological sample.

A cohort sample set can be processed in sample groups with subject samples and pooled plasma samples for QC/normalization purposes. Each sample group is then analyzed on the LC-MS platform shortly after processing, for example the day following the completion of sample processing. Consistent with the specification, alternative numbers of subject and normalization samples are employed in certain examples.

In some cases, LC-MS data from each sample is collected on an appropriate instrument with an appropriate ionization source, for example a quadrupole time-of-flight (Q-TOF) mass spectrometer coupled to ultra-high performance liquid chromatography (UHPLC) instrument, with an electrospray ionization (ESI) source. LC flow rates can be optimized based on sample conditions and pressures.

The biological sample can be assessed by analysis of a number of injections from a single pooled source. For example, a collection of blood samples is assessed by LC-MS using multiple injections from a single pooled source. Data is collected in MS1/MS2 mode so that feature identifications can be made concurrently with the quantitative MSI data. Tandem mass spectrometry data is collected via a second fragmentation method, such as collision induced dissociation (CID), in which an MSI survey scan is followed by fragmentation of other precursor ions, such as the three most abundant precursor ions.

Algorithms

Disclosed herein are algorithms for analyzing input data for one or more biomarkers to generate output relating to differential classifications or associations such as the presence or likelihood of a disease, disorder, or condition or trait. In some embodiments, the input data comprises one or more data types such as metabolite data, genetic data, protein data, or any combination thereof. Analyses of input data such as metabolite data, and the differential classifications derived therefrom are typically performed using various algorithms and programs. The levels of individual metabolites can make up a metabolite pattern, signature, or profile that corresponds to a particular individual. The machine learning algorithms described herein can generate classifications that account for the complex interrelationships between different metabolites and the pathways that impact those metabolites. Metabolite signatures can provide insight into the health status and/or therapeutic options for the individual. In some embodiments, non-metabolite data such as gene expression data and/or protein quantification data is analyzed alone or in combination with each or with metabolite data using any of the algorithms or methods described herein. Accordingly, genetic signatures and/or protein signatures can also provide insight into the health status or other traits for the individual. In some cases, the algorithms disclosed herein allow for detection, evaluation, assessment, and/or diagnosis of two or more diseases, disorders, or conditions or traits. The two or more diseases, disorders, or conditions or traits may be related, for example, falling within a common category such as autoimmune disorder or immune-related disorder. In some cases, diseases, disorders, or conditions or traits are related if they share one or more common features that are predictive of their status such as in the case of overlapping feature sets of biomarker panels.

Metabolites displaying differential signaling patterns, i.e., discriminating metabolites, between samples obtained from reference subjects (e.g., healthy subjects or subjects with a different disease) can be identified using known statistical tests such as a Student's T-test or ANOVA. The statistical analyses can be applied to select the discriminating metabolites that distinguish the different conditions at predetermined stringency levels. In some cases, metabolites are evaluated for feature importance within one or more models such as shown in FIG. 15B. In some embodiments, a list of the most discriminating metabolites can be obtained by ranking the metabolites by statistical means such as their feature importance. For example, discriminating metabolites can be ranked and identified as having feature importance of between zero and one hundred. In some instances, the cutoff feature importance value for determining the discriminating metabolite can be adjusted to at least 1, 5, 10, 20, 30, 40, 50, 60, 70, 80, 90, or 95 (out of 100) for one or more models. Such statistical tests disclosed herein can also be applied to non-metabolite features such as genes and proteins that provide differential patterns between cohorts of subjects such as healthy and sick cohorts.

In some cases, a metabolite biomarker panel as used herein comprises at least 1, 2, 3, 4, 5, 6, 7, 8, 9, 10, 11, 12, 13, 14, 15, 16, 17, 18, 19, 20, 21, 22, 23, or 24 of the metabolites listed in FIG. 15A. In some cases, a metabolite biomarker panel as used herein comprises no more than 1, 2, 3, 4, 5, 6, 7, 8, 9, 10, 11, 12, 13, 14, 15, 16, 17, 18, 19, 20, 21, 22, 23, or 24 of the metabolites listed in FIG. 15A. In some cases, a metabolite biomarker panel as used herein comprises at least 1, 2, 3, 4, 5, 6, 7, 8, 9, 10, 11, 12, 13, 14, 15, 16, 17, 18, 19, 20, 21, 22, 23, 24, 25, or 26 of the metabolites listed in FIG. 17A. In some cases, a metabolite biomarker panel as used herein comprises no more than 1, 2, 3, 4, 5, 6, 7, 8, 9, 10, 11, 12, 13, 14, 15, 16, 17, 18, 19, 20, 21, 22, 23, 24, 25, or 26 of the metabolites listed in FIG. 17A. The biomarker panel may be suitable for classifying or evaluating multiple sclerosis (MS) and/or a related or similar disease, disorder, or condition.

In some cases, a metabolite biomarker panel as used herein comprises at least 1, 2, 3, 4, 5, 6, 7, 8, 9, 10, 11, 12, 13, 14, 15, 16, 17, 18, 19, 20, 21, 22, 23, 24, or 25 of the metabolites listed in FIG. 22A. In some cases, a metabolite biomarker panel as used herein comprises no more than 1, 2, 3, 4, 5, 6, 7, 8, 9, 10, 11, 12, 13, 14, 15, 16, 17, 18, 19, 20, 21, 22, 23, 24, or 25 of the metabolites listed in FIG. 22A. In some cases, a metabolite biomarker panel as used herein comprises at least 1, 2, 3, 4, 5, 6, 7, 8, 9, 10, 11, 12, 13, 14, 15, 16, 17, 18, 19, or 20 of the metabolites listed in FIG. 24A. In some cases, a metabolite biomarker panel as used herein comprises no more than 1, 2, 3, 4, 5, 6, 7, 8, 9, 10, 11, 12, 13, 14, 15, 16, 17, 18, 19, or 20 of the metabolites listed in FIG. 24A. The biomarker panel may be suitable for classifying or evaluating amyotrophic lateral sclerosis (ALS) and/or a related or similar disease, disorder, or condition.

In some cases, a metabolite biomarker panel as used herein comprises at least 1, 2, 3, 4, 5, 6, 7, 8, 9, 10, 11, 12, 13, 14, 15, 16, 17, 18, 19, or 20 of the metabolites listed in FIG. 27A. In some cases, a metabolite biomarker panel as used herein comprises no more than 1, 2, 3, 4, 5, 6, 7, 8, 9, 10, 11, 12, 13, 14, 15, 16, 17, 18, 19, or 20 of the metabolites listed in FIG. 27A. In some cases, a metabolite biomarker panel as used herein comprises at least 1, 2, 3, 4, 5, 6, 7, 8, 9, 10, 11, 12, 13, 14, 15, 16, 17, 18, 19, 20, 21, 22, 23, or 24 of the metabolites listed in FIG. 29A. In some cases, a metabolite biomarker panel as used herein comprises no more than 1, 2, 3, 4, 5, 6, 7, 8, 9, 10, 11, 12, 13, 14, 15, 16, 17, 18, 19, 20, 21, 22, 23, or 24 of the metabolites listed in FIG. 29A. The biomarker panel may be suitable for classifying or evaluating systemic lupus erythematosus (SLE) and/or a related or similar disease, disorder, or condition.

In some instances, the systems, media, and methods disclosed herein apply machine learning models or algorithms that use one or more biomarker panels to identify, classify, evaluate, or differentiate between related diseases, disorders, or conditions. Related diseases, disorders, or conditions can include autoimmune or immune-related diseases, disorders, or conditions. In some cases, the systems, media, and methods disclosed herein comprise monitoring or evaluating biomarkers such as metabolites for an individual over time (optionally with or without treatment) and generating a recommendation for a treatment.

In some cases, information of the discriminating metabolites selected can be subsequently imported into a machine learning algorithm to obtain a statistical or mathematical model (e.g., a classifier) that classifies the metabolic data with accuracy, sensitivity, and/or specificity. Any one of the many computational algorithms can be utilized for the classification purposes. Likewise, information for discriminating genes or proteins can also be imported into a machine learning algorithm to generate a model that classifies data or generates a risk prediction based on the data including metabolic data, gene expression data, protein quantification data, or any combination thereof.

The classifiers can be rule-based or machine learning algorithms. The machine learning classification algorithms can be supervised or unsupervised. A basic classification algorithm, Linear Discriminant Analysis (LDA) may be used in analyzing biomedical data in order to classify two or more disease classes. LDA can be, for example, a classification algorithm. A more complex classification method, Support Vector Machines (SVM), uses mathematical kernels to project the original predictors to higher-dimensional spaces, then identifies the hyperplane that optimally separates the samples according to their class. Some common kernels include linear, polynomial, sigmoid or radial basis functions. Other algorithms for data analysis and predictive modeling based on metabolite data can include but are not limited to Naive Bayes Classifiers, Logistic Regression, Quadratic Discriminant Analysis, K-Nearest Neighbors (KNN), K Star, Attribute Selected Classifier (ACS), Classification via clustering, Classification via Regression, Hyper Pipes, Voting Feature Interval Classifier, Decision Trees, Random Forest, and Neural Networks, including Deep Learning approaches.

In some embodiments, a machine learning algorithm (or software module) of a platform or system as described herein utilizes one or more neural networks. A neural network is a type of computational system that can learn the relationships between an input data set and a target data set. A neural network is a software representation of a human neural system (e.g., cognitive system), intended to capture "learning" and "generalization" abilities as used by a human. In some embodiments machine learning algorithm (or software module), the machine learning algorithm (or software module) comprises a neural network comprising a convolutional neural network. Non-limiting examples of structural components of embodiments of the machine learning software described herein include: convolutional neural networks, recurrent neural networks, dilated convolutional neural networks, fully connected neural networks, deep generative models, and Boltzmann machines.

In some embodiments, a neural network is comprised of a series of layers termed "neurons." In some embodiments, a neural networks comprises an input layer, to which data is presented; one or more internal, and/or "hidden," layers; and an output layer. A neuron may be connected to neurons in other layers via connections that have weights, which are parameters that control the strength of the connection. The number of neurons in each layer may be related to the complexity of the problem to be solved. The minimum number of neurons required in a layer may be determined by the problem complexity, and the maximum number may be limited by the ability of the neural network to generalize. The input neurons may receive data from data being presented and then transmit that data to the first hidden layer through connections' weights, which are modified during training. The first hidden layer may process the data and transmit its result to the next layer through a second set of weighted connections. Each subsequent layer may "pool" the results from the previous layers into more complex relationships. In addition, whereas conventional software programs require writing specific instructions to perform a function, neural networks are programmed by training them with a known sample set and allowing them to modify themselves during (and after) training so as to provide a desired output such as an output value. After training, when a neural network is presented with new input data, it is configured to generalize what was "learned" during training and apply what was learned from training to the new previously unseen input data in order to generate an output associated with that input.

In some embodiments, metabolite profiles are obtained from a training set of samples, which are used to identify the most discriminative combination of metabolites. In some cases, the most discriminative combination of metabolites is identified by applying an elimination algorithm based on SVM analysis. The accuracy of the algorithm using various numbers of input metabolites ranked by level of statistical significance can be determined by cross-validation. To generate and evaluate metabolite profiles of a feasible number of discriminating metabolites, multiple models can be built using a plurality of discriminating metabolites to identify the best performing model(s). In some cases, an Ensemble model is generated that incorporates a plurality of models. The Ensemble model can provide classification of samples that is subject to less variation than individual models or classifiers that are incorporated into the Ensemble model.

In some instances, specific metabolite(s) are excluded from inclusion in the training and/or testing of machine learning algorithms. Metabolites can be excluded based on certain rules designed to reduce sample-to-sample variation. For example, certain metabolites undergo significant variation over time and may correspond to certain activities such as, for example, consumption of food or liquids, physical activity, sleep, or other factors. Accordingly, failure to account for these factors can result in considerable variation of corresponding metabolites that consequently reduce the predictive performance of classifiers trained using data for these metabolites. Thus, in some cases, the methods described herein comprise removing or excluding one or more metabolites from inclusion in the classifier(s) in order to enhance predictive performance. In some embodiments, a feature list or panel of features (e.g., biomarkers) comprises at least 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 10000, 20000, 30000, 40000, or 50000 metabolites and/or no more than 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 10000, 20000, 30000, 40000, or 50000 metabolites that are used in a specific machine learning algorithm or classifier.

Multiple models comprising different numbers of discriminating metabolites can be generated, and the performance of each model can be evaluated by a cross-validation process. An SVM classifier can be trained and cross-validated by assigning each sample of a training set of samples to one of a plurality of cross-validation groups. For example, for a five-fold cross-validation, each sample is assigned to one of four cross-validation groups such that each group comprises test and control or reference samples. One of the cross-validation groups is held-out, and a classifier model is trained using the samples in the remaining groups 2-4. Metabolites that discriminate test cases and reference samples in the training group can be analyzed and ranked, for example by statistical p-value. The top k metabolites can be used as predictors for the model. To evaluate the relationship between the number of input predictors and model performance, and to guard against overfitting, the sub-loop is repeated for a range of k such as 10, 25, 50 top metabolites or more. Predictions or classification of samples in group 1 are made using the model generated using groups 2-4. Models for each of the four groups are generated, and the performance (AUC, sensitivity and/or specificity) can be calculated using all the predictions from the 4 models using data from true disease samples. The cross-validation steps can be repeated at least 100 times, and the average performance is calculated relative to a confidence interval such as, for example, 95%.

Alternatively, unsupervised learning can be used to train a classifier or model without using labeled cases or samples. A common example of unsupervised training entails cluster analysis. Non-limiting examples of clustering algorithms include hierarchical clustering, k-means clustering, Gaussian mixture models, and Hidden Markov models.

In some cases, a plurality of machine learning algorithms are utilized to generate a final Ensemble model. The plurality of machine learning algorithms can comprise two or more of: Generalized Linear Model (glmnet), Random Forests (if), Partial Least Squares (pls), Extreme Gradient Boosting (xgbDART), Support Vector Machines with Linear Basis Function Kernel (svmLinear), Support Vector Machines with Radial Basis Function Kernel (svmRadial), or Neural Networks (nnet). Two or more of these 7 algorithms can be run with various different random seed train/test splits.

The classifier used to generate predictions includes one or more selected feature spaces such as metabolite, gene expression, protein quantity, or any combination thereof. The values for these features obtained from a sample can be fed into the classifier or trained algorithm to generate one or more predictions. In some cases, the methods disclosed herein select for the variables that are of predictive value, for example, by culling the features to generate a feature subset used for generating predictions in the final classifier or model. Methods that reduce the number of variables or features can be selected from a non-limiting group of algorithms including principal component analysis (PCA), partial least squares (PLS) regression, and independent component analysis (ICA). In some cases, the methods disclosed herein analyze numerous variables directly and are selected from a non-limiting group of algorithms including methods based on machine learning processes. Machine learning processes can include random forest algorithms, bagging techniques, boosting methods, or any combination thereof. Methods may be statistical methods. Statistical methods can include penalized logistic regression, prediction analysis of microarrays, methods based on shrunken centroids, support vector machine analysis, or regularized linear discriminant analysis.

A feature space can comprise a panel of metabolites, genes, proteins, or any combination thereof within a sample. In some cases, the classifier or trained algorithm comprises a metabolite panel comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 20, at least 25, at least 30, at least 35, at least 40, at least 45, or at least 50 or more metabolites (e.g., metabolite levels). In some cases, the classifier or trained algorithm comprises a genetic panel comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 20, at least 25, at least 30, at least 35, at least 40, at least 45, or at least 50 or more genes (e.g., gene expression levels). In some cases, the classifier or trained algorithm comprises a protein panel comprising at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 20, at least 25, at least 30, at least 35, at least 40, at least 45, or at least 50 or more proteins (e.g., protein levels).

An optimal model/classifier based on metabolite data can be selected and used to classify a test set. The performance of different classifiers is determined using a validation set and/or using a test set of samples. Accordingly, performance characteristics such as accuracy, sensitivity, specificity, and Area Under the Curve (AUC) of the Receiver Operating Characteristic (AUC) curve can be obtained from a given model. In some embodiments, different sets of discriminating metabolites are identified to distinguish different diseases, disorders, or conditions. Accordingly, an optimal model/classifier based on a set of the most discriminating input metabolites is established for each of the diseases, disorders, or conditions to provide a differential diagnosis.

In some instances, a plurality of models is combined or consolidated into an Ensemble classifier or model. The plurality of models can include two, three, four, five, six, seven, or more models. In some cases, the Ensemble model is an average of the plurality of models. One challenge that can arise in the classification of a particular disease, disorder, or condition is that some such diseases, disorders, or conditions are closely related and may share one or more common features used to train the classifier or model. For example, FIG. 13A shows the AUC curve for multiple sclerosis, and the model generates false positive multiple sclerosis calls that misclassify a substantial number of amyotrophic lupus erythematosus positive cases (i.e., ALS positive cases are mistaken for MS positive cases by the MS classifier). Thus, a classification approach that incorporates both MS and ALS models may be able to more accurately detect MS and ALS, respectively, than individual models alone. For example, application of a single model for detection of a single disease, disorder or condition may provide a positive or negative assessment as to the presence of the disease, disorder, or condition, but a patient who has a related but different disorder may be identified as a false positive since the model is not configured to account for this scenario. By applying multiple models directed to related diseases, disorders, or conditions, a false positive for one disorder may be converted into a true positive for another disorder. This information can be used to facilitate downstream steps such as further testing to confirm the identified disorder and/or to provide treatment. Accordingly, in some aspects, the methods described herein incorporate a plurality of models configured to generate a plurality of related classifications. The plurality of related classifications can include MS, ALS, SLE, or any combination thereof. In some cases, the plurality of related classifications include neurodegenerative diseases. The plurality of related classifications can comprise classifications that share one or more discriminating metabolites (e.g., model features) such as, for example, at least 1, 2, 3, 4, 5, 6, 7, 8, 9, 10, 15, 20, 25, 30, 35, 40, 45, 50, 55, 60, 65, 70, 75, 80, 85, 90, 95, or 100 metabolites.

Systems for Classifying an Individual

In some aspects, a system as described herein is configured to generate a classification of an individual relative to one or more related classifications. The system as described herein can comprise a network element for communicating with a server. Sometimes, the system comprises a server. The system can be configured to upload to and/or download data from the server. In some cases, the server is configured to store metabolite data and/or other information for the subject. The server can be configured to store historical data (e.g., past metabolite data) for the subject. In some instances, the server is configured to backup data from the system. In certain cases, the system is configured to perform any of the methods described herein.

In some aspects, a system as described herein is configured to generate a classification of an individual for one or more diseases, disorders, or conditions. The system can comprise a network element communicating with a server on a network and a device, the device comprising: a processor; and a non-transitory computer-readable medium including instructions executable by the processor and configured to cause the processor to: (a) receiving data relating to a specimen taken from the individual; (b) providing the data as input to one or more machine learning algorithms; and (c) generating, using the one or more machine learning algorithms, a classification of the individual relative to a plurality of related classifications based on the data.

In some cases, the system is configured to encrypt data. In some embodiments, data on the server is encrypted. The system or apparatus can comprise a data storage unit or memory for storing data. In certain instances, data encryption is carried out using Advanced Encryption Standard (AES). Data encryption is often carried out using 128-bit or 256-bit AES encryption. Data encryption can include full-disk encryption of the data storage unit. In some instances, data encryption comprises virtual disk encryption (e.g., encrypting a folder containing sensor data files for a subject). In various aspects, data encryption comprises file encryption (e.g., encrypting sensor data files for an individual). Sometimes, data that is transmitted or otherwise communicated between the system or apparatus and other devices or servers is encrypted during transit. Wireless communications between the system and other devices or servers can be encrypted. Data in transit can be encrypted using a Secure Sockets Layer (SSL).

A system as described herein can comprise a digital processing device that includes one or more hardware central processing units (CPUs) or general purpose graphics processing units (GPGPUs) that carry out the device's functions. The digital processing device further comprises an operating system configured to perform executable instructions. The digital processing device is optionally connected to a computer network. The digital processing device is optionally connected to the Internet such that it accesses the World Wide Web. The digital processing device is optionally connected to a cloud computing infrastructure. Suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein.

Typically, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing.

A digital processing device as described herein either includes or is operatively coupled to a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

A system or method as described herein can be used to generate a classification based on data such as metabolite data which may then be used to determine whether an individual has or is at risk of having a disease, disorder, or condition. In addition, in some embodiments, a system or method as described herein generates a database as containing or comprising past and/or present metabolite data and/or classifications.

Some embodiments of the systems described herein are computer based systems. These embodiments include a CPU including a processor and memory which may be in the form of a non-transitory computer-readable storage medium. These system embodiments further include software that is typically stored in memory (such as in the form of a non-transitory computer-readable storage medium) where the software is configured to cause the processor to carry out a function. Software embodiments incorporated into the systems described herein contain one or more modules.

In various embodiments, an apparatus comprises a computing device or component such as a digital processing device. In some of the embodiments described herein, a digital processing device includes a display to send visual information to a user. Non-limiting examples of displays suitable for use with the systems and methods described herein include a liquid crystal display (LCD), a thin film transistor liquid crystal display (TFT-LCD), an organic light emitting diode (OLED) display, an OLED display, an active-matrix OLED (AMOLED) display, or a plasma display.

A digital processing device, in some of the embodiments described herein includes an input device to receive information from a user. Non-limiting examples of input devices suitable for use with the systems and methods described herein include a keyboard, a mouse, trackball, track pad, or stylus. In some embodiments, the input device is a touch screen or a multi-touch screen.

The systems and methods described herein typically include one or more non-transitory computer-readable storage media encoded with a program including instructions executable by the operating system of an optionally networked digital processing device. In some embodiments of the systems and methods described herein, the non-transitory storage medium is a component of a digital processing device that is a component of a system or is utilized in a method. In still further embodiments, a computer-readable storage medium is optionally removable from a digital processing device. In some embodiments, a computer-readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Typically the systems and methods described herein include at least one computer program, or use of the same. A computer program includes a sequence of instructions, executable in the digital processing device's CPU, written to perform a specified task. Computer-readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages. The functionality of the computer-readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Typically, the systems and methods described herein include and/or utilize one or more databases. In view of the disclosure provided herein, those of skill in the art will recognize that many databases are suitable for storage and retrieval of baseline datasets, files, file systems, objects, systems of objects, as well as data structures and other types of information described herein. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

FIG. 32 shows an exemplary embodiment of a system as described herein comprising an apparatus such as a digital processing device 3201. The digital processing device 3201 includes a software application configured to generate a classification of an individual by, for example, analyzing data using a machine learning classifier. The digital processing device 3201 may include a central processing unit (CPU, also "processor" and "computer processor" herein) 3205, which can be a single core or multi-core processor, or a plurality of processors for parallel processing. The digital processing device 3201 also includes either memory or a memory location 3210 (e.g., random-access memory, read-only memory, flash memory), electronic storage unit 3215 (e.g., hard disk), communication interface 3220 (e.g., network adapter, network interface) for communicating with one or more other systems, and peripheral devices, such as cache. The peripheral devices can include storage device(s) or storage medium 3265 which communicate with the rest of the device via a storage interface 3270. The memory 3210, storage unit 3215, interface 3220 and peripheral devices are configured to communicate with the CPU 3205 through a communication bus 3225, such as a motherboard. The digital processing device 3201 can be operatively coupled to a computer network ("network") 3230 with the aid of the communication interface 3220. The network 3230 can comprise the Internet. The network 3230 can be a telecommunication and/or data network.

The digital processing device 3201 includes input device(s) 3245 to receive information from a user, the input device(s) in communication with other elements of the device via an input interface 3250. The digital processing device 3201 can include output device(s) 3255 that communicates to other elements of the device via an output interface 3260.

The CPU 3205 is configured to execute machine-readable instructions embodied in a software application or module. The instructions may be stored in a memory location, such as the memory 3210. The memory 3210 may include various components (e.g., machine readable media) including, but not limited to, a random access memory component (e.g., RAM) (e.g., a static RAM "SRAM", a dynamic RAM "DRAM, etc.), or a read-only component (e.g., ROM). The memory 3210 can also include a basic input/output system (BIOS), including basic routines that help to transfer information between elements within the digital processing device, such as during device start-up, may be stored in the memory 3210.

The storage unit 3215 can be configured to store files, such as patient information, e.g., metabolite data and non-molecular data. The storage unit 3215 can also be used to store operating system, application programs, and the like. Optionally, storage unit 3215 may be removably interfaced with the digital processing device (e.g., via an external port connector (not shown)) and/or via a storage unit interface. Software may reside, completely or partially, within a computer-readable storage medium within or outside of the storage unit 3215. In another example, software may reside, completely or partially, within processor(s) 3205.

Information and data can be displayed to a user through a display 3235. The display is connected to the bus 3225 via an interface 3240, and transport of data between the display other elements of the device 3201 can be controlled via the interface 3240.

Methods as described herein can be implemented by way of machine (e.g., computer processor) executable code stored on an electronic storage location of the digital processing device 3201, such as, for example, on the memory 3210 or electronic storage unit 3215. The machine executable or machine readable code can be provided in the form of a software application or software module. During use, the code can be executed by the processor 3205. In some cases, the code can be retrieved from the storage unit 3215 and stored on the memory 3210 for ready access by the processor 3205. In some situations, the electronic storage unit 3215 can be precluded, and machine-executable instructions are stored on memory 3210.

In some embodiments, a remote device 3202 is configured to communicate with the digital processing device 3201, and may comprise any mobile computing device, non-limiting examples of which include a tablet computer, laptop computer, smartphone, or smartwatch. For example, in some embodiments, the remote device 3202 is a smartphone of the user that is configured to receive information from the digital processing device 3201 of the apparatus or system described herein in which the information can include a summary, classifications or predictions, or other data. In some embodiments, the remote device 3202 is a server on the network configured to send and/or receive data from the system described herein.

Some embodiments of the systems and methods described herein are configured to generate a database containing or comprising patient information such as metabolite data. A database, as described herein, is configured to function as, for example, a lookup table for healthcare providers, other medical industry professionals and/or other end users. In these embodiments of the systems and methods described herein, metabolite data and/or classifications or diagnoses are presented in a database so that a user is able to, for example, identify whether a specific individual is at risk of certain diseases, disorders, or conditions. In some embodiments, the database is stored on a server on the network. In some embodiments the database is stored locally on the apparatus (e.g., the monitor component of the apparatus). In some embodiments, the database is stored locally with data backup provided by a server.

Certain Terminology

As used herein, the terms "patient," "individual," and "subject" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. The term "animal" as used herein comprises human beings and non-human animals. In one embodiment, a "non-human animal" is a mammal, for example a rodent such as rat or a mouse.

As used herein, the term "classify" or "classification" refers to the output of the model or algorithm being a categorical output, for example, positive identification of a disease, disorder, or condition. As used herein, the term "regression" refers to the output of the model or algorithm being a non-categorical output, for example, a number or continuous variable. As classification and regression can both fall under supervised machine learning, a regression output is also contemplated wherever classification is described within the present disclosure. Therefore, disclosure of "a classifier" configured to evaluate the status of a disease, disorder, or condition is to be interpreted as also disclosing a regression model or algorithm.

EXAMPLES

Example 1

In some cases, a plurality of machine learning algorithms are utilized to generate a final Ensemble model. The plurality of machine learning algorithms can comprise two or more of: Generalized Linear Model (glmnet), Random Forests (rf), Partial Least Squares (pls), Extreme Gradient Boosting (xgbDART), Support Vector Machines with Linear Basis Function Kernel (svmLinear), Support Vector Machines with Radial Basis Function Kernel (svmRadial), or Neural Networks (nnet). Two or more of these 7 algorithms can be run with various different random seed train/test splits.

Figure 4:
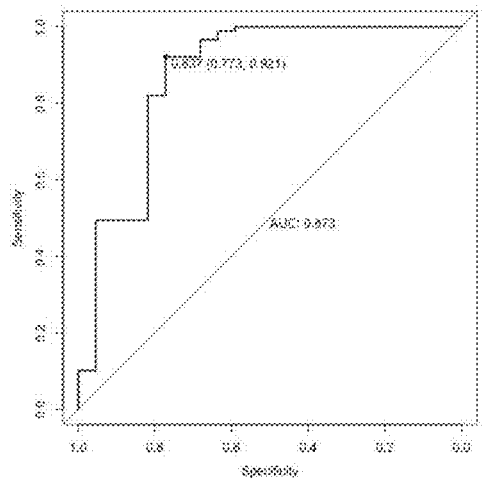
FIG. 4A, FIG. 4B, and FIG. 4C show the AUC curves of the Ensemble classifier trained and tested using for 3 different subpopulations of participant data for amyotrophic lateral sclerosis.
FIG. 4D shows a model summary that averages the individual Ensembles from FIGS. 4A-4C.
Figure 4A:
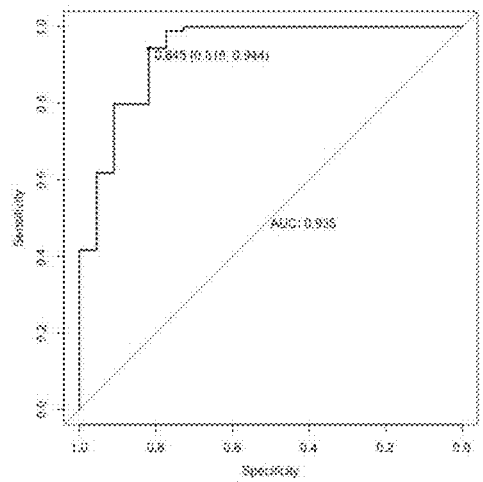
Figure 4B:
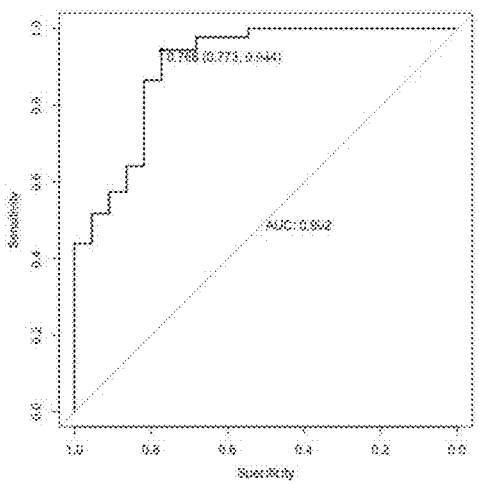
Figure 4C:
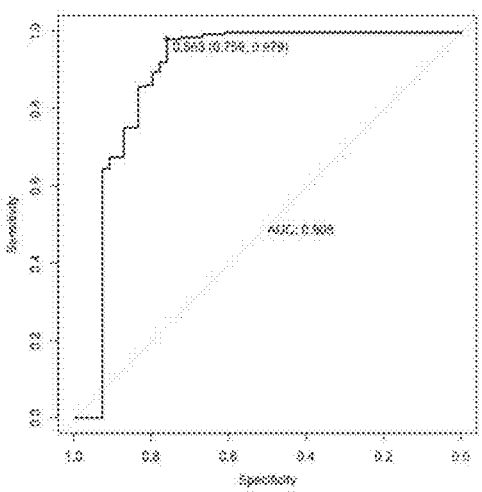
Figure 21:
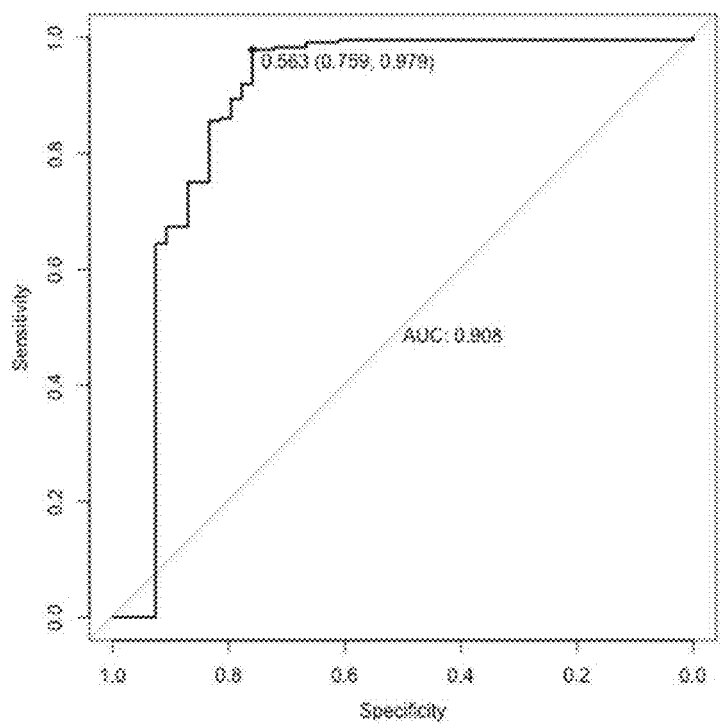
FIG. 21 shows an AUC curve for an ALS metabolite summary score model with an AUC of 0.908. The model correctly classifies 41 of 54 ALS positive cases (76%) with a false negative of 13 (24%). The model also correctly classifies 164 of 168 ALS negative cases (98%) with 4 false positives (92%). Of the 4 false positives, 2 were MS positive.
Figure 26:
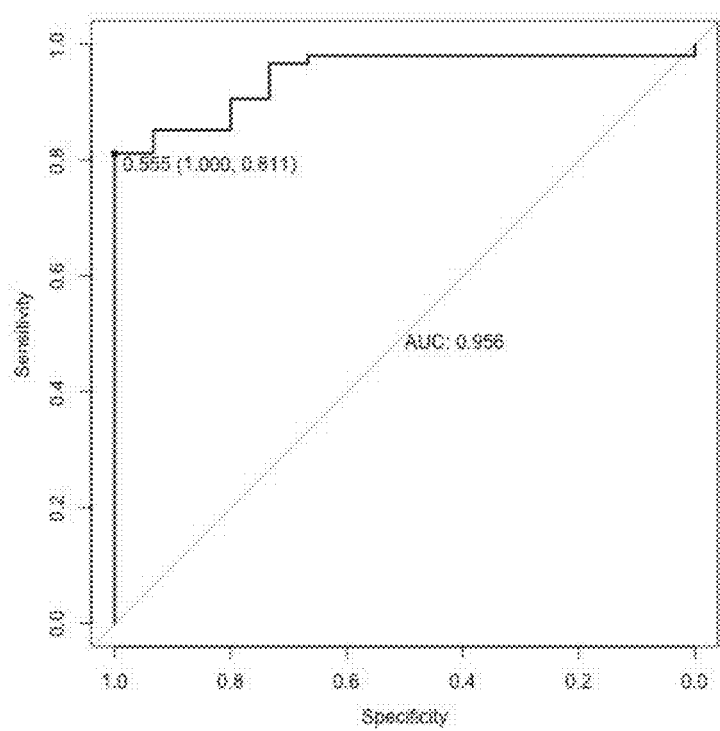
FIG. 26 shows an AUC curve for a systemic lupus erythematosus summary score model. The model was trained using 60 SLE positive cases and 320 SLE negative cases (down-sampled). 15 SLE positive cases and 80 SLE negative cases were used for testing. Using a threshold that maximizes true positives, the model calls 0 false negatives out of 15 SLE positive cases (0%) and 28 false positives out of 80 SLE negative cases (35%). Using a threshold that maximizes true negatives, the model calls 5 false negatives out of 15 positive cases (33%) and 0 false positives out of 80 SLE negative cases (0%).
Figure 31:
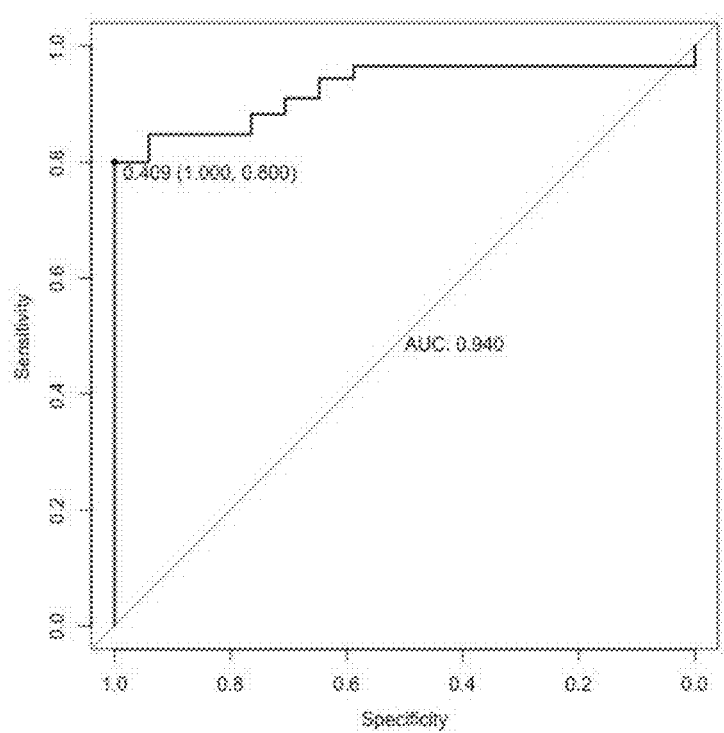
FIG. 31 shows an AUC curve for a fibromyalgia classifier. Using a threshold maximizing true positives, the model calls 0 false negatives out of 17 SLE positive cases (0%) and 28 false positives out of 77 SLE negative cases (36%). Using a threshold maximizing true negatives, the model calls 7 false negatives out of 17 SLE positive cases (43%) and 0 false positives out of 77 SLE negative cases (0%).

For example, 3 different random seed train/test splits were run for all 7 algorithms for 21 models total with respect to MS, ALS, and SLE. Models were run for all conditions with metabolite data for those classifications having more than 35 participants (see FIG. 1). Disease positive samples were run against all negative samples for that specific disease condition. Only models with AUC>0.8 contributed to final participant score. Features were screened for downstream drug metabolites and availability as supplements. Metabolite features were selected by raw p-value>0.1 in Condition vs. Control t-test. The results for MS, ALS, and SLE are shown at least in FIGS. 3-5.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system, comprising:
(a) a processor; and
(b) a non-transitory computer readable medium tangibly encoded with software comprising a plurality of machine learning algorithms together with instructions configured to cause the processor to:
i) receive, via transmission over a network from a server, data related to a specimen taken from an individual, the data indicating the specimen according to a time period, the data received over the network being encrypted during the transmission;
ii) consolidate the plurality of machine learning algorithms into an ensemble of machine learning algorithms;
iii) provide the data as input to the ensemble of machine learning algorithms;
iv) generate, via execution of the ensemble of machine learning algorithms, a classification of the individual relative to a plurality of related classifications by:
a. analyzing, via execution of the ensemble of machine learning algorithms, the data provided as input, the analysis comprising identifying at least one trait of the individual identified from the data via the ensemble of machine learning algorithms performing feature selection;
b. determining, based on the analysis via the ensemble of machine learning algorithms, at least one biomarker associated with the individual, the at least one biomarker corresponding to the at least one trait;
c. analyzing, via further execution of the ensemble of machine learning algorithms, the at least one biomarker, the analysis of the at least one biomarker corresponding to an automated feature selection process based on a set of gene ontology tags;
d. determining, based on the analysis of the at least one biomarker via the ensemble of machine learning algorithms, a likelihood of a disease over the time period; and
e. generating the classification in accordance with information related to the likelihood determined via an output of the ensemble of machine learning algorithms;
v) analyze, via the ensemble of machine learning algorithms, the generated classification;
vi) generate, based on the analysis of the generated classification, a displayable evaluation report, the evaluation report comprising functionality for an intuitive visualization of the classification according to the time period, the evaluation report further comprising information related to a treatment for at least one condition associated with the classification; and vii) cause display, on a display of a device, of the evaluation report thereby providing the functionality for the intuitive visualization of the classification, the intuitive visualization providing functionality for tracking and monitoring the individual as the treatment progresses and updating the display of the evaluation report to visibly display an impact of the treatment on the at least one condition, wherein the impact is determined based on further analysis of the generated classification of the identified biomarkers via the ensemble of machine learning algorithms.

2. The system of claim 1, wherein the classification comprises multiple sclerosis, amyotrophic lateral sclerosis, systemic lupus erythematosus, fibromyalgia, gastrointestinal reflux disease, or any combination thereof.

3. The system of claim 1, wherein the ensemble comprises at least three machine learning algorithms.

4. The system of claim 1, wherein the ensemble of machine learning algorithms comprises a Generalized Linear algorithm, a Random Forests algorithm, a Partial Least Squares algorithm, and Extreme Gradient Boosting algorithm, a Support Vector Machines with Linear Basis Function Kernel algorithm, a Support Vector Machines with Radial Basis Function Kernel, and a Neural Networks algorithm.

5. The system of claim 1, wherein each machine learning algorithm of the ensemble of machine learning algorithms produces an output that is averaged by the software.

6. The system of claim 1, wherein each machine learning algorithm of the ensemble of machine learning algorithms produces an output and wherein at least one output is an input for at least one of the machine learning algorithms.

7. The system of claim 1, wherein at least one machine learning algorithm is trained using data relating to specimens from other individuals.

8. The system of claim 1, wherein the specimen comprises a biological sample.

9. The system of claim 1, wherein the specimen comprises at least one of a sputum sample, a urine sample, a blood sample, a cerebrospinal fluid sample, a stool sample, a hair sample, and a biopsy.

10. The system of claim 1, wherein the data relates to a metabolite, a protein, a nucleic acid, or any combination thereof.

11. The system of claim 10, wherein the metabolite comprises at least one of oleamide, creatine, and 4-methyl-2-oxopentanoate.

12. The system of claim 1, wherein the instructions are further configured to cause the processor to receive a parameter related to the individual and wherein the ensemble machine learning algorithms use the parameter together with the data to generate the classification of the individual relative to the plurality of related classifications.

13. The system of claim 12, wherein the parameter comprises at least one of an age, a gender, a race, a weight, a body mass index (BMI), a height, a waist size, a blood pressure, a heart rate, and a temperature.

14. The system of claim 1, wherein the plurality of related classifications comprise a spectrum of severity of a single disease, a spectrum of prognoses of a single disease, or a spectrum of related diseases.

15. The system of claim 14, wherein the spectrum of related diseases comprise a plurality of neurological diseases that share at least one common feature.

16. A computer implemented method comprising:
(a) receiving, by a device, data relating to a specimen taken from an individual, the data indicating the specimen according to a time period;
(b) consolidating, by the device, a plurality of machine learning algorithms into an ensemble of machine learning algorithms;
(c) providing, by the device, the data as input to the ensemble of machine learning algorithms;
(d) generating, by the device executing the ensemble of machine learning algorithms, a classification of the individual relative to a plurality of related classifications by:
  a. analyzing, via execution of the ensemble of machine learning algorithms, the data provided as input, the analysis comprising identifying at least one trait of the individual identified from the data via the ensemble of machine learning algorithms performing feature selection;
  b. determining, based on the analysis via the ensemble of machine learning algorithms, at least one biomarker associated with the individual, the at least one biomarker corresponding to the at least one trait;
  c. analyzing, via further execution of the ensemble of machine learning algorithms, the at least one biomarker, the analysis of the at least one biomarker corresponding to an automated feature selection process based on a set of gene ontology tags;
  d. determining, based on the analysis of the at least one biomarker via the ensemble of machine learning algorithms, a likelihood of a disease over the time period; and
  e. generating the classification in accordance with information related to the likelihood determined via an output of the ensemble of machine learning algorithms;
(e) analyzing, by the device via the ensemble of machine learning algorithms, the generated classification;
(f) generating, by the device, based on the analysis of the generated classification, a displayable evaluation report, the evaluation report comprising functionality for an intuitive visualization of the classification according to the time period, the evaluation report further comprising information related to a treatment for at least one condition associated with the classification; and
(g) causing display, on a display associated with the device, of the evaluation report thereby providing the functionality for the intuitive visualization of the classification, the intuitive visualization providing functionality for tracking and monitoring the individual as the treatment progresses and updating the display of the evaluation report to visibly display an impact of the treatment on the at least one condition, wherein the impact is determined based on further analysis of the generated classification of the identified biomarkers via the ensemble of machine learning algorithms.

17. A system comprising:
(a) a processor; and
(b) a non-transitory computer readable medium tangibly encoded with software comprising a plurality of machine learning algorithms together with instructions configured to cause the processor to:
  i) receive data related to a specimen taken from an individual, the data indicating the specimen according to a time period;

ii) consolidate the plurality of machine learning algorithms into an ensemble of machine learning algorithms;
iii) provide the data as input to the ensemble of machine learning algorithms;
iv) generate, via execution of the ensemble of machine learning algorithms, an assessment of one or more traits of the individual according to the time period by:
  a. analyzing, via execution of the ensemble of machine learning algorithms, the data provided as input, the analysis comprising identifying the one or more traits of the individual identified from the data via the ensemble of machine learning algorithms performing feature selection;
  b. determining, based on the analysis via the ensemble of machine learning algorithms, one or more biomarker associated with the individual, the at least one biomarker corresponding to the one or more trait;
  c. analyzing, via further execution of the ensemble of machine learning algorithms, the at least one biomarker, the analysis of the at least one biomarker corresponding to an automated feature selection process based on a set of gene ontology tags;
  d. determining, based on the analysis of the at least one biomarker via the ensemble of machine learning algorithms, a likelihood of a disease over the time period; and
  e. generating the assessment in accordance with information related to the likelihood determined via an output of the ensemble of machine learning algorithms;
v) analyze, via the ensemble of machine learning algorithms, the assessment;
vi) generate, based on the analysis of the assessment, a displayable evaluation report, the evaluation report comprising functionality for an intuitive visualization of the assessment according to the time period, the evaluation report further comprising information related to a treatment for at least one condition associated with the assessment and
vii) cause display, on a display of a device, of the evaluation report thereby providing the functionality for the intuitive visualization of the assessment, the intuitive visualization providing functionality for tracking and monitoring the individual as the treatment progresses and updating the display of the evaluation report to visibly display an impact of the treatment on the at least one condition, wherein the impact is determined based on further analysis of the generated assessment of the identified biomarkers via the ensemble of machine learning algorithms.

18. The system of claim 17, wherein the assessment comprises at least one trait selected from a category that is personal characteristics, general health, mental health, health behaviors, interventions, organ systems, environmental, and conditions.

\* \* \* \* \*